(12) United States Patent
Fischer et al.

(10) Patent No.: US 8,013,172 B2
(45) Date of Patent: Sep. 6, 2011

(54) CYCLOALKYLPHENYL SUBSTITUTED CYCLIC KETOENOLS

(75) Inventors: Reiner Fischer, Monheim (DE);
Thomas Bretschneider, Lohmar (DE);
Stefan Lehr, Liederbach (DE); Dieter Feucht, Eschborn (DE); Eva-Maria Franken, Leichlingen (DE); Olga Malsam, Rösrath (DE); Alfred Angermann, Kriftel (DE); Guido Bojack, Wiesbaden-Naurod (DE);
Christian Arnold, Langenfeld (DE);
Martin Jeffrey Hills, Idstein (DE);
Heinz Kehne, Hofheim (DE);
Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 108 days.

(21) Appl. No.: 12/280,277

(22) PCT Filed: Feb. 8, 2007

(86) PCT No.: PCT/EP2007/001075
§ 371 (c)(1),
(2), (4) Date: Jan. 24, 2009

(87) PCT Pub. No.: WO2007/096058
PCT Pub. Date: Aug. 30, 2007

(65) Prior Publication Data
US 2009/0305891 A1 Dec. 10, 2009

(30) Foreign Application Priority Data

Feb. 21, 2006 (DE) .......................... 10 2006 007 882

(51) Int. Cl.
*C07D 207/00* (2006.01)
*C07D 209/54* (2006.01)
(52) U.S. Cl. ........................................ 548/544; 548/408
(58) Field of Classification Search .................. 548/408, 548/544
See application file for complete search history.

(56) References Cited

U.S. PATENT DOCUMENTS

| | | |
|---|---|---|
| 2,842,476 A | 7/1958 | Schreiber |
| 3,542,809 A | 11/1970 | Nakanishi |
| 4,013,690 A | 3/1977 | Closse et al. |
| 4,021,224 A | 5/1977 | Pallos et al. |
| 4,091,006 A | 5/1978 | Durden, Jr. et al. |
| 4,175,135 A | 11/1979 | Haines |
| 4,186,130 A | 1/1980 | Teach |
| 4,209,432 A | 6/1980 | Roth |
| 4,256,657 A | 3/1981 | Wheeler |
| 4,256,658 A | 3/1981 | Wheeler |
| 4,256,659 A | 3/1981 | Wheeler |
| 4,257,858 A | 3/1981 | Wheeler |
| 4,283,348 A | 8/1981 | Wheeler |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,436,666 A | 3/1984 | Wheeler |
| 4,526,723 A | 7/1985 | Wheeler et al. |
| 4,551,547 A | 11/1985 | Wheeler |
| 4,558,043 A | 12/1985 | Wenk et al. |
| 4,613,617 A | 9/1986 | Sousa |
| 4,623,727 A | 11/1986 | Hubele |
| 4,632,698 A | 12/1986 | Wheeler |
| 4,639,266 A | 1/1987 | Heubach et al. |
| 4,659,372 A | 4/1987 | Wheeler |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,094,681 A | 3/1992 | Kramer et al. |
| 5,102,667 A | 4/1992 | Dubroeucq et al. |
| 5,116,836 A | 5/1992 | Fischer et al. |
| 5,164,179 A | 11/1992 | Hioki et al. |
| 5,225,434 A | 7/1993 | Bertram et al. |
| 5,258,527 A | 11/1993 | Krauskopf et al. |

(Continued)

FOREIGN PATENT DOCUMENTS

CA 1162071 2/1984

(Continued)

OTHER PUBLICATIONS

Norman Sonntag "The Reactions of Aliphatic Acid Chlorides", Chem Reviews (1953), vol. 52, pp. 237-416. Annemarie Closse et al., XP-002433232 "2,3-Dihydrobenzofuran-2-ones: A New Class of Highly Potent Antiinflammatory Agents", J. Med Chem. 1981, vol. 24, pp. 1465-1471.

(Continued)

*Primary Examiner* — Nizal Chandrakumar
(74) *Attorney, Agent, or Firm* — Baker Donelson Bearman, Caldwell & Berkowitz, PC

(57) ABSTRACT

The disclosure relates to novel cycloalkylphenyl-substituted cyclic ketoenols of the formula (I)

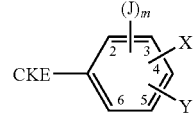

in which
J, X, Y, m and CKE are as defined above,
to processes and intermediates for their preparation and to their use as pesticides and/or herbicides.
Moreover, the disclosure relates to selective herbicidal compositions comprising, firstly, the cycloalkylphenyl-substituted cyclic ketoenols and, secondly, a crop plant compatibility-improving compound.
The disclosure furthermore relates to increasing the activity of crop protection compositions comprising compounds of the formula (I) by adding ammonium or phosphonium salts and, if appropriate, penetrants.

16 Claims, No Drawings

U.S. PATENT DOCUMENTS

| | | | |
|---|---|---|---|
| 5,262,383 | A | 11/1993 | Fischer et al. |
| 5,298,501 | A | 3/1994 | Cummings |
| 5,314,863 | A | 5/1994 | Loher et al. |
| 5,332,720 | A | 7/1994 | Kruger et al. |
| 5,380,852 | A | 1/1995 | Schutze et al. |
| 5,393,729 | A | 2/1995 | Fischer et al. |
| 5,401,700 | A | 3/1995 | Sohn et al. |
| 5,407,897 | A | 4/1995 | Cary et al. |
| 5,462,912 | A | 10/1995 | Hioki et al. |
| 5,462,913 | A | 10/1995 | Fischer et al. |
| 5,494,890 | A | 2/1996 | Cederbaum et al. |
| 5,504,057 | A | 4/1996 | Fischer et al. |
| 5,516,750 | A | 5/1996 | Willms et al. |
| 5,538,937 | A | 7/1996 | Hasebe et al. |
| 5,565,450 | A | 10/1996 | Fischer et al. |
| 5,567,671 | A | 10/1996 | Fischer et al. |
| 5,589,469 | A | 12/1996 | Fischer et al. |
| 5,610,122 | A | 3/1997 | Fischer et al. |
| 5,622,917 | A | 4/1997 | Fischer et al. |
| 5,631,279 | A | 5/1997 | Crespo et al. |
| 5,700,758 | A | 12/1997 | Rosch et al. |
| 5,705,476 | A | 1/1998 | Hoffarth |
| 5,739,079 | A | 4/1998 | Holdgrun et al. |
| 5,789,440 | A | 8/1998 | Ellsworth et al. |
| 5,792,755 | A | 8/1998 | Sagenmuller et al. |
| 5,808,135 | A | 9/1998 | Fischer et al. |
| 5,811,374 | A | 9/1998 | Bertram et al. |
| 5,830,825 | A | 11/1998 | Fischer et al. |
| 5,830,826 | A | 11/1998 | Fischer et al. |
| 5,840,661 | A | 11/1998 | Fischer et al. |
| 5,945,444 | A | 8/1999 | Fischer et al. |
| 5,977,029 | A | 11/1999 | Fischer et al. |
| 6,071,937 | A | 6/2000 | Bretschneider et al. |
| 6,090,805 | A | 7/2000 | Williams et al. |
| 6,114,374 | A | 9/2000 | Lieb et al. |
| 6,133,296 | A | 10/2000 | Lieb et al. |
| 6,140,358 | A | 10/2000 | Lieb et al. |
| 6,200,932 | B1 | 3/2001 | Fischer et al. |
| 6,235,680 | B1 | 5/2001 | Ziemer et al. |
| 6,251,827 | B1 | 6/2001 | Ziemer et al. |
| 6,251,830 | B1 | 6/2001 | Fischer et al. |
| 6,251,833 | B1 | 6/2001 | Erdelen et al. |
| 6,288,102 | B1 | 9/2001 | Hagemann et al. |
| 6,316,486 | B1 | 11/2001 | Lieb et al. |
| 6,358,887 | B1 | 3/2002 | Fischer et al. |
| 6,410,480 | B1 | 6/2002 | Muhlebach et al. |
| 6,417,370 | B1 | 7/2002 | Lieb et al. |
| 6,451,843 | B1 * | 9/2002 | Lieb et al. ............ 514/422 |
| 6,458,965 | B1 | 10/2002 | Lieb et al. |
| 6,472,419 | B1 | 10/2002 | Fischer et al. |
| 6,511,940 | B1 | 1/2003 | Ziemer et al. |
| 6,511,942 | B1 | 1/2003 | Lieb et al. |
| 6,515,184 | B1 | 2/2003 | Fischer et al. |
| 6,555,499 | B1 | 4/2003 | Glock et al. |
| 6,589,976 | B1 | 7/2003 | Fischer et al. |
| 6,602,823 | B1 | 8/2003 | Rochling et al. |
| 6,608,211 | B1 | 8/2003 | Hagemann et al. |
| 6,642,180 | B1 * | 11/2003 | Fischer et al. ........ 504/246 |
| 6,645,914 | B1 | 11/2003 | Woznica et al. |
| 6,861,391 | B1 | 3/2005 | Fischer et al. |
| 6,894,005 | B1 | 5/2005 | Maetzke et al. |
| 6,906,007 | B2 | 6/2005 | Fischer et al. |
| 6,958,383 | B2 | 10/2005 | Desmazeau et al. |
| 6,962,894 | B1 | 11/2005 | Glock |
| 6,974,827 | B2 | 12/2005 | Fischer et al. |
| 7,727,933 | B2 * | 6/2010 | Fischer et al. ........ 504/283 |
| 7,776,791 | B2 * | 8/2010 | Fischer et al. ........ 504/282 |
| 2003/0216260 | A1 | 11/2003 | Ruther et al. |
| 2003/0224939 | A1 | 12/2003 | Miles |
| 2004/0266624 | A1 | 12/2004 | Hofer |
| 2005/0009880 | A1 | 1/2005 | Cottrell et al. |
| 2005/0054535 | A1 | 3/2005 | Fischer et al. |
| 2005/0090399 | A1 | 4/2005 | Friedmann et al. |
| 2005/0096386 | A1 | 5/2005 | Cottrell et al. |
| 2006/0160847 | A1 | 7/2006 | Fischer et al. |
| 2006/0166829 | A1 | 7/2006 | Fischer et al. |
| 2007/0015664 | A1 | 1/2007 | Fischer et al. |
| 2007/0032539 | A1 | 2/2007 | Himmler |
| 2007/0066488 | A1 | 3/2007 | Fischer et al. |
| 2007/0129252 | A1 | 6/2007 | Fischer et al. |
| 2007/0225167 | A1 | 9/2007 | Fischer et al. |
| 2007/0225170 | A1 | 9/2007 | Fischer et al. |
| 2007/0244007 | A1 | 10/2007 | Fischer et al. |
| 2007/0275858 | A1 | 11/2007 | Fischer et al. |
| 2007/0298968 | A1 | 12/2007 | Bretschneider et al. |
| 2007/0298969 | A1 | 12/2007 | Fischer et al. |

FOREIGN PATENT DOCUMENTS

| | | |
|---|---|---|
| CA | 2382432 | 3/2001 |
| CA | 2535512 | 2/2005 |
| CA | 2572141 | 1/2006 |
| CA | 2586096 | 6/2006 |
| CA | 2595602 | 6/2006 |
| CA | 2597777 | 8/2006 |
| DE | 1945703 | 7/1970 |
| DE | 1695385 | 4/1971 |
| DE | 2218097 | 11/1972 |
| DE | 2350547 | 4/1974 |
| DE | 2361084 | 6/1974 |
| DE | 2813341 | 10/1978 |
| DE | 4014420 | 4/1991 |
| DE | 19621522 | 12/1997 |
| DE | 10301804 | 7/2004 |
| DE | 102005051325 | 5/2007 |
| DE | 102005059891 | 6/2007 |
| EP | 0036106 | 9/1981 |
| EP | 86750 | 8/1983 |
| EP | 94349 | 11/1983 |
| EP | 174562 | 3/1986 |
| EP | 191736 | 8/1986 |
| EP | 0262399 | 4/1988 |
| EP | 269806 | 6/1988 |
| EP | 333131 | 9/1989 |
| EP | 0346620 | 12/1989 |
| EP | 355599 | 2/1990 |
| EP | 377893 | 7/1990 |
| EP | 415211 | 3/1991 |
| EP | 442073 | 8/1991 |
| EP | 442077 | 8/1991 |
| EP | 0453086 | 10/1991 |
| EP | 456063 | 11/1991 |
| EP | 492366 | 7/1992 |
| EP | 508126 | 10/1992 |
| EP | 521334 | 1/1993 |
| EP | 528156 | 2/1993 |
| EP | 582198 | 2/1994 |
| EP | 588137 | 3/1994 |
| EP | 596298 | 5/1994 |
| EP | 613618 | 9/1994 |
| EP | 613884 | 9/1994 |
| EP | 613885 | 9/1994 |
| EP | 0647637 | 4/1995 |
| EP | 0664081 | 7/1995 |
| EP | 0668267 | 8/1995 |
| EP | 0681865 | 11/1995 |
| FR | 2600494 | 12/1987 |
| GB | 2266888 | 11/1993 |
| JP | 11-152273 | 6/1999 |
| JP | 2000-53670 | 9/2001 |
| WO | 9107874 | 6/1991 |
| WO | 9108202 | 6/1991 |
| WO | 9216108 | 10/1992 |
| WO | 9216510 | 10/1992 |
| WO | 9414785 | 7/1994 |
| WO | 94/29268 | 12/1994 |
| WO | 95/01997 | 1/1995 |
| WO | 9507897 | 3/1995 |
| WO | 9514012 | 5/1995 |
| WO | 9517817 | 7/1995 |
| WO | 9520572 | 8/1995 |
| WO | 9526345 | 10/1995 |
| WO | 9526954 | 10/1995 |
| WO | 9601798 | 1/1996 |
| WO | 9602539 | 2/1996 |
| WO | 9603366 | 2/1996 |
| WO | 9611574 | 4/1996 |
| WO | 9620196 | 7/1996 |

| | | |
|---|---|---|
| WO | 9621652 | 7/1996 |
| WO | 9625395 | 8/1996 |
| WO | 9635664 | 11/1996 |
| WO | 9701535 | 1/1997 |
| WO | 9702243 | 1/1997 |
| WO | 9714667 | 4/1997 |
| WO | 9716436 | 5/1997 |
| WO | 9719941 | 6/1997 |
| WO | 9736868 | 10/1997 |
| WO | 9743275 | 11/1997 |
| WO | 9805638 | 2/1998 |
| WO | 9806721 | 2/1998 |
| WO | WO99/48869 * | 3/1998 |
| WO | 9825928 | 6/1998 |
| WO | 9835553 | 8/1998 |
| WO | 9839281 | 9/1998 |
| WO | 9916748 | 4/1999 |
| WO | WO 99/55673 * | 4/1999 |
| WO | 9924437 | 5/1999 |
| WO | 9943649 | 9/1999 |
| WO | 9943699 | 9/1999 |
| WO | 9947525 | 9/1999 |
| WO | 9948869 | 9/1999 |
| WO | WO 99/48869 | 9/1999 |
| WO | 9955673 | 11/1999 |
| WO | WO 99/55673 | 11/1999 |
| WO | 9966795 | 12/1999 |
| WO | 0035278 | 6/2000 |
| WO | 0117351 | 3/2001 |
| WO | 0117352 | 3/2001 |
| WO | 0117353 | 3/2001 |
| WO | 0117972 | 3/2001 |
| WO | 0117973 | 3/2001 |
| WO | 0123354 | 4/2001 |
| WO | 0174770 | 10/2001 |
| WO | 0179204 | 10/2001 |
| WO | 0198288 | 12/2001 |
| WO | 03013249 | 2/2003 |
| WO | 03028466 | 4/2003 |
| WO | 03062244 | 7/2003 |
| WO | 2004007448 | 1/2004 |
| WO | 2004024688 | 3/2004 |
| WO | 2004048314 | 6/2004 |
| WO | WO 2004/048314 | 6/2004 |
| WO | 2004065366 | 8/2004 |
| WO | 2004080962 | 9/2004 |
| WO | 2004111042 | 12/2004 |
| WO | WO 2004111042 * | 12/2004 |
| WO | 2005005428 | 1/2005 |
| WO | 2005016873 | 2/2005 |
| WO | 2005044791 | 5/2005 |
| WO | 2005044796 | 5/2005 |
| WO | 2005048710 | 6/2005 |
| WO | 2005049569 | 6/2005 |
| WO | 2005066125 | 7/2005 |
| WO | 2005092897 | 10/2005 |
| WO | 2006000355 | 1/2006 |
| WO | 2006029799 | 3/2006 |
| WO | 2006056281 | 6/2006 |
| WO | 2006056282 | 6/2006 |
| WO | 2006089633 | 8/2006 |
| WO | 2007048545 | 5/2007 |
| WO | 2007073856 | 7/2007 |

OTHER PUBLICATIONS

P.L. Compagnon et M. Miocque "Addition Des Reactifs Nucleophiles Sur La Triple Liaison Nitrile", Ann. Chim., 1970, vol. 14, No. 5, pp. 11-27. English Summary on p. 11. Annemarie Closse et al., XP-002433232 "2,3-Dihydrobenzofuran-2-ones: A New Class of Highly Potent Antiinflammatory Agents", J. Med Chem. 1981, vol. 24, pp. 1465-1471.
P.L. Compagnon et M. Miocque "Addition Des Reactifs Nucleophiles Sur La Triple Liaison Nitrile", Ann. Chim., 1970, vol. 14, No. 5, pp. 11-27. English Summary on p. 11.
John T. Edward et al. "Sterochemistry of the Bucherer-Bergs and Strecker Reactions of 4-tert-Butylcylohexanone", 53 Can. J. Chem. 3339-3350 (1975).
H.R.Harrison et al. "Use of Molecular Sieves in the Methyl Esterification of Carboxylic Acids", Chemistry and Industry, p. 1568 (Nov. 9, 1968).
Seikichi Suzuki et al. "Studies on Antiviral Agents" Chemical and Pharmaceutical Bulletin, vol. 15 (1967), pp. 1120-1122.
Bhabatosh Bhattacharya "Isoquinoline Derivatives: Part XVIII-Formation of I-Alkyl—(or alkaryl or aryl)-3-methyl-7-chloro-(or 5-chloro)-isoquinolines", Indian J. Chem, vol. 6 (1968), pp. 341-345.
Edwards et al. "Constituents of the Higher Fungi", J. Chem. Soc. (c) (1967), pp. 405-409.
L. Munday "Amino-acids of the Cyclohexane Series", J. Chem. Soc. (1961), pp. 4372-4379.
Mark S. Chambers et al. "An Asymmetric Synthesis of Thiotetronic Acids using Chirality Transfer via an Allyl Xanthate-to-Dithiocarbonate Rearrangement", J. Chem. Soc., Chem. Commun. (1987), pp. 1228-1230.
A.A. Sousa et al. "Esters of 3-Hydroxy-2-Arylindones, a New Class of Acaricide", J. Economic Entomology (1973) vol. 66, No. 2, pp. 584-586.
Thomas N. Wheeler "Novel Photochemical Synthesis of 2-Aryl-1,3-cyclohexanediones", J. Org. Chem., (1979), vol. 44, No. 26.
Kazuo Tsuzuki et al. "Syntheses and Biological Activities of Thiotetromycin Analogs", The Journal of Antibiotics, vol. XXXVI, No. 11 (1983), pp. 1589-1591.
Roland Schmierer et al. "Cyclisierung von N-Acylalanin- und N-Acylglycinestern", Liebigs Ann. Chem., (1985), pp. 1095-1098. [English-language abstract included].
Susumu Nakanishi et al. "Synthesis of Chlorocarbonyl Ketenes", Organic Preparation and Procedures Int., vol. 7, No. 4 (1975), pp. 155-158.
Enrico Baciocchi et al. "Dimethyl Arylmalonates from Cerium (IV) Ammonium Nitrate Promoted Reactions of Dimethyl Malonate with Aromatic Compounds in Methanol", Tetrahedron Letters, (1986), vol. 27, No. 24, pp. 2763-2766.
Jason Micklefield et al. "Alkylation and Acylation of 5-Phenylsulphonyl and 5-Cyanobutyrolactones", Tetrahedron, (1992), vol. 48, No. 36, pp. 7519-7526.
Roger Ketcham et al. "Synthesis of Heterocycles. 174 (1,2) Substituted Thiazines and Bisthiazinyls from Dithiooxamide and Trichlorophenyl Malonates", J. Heterocyclic Chem., vol. 10, (1973), pp. 223-224.
White et al. "Darzens Condensation of a-Halolactones. Glycidic Lactones as Intermediates in Acetogenin Synthesis", American Chemical Society (1971), vol. 93:1 pp. 281-282.
Peter Baur et al. "Polydispurse Ethoxylated Fatty Alcohol Surfactants as Accelerators of Cuticular Pentration.1. Effects of Ethoxy Chain Length and the Size of the Penetrants", Pestic. Sci. (1997), vol. 51, pp. 131-152.
A.M. Chirazi et al. "Zur Synthese von Kawalactonderivaten", Arch. Pharm., (1976) vol. 309, pp. 558-564. [English-language abstract included].
Askani "Zur Reaktion von Cyclohexadien-(1.3) mit Azodicarbonsaure-diathylester", Chem. Ber., (1965) vol. 98, pp. 2551-2555. [Relevance found in the specification at p. 132].
E. Ziegler et al. "Uber Derivate des 2-Phenyl-4-hydroxy-[1,3-thiazinons-(6)]", Monatsh. Chem. (1964) vol. 95, pp. 147-155. [Relevance found in the specification at p. 2].
Boltze et al. "Zur Synthese 3-substituierter 4-Hydroxy-pyrone-(2), I" Chem. Ber. (1958) vol. 91, pp. 2849-2853. [Relevance found in the specification at p. 2].
Diels et al. "Uber das aus Cylopentadien und Azoester entstehende Endomethylen-piperidazin und seine Uber fuhrung in 1,3-Diamino-cyclopentan" Liebigs Ann. Chem. (1925) vol. 443, pp. 242-263. [Relevance found in the specification at p. 132].
Dannenberg et al. "Versuche zur Synthese des „Steranthrens" III, Liebigs Ann. Chem. (1954) vol. 585, pp. 1-15. [Relevance found in the specification at p. 132].
George Thieme Verlag Stuttgart "Reaktionen der organischen Synthese, C. Ferri", Organische Reactionen (1978) p. 212. and p. 513-515. [Relevance found in the specification at p. 132].
H. Henecka et al "Methoden der Organischen Chemie", (1952) vol. 8. pp. 467-469. [Relevance found in the specification at p. 135].
International Search Report of PCT/EP2007/001075, Aug. 28, 2008.

* cited by examiner

CYCLOALKYLPHENYL SUBSTITUTED CYCLIC KETOENOLS

CROSS REFERENCE TO RELATED APPLICATIONS

This application is a §371 National Stage Application of PCT/EP2007/001075, filed Feb. 8, 2007, which claims priority to German Application No. 10 2006 007 882.9, filed Feb. 21, 2006.

BACKGROUND OF THE INVENTION

1. Field of the Invention

The present invention relates to novel cycloalkylphenyl-substituted cyclic ketoenols, to a plurality of processes for their preparation and to their use as pesticides and/or herbicides. The invention also provides selective herbicidal compositions comprising, firstly, the cycloalkylphenyl-substituted cyclic ketoenols and, secondly, a crop plant compatibility-improving compound.

The present invention furthermore relates to increasing the activity of crop protection compositions comprising, in particular, cycloalkylphenyl-substituted cyclic ketoenols by addition of ammonium or phosphonium salts and, if appropriate, penetrants, to the corresponding compositions, to processes for their preparation and to their use in crop protection as insecticides and/or acaricides and/or for preventing unwanted vegetation.

2. Description of Related Art

Pharmaceutical properties of 3-acylpyrrolidine-2,4-diones are described in the prior art (S. Suzuki et al. Chem. Pharm. Bull. 15 1120 (1967)). Furthermore, R. Schmierer and H. Mildenberger (Liebigs Ann. Chem. 1985, 1095) synthesized N-phenylpyrrolidine-2,4-diones. A biological activity of these compounds has not been described.

EP-A-0 262 399 and GB-A-2 266 888 disclose compounds of a similar structure (3-arylpyrrolidine-2,4-diones); however, a herbicidal, insecticidal or acaricidal action of these compounds is not known. Known to have a herbicidal, insecticidal or acaricidal action are unsubstituted bicyclic 3-arylpyrrolidine-2,4-dione derivatives (EP-A-355 599, EP-A-415 211 and JP-A-12-053 670), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073), and also 1H-arylpyrrolidinedione derivatives (EP-A-456 063, EP-A-521 334, EP-A-596 298, EP-A-613 884, EP-A-613 885, WO 95/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633, DE-A-05051325, DE-A-05059891).

It is known that certain substituted $\Delta^3$-dihydrofuran-2-one derivatives have herbicidal properties (cf. DE-A-4 014 420). The synthesis of the tetronic acid derivatives (such as, for example, 3-(2-methylphenyl)-4-hydroxy-5-(4-fluorophenyl)-$\Delta^3$-dihydrofuranone-(2) used as starting materials is also described in DE-A-4 014 420. Compounds of a similar structure with no stated insecticidal and/or acaricidal activity are known from the publication Campbell et al., J. Chem. Soc., Perkin Trans. 1, 1985, (8) 1567-76. Furthermore, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770, WO 03/013 249, WO 04/024 688, WO 04/080 962, WO 04/111 042, WO 05/092897, WO 06/000355, WO06/029799, WO 06/089633, DE-A-05051325, DE-A-05059891. Also known are 3-aryl-$\Delta^3$-dihydrothiophenone derivatives (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042, WO 05/092897, WO 06/029799).

Certain phenylpyrone derivatives unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849); however, a possible use of these compounds as pesticides is not stated. Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042, WO 05/092897, WO 06/029799.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)); however, a possible use of these compounds as pesticides is not stated. 5-Phenyl-1,3-thiazine derivatives which are substituted in the phenyl ring and have herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972, WO 01/74770, WO 03/013249, WO 04/080 962, WO 04/111 042, WO 05/092897, WO 06/029799.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/013249, WO 04/080 962, WO 04/111 042, WO 05/092897, WO 06/029799). Also known are compounds substituted in a similar manner; 3-hydroxy-5,5-dimethyl-2-phenylcyclopent-2-en-1-one from the publication Micklefield et al., Tetrahedron, (1992), 7519-26 and the natural compound involutin (−)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Also known is 2-(2,4,6-trimethylphenyl)-1,3-indanedione from the publication J. Economic Entomology, 66, (1973), 584 and the laid-open publication DE-A 2 361 084, with herbicidal and acaricidal actions being stated.

It is known that certain substituted 2-arylcyclohexanediones have herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A2 813 341, and also Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111 042, WO 05/092897, WO 06/029799).

It is known that certain substituted 4-arylpyrazolidine-3,5-diones have acaricidal, insecticidal and herbicidal properties (cf., for example, WO 92/16 510, EP-A-508 126, WO 96/11 574, WO96/21 652, WO99/47525, WO 01/17 351, WO01/17 352, WO 01/17 353, WO 01/17 972, WO 01/17 973, WO 03/028 466, WO 03/062 244, WO 04/080 962, WO 04/111 042, WO 05/005428, WO 05/016873, WO 05/092897, WO 06/029799).

It is known that certain tetrahydropyridones have herbicidal properties: JP-A-0 832 530. Also known are specific 4-hydroxytetrahydropyridones having acaricidal, insecticidal and herbicidal properties: JP-A-11 152 273. Furthermore, 4-hydroxytetrahydropyridones as pesticides and herbicides are disclosed in WO 01/79204.

It is furthermore known that certain 5,6-dihydropyrone derivatives as protease inhibitors have antiviral properties: WO 95/14012. Furthermore, 4-phenyl-6-(2-phenethyl)-5,6-dihydropyrone is known from the synthesis of kavalactone derivatives: Kappe et al., Arch. Pharm. 309, 558-64 (1976). Moreover, 5,6-dihydropyrone derivatives are known as intermediates: White, J. D., Brenner, J. B., Deinsdale, M. J., J. Amer. Chem. Soc. 93, 281-2 (1971). 3-Phenyl-5,6-dihydropyrone derivatives which can be applied as crop protection agents are described in WO 01/98288.

However, the efficacy and activity spectrum of these compounds, in particular at low application rates and concentrations, are not always satisfactory. Furthermore, the compatibility of these compounds with crops is not always sufficient.

SUMMARY OF THE INVENTION

This invention now provides novel compounds of the formula (I)

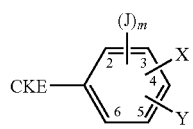

(I)

in which

J represents optionally substituted cycloalkyl which may optionally be interrupted by heteroatoms, X represents hydrogen, alkyl, halogen, haloalkyl, alkoxy or haloalkoxy, Y represents hydrogen, alkyl, haloalkyl, halogen, alkoxy or haloalkoxy, m represents a number 1, 2 or 3, with the proviso that at least one of the radicals J, X or Y is located in the 2-position of the phenyl radical and is not hydrogen, CKE represents one of the groups

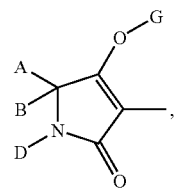 (1)

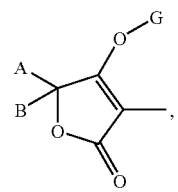 (2)

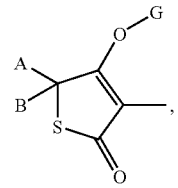 (3)

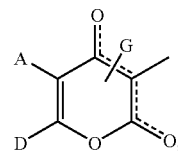 (4)

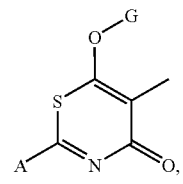 (5)

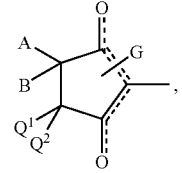 (6)

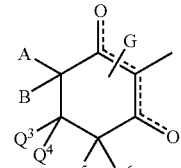 (7)

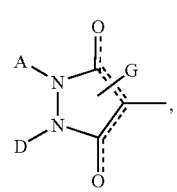 (8)

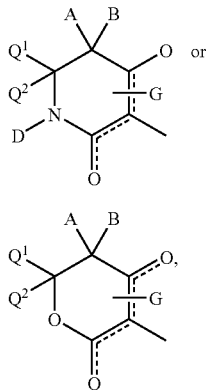
(9)

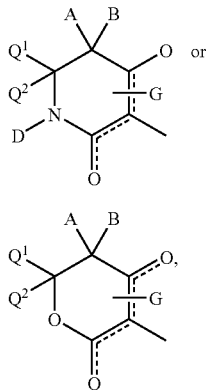
(10)

in which

A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which is unsubstituted or substituted in the A, D moiety and optionally contains at least one (in the case of CKE=8 one further) heteroatom, or A and $Q^1$ together represent alkanediyl or alkenediyl which is optionally interrupted by a carbonyl group or heteratoms, which is optionally substituted by halogen, hydroxyl, in each case optionally substituted alkyl, alkoxy, alkylthio, cycloalkyl, benzyloxy or aryl and in which optionally two not directly adjacent carbon atoms form a further optionally substituted cycle which may optionally be interrupted by heteroatoms or D and $Q^1$ together with the atoms to which they are attached represent a saturated or unsaturated cycle which optionally contains at least one heteroatom and is unsubstituted or substituted in the D, $Q^1$ moiety, $Q^1$ represents hydrogen, alkyl, alkoxyalkyl, optionally substituted cycloalkyl (in which optionally one methylene group is replaced by oxygen or sulphur) or optionally substituted phenyl, $Q^2$, $Q^4$, $Q^5$ and $Q^6$ independently of one another represent hydrogen or alkyl, $Q^3$ represents hydrogen, represents optionally substituted alkyl, alkoxyalkyl, alkyl-thioalkyl, optionally substituted cycloalkyl (in which optionally one methylene group is replaced by oxygen or sulphur) or optionally substituted phenyl, or $Q^1$ and $Q^2$ together with the carbon atom to which are they are attached represent an unsubstituted or substituted cycle which optionally contains a heteroatom, or $Q^3$ and $Q^4$ together with the carbon atom to which they are attached represent a saturated or unsaturated unsubstituted or substituted cycle which optionally contains a heteroatom, G represents hydrogen (a) or represents one of the groups

(b)

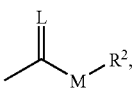
(c)

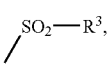
(d)

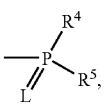
(e)

E or
(f)

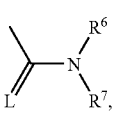
(g)

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represents in each case optionally substituted phenyl, benzyl, phenoxy or phenylthio, $R^6$ and $R^7$ independently of one another represent hydrogen, represent in each case optionally halogen-substituted alkyl, cycloalkyl, alkenyl, alkoxy, alkoxyalkyl, represent optionally substituted phenyl, represent optionally substituted benzyl, or together with the N-atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if appropriate, may be separated in a customary manner. The present invention provides both the pure isomers and the isomer mixtures, their preparation and use, and compositions comprising them. However, for the sake of simplicity, hereinbelow only compounds of the formula (I) are referred to, although what is meant are both the pure compounds and, if appropriate, also mixtures having varying proportions of isomeric compounds.

DETAILED DESCRIPTION OF THE PREFERRED EMBODIMENT

Including the meanings (1) to (10) of group CKE, the following principal structures (I-1) to (I-10) result:

in which

A, B, D, G, J, m, $Q^1$, $Q^2$, $Q^3$, $Q^4$, $Q^5$, $Q^6$, X and Y are as defined above.

Including the different meanings (a), (b), (c), (d), (e), (f) and (g) of group G, the following principal structures (I-1-a) to (I-1-g) result if CKE represents group (1)

(I-1-c):
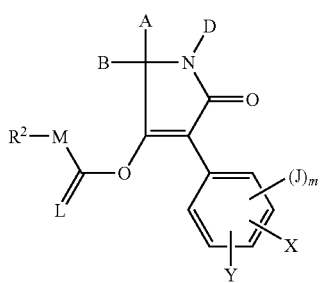
(I-1-d):
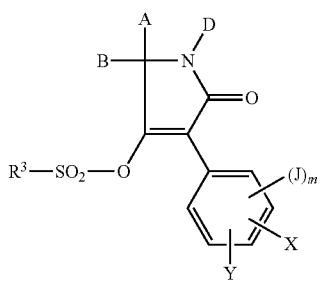
(I-1-e):
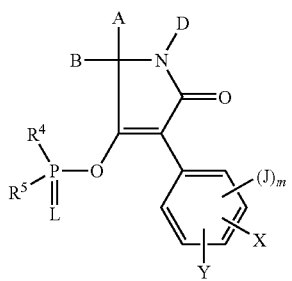
(I-1-f):
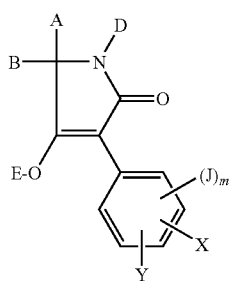
(I-1-g):
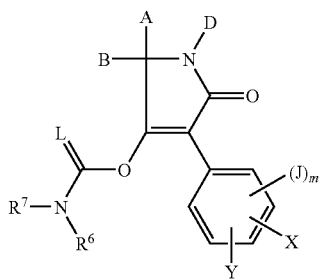
in which
A, B, D, E, J, L, m, M, X, Y, $R^1$, $R^2$, $R^3$, $R^4$, $R^5$, $R^6$ and $R^7$ are as defined above.
Including the different meanings (a), (b), (c), (d), (e), (f) and (g) of group G, the following principal structures (I-2-a) to (I-2-g) result if CKE represents group (2)
(I-2-a):
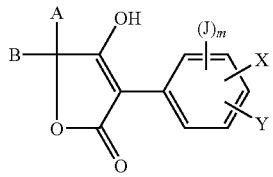
(I-2-b):
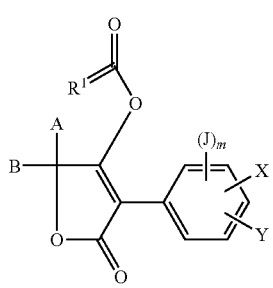
(I-2-c):
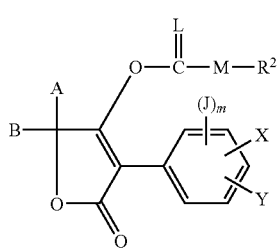
(I-2-d):
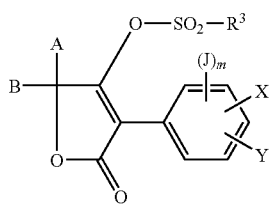
(I-2-e):
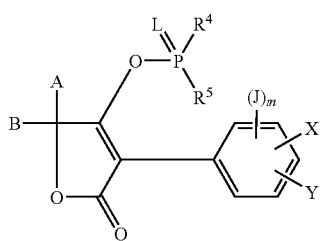
(I-2-f):
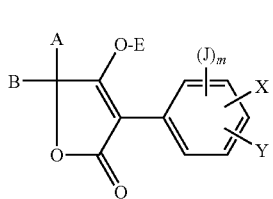

(I-2-g):

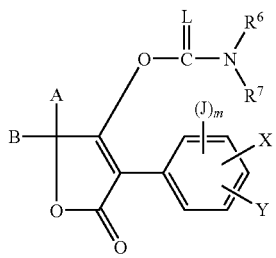

in which
A, B, E, J, L, m, M, X, Y, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-3-a) to (I-3-g) result if CKE represents group (3)

(I-3-a):

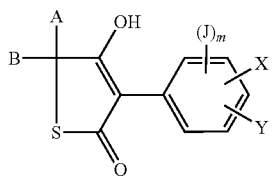

(I-3-b):

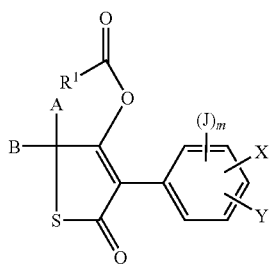

(I-3-c):

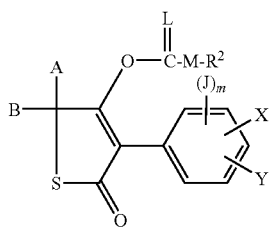

(I-3-d):

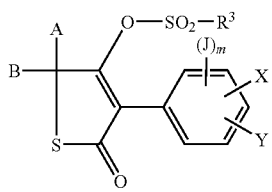

(I-3-e):

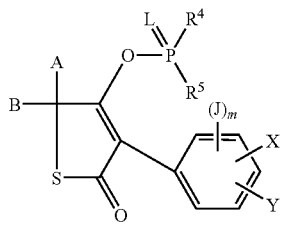

(I-3-f):

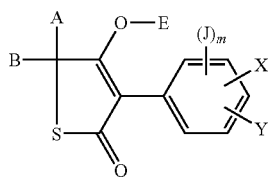

(I-3-g):

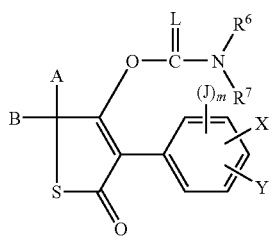

in which
A, B, E, J, L, m, M, X, Y, $R^1$, $R^2$, $R^3$, $R^4$, $R^5$, $R^6$ and $R^7$ are as defined above.

Depending on the position of the substituent G, the compounds of the formula (I-4) can be present in the two isomeric forms of the formulae (I-4-A) and (I-4-B)

(I-4-A)

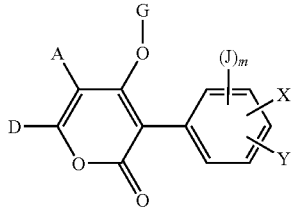

(I-4-B)

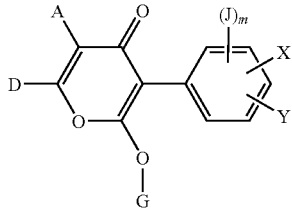

which is meant to be indicated by the dashed line in formula (I-4).

The compounds of the formulae (I-4-A) and (I-4-B) can be present both as mixtures and in the form of their pure isomers. If appropriate, mixtures of the compounds of the formulae (I-4-A) and (I-4-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric form.

Including the different meanings (a), (b), (c), (d), (e), (f) and (g) of group G, the following principal structures (I-4-a) to (I-4-g) result if CKE represents group (4)

(I-4-a):

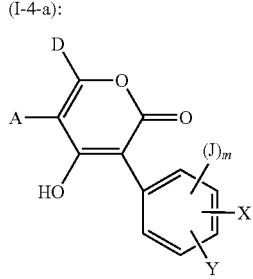

(I-4-b):

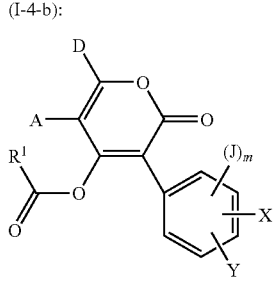

(I-4-c):

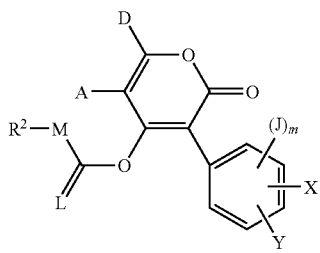

(I-4-d):

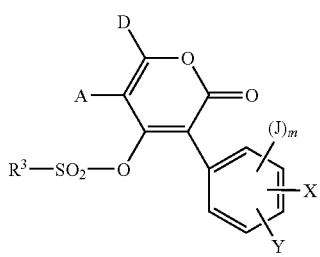

(I-4-e):

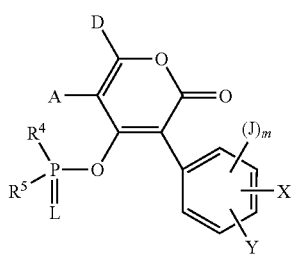

-continued (I-4-f):

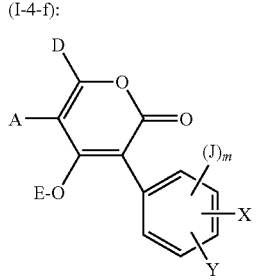

(I-4-g):

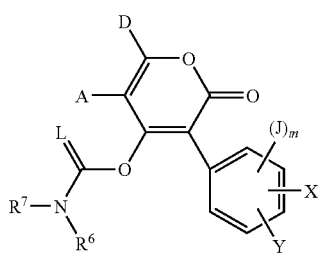

in which

A, D, E, J, L, m, M, X, Y, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-5-a) to (I-5-g) result if CKE represents group (5)

(I-5-a):

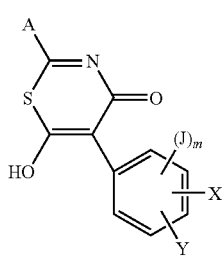

(I-5-b):

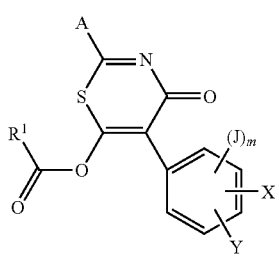

(I-5-c):

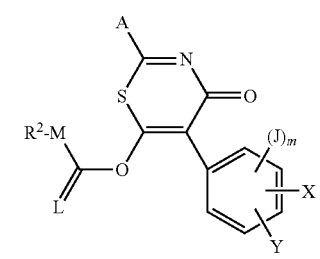

-continued (1-5-d):
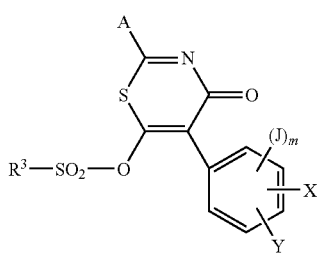

(1-5-e):
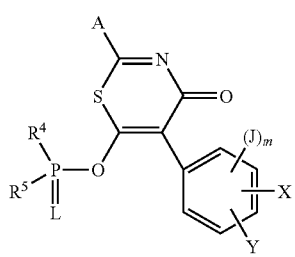

(1-5-f):
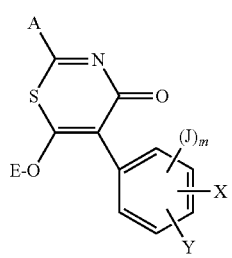

(1-5-g):
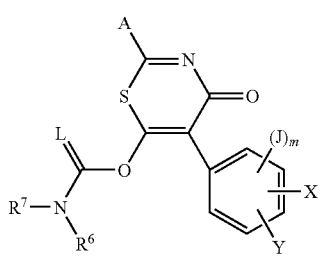

in which
A, E, J, L, m, M, X, Y, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B)

(I-6-A)
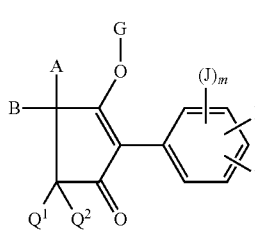

-continued (I-6-B)
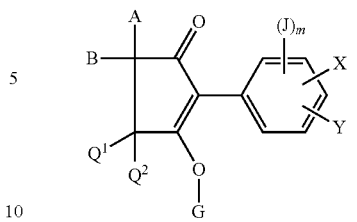

which is meant to be indicated by the dashed line in the formula (I)

The compounds of the formulae (I-6-A) and (I-6-B) can be present both as mixtures and in the form of their pure isomers. If appropriate, mixtures of the compounds of the formulae (I-6-A) and (I-6-B) can be separated by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric form.

Including the different meanings (a), (b), (c), (d), (e), (f) and (g) of group G, the following principal structures (I-6-a) to (I-6-g) result:

(I-6-a):
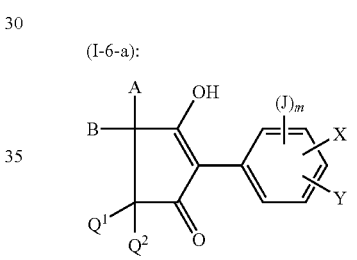

(I-6-b):
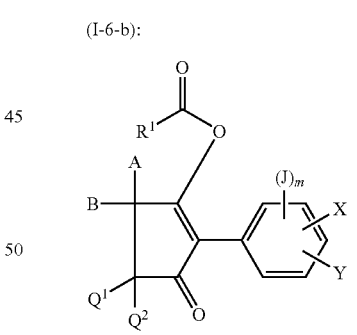

(I-6-c):
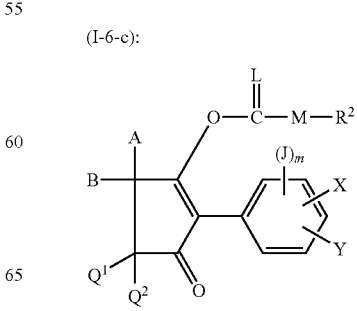

(I-6-d):

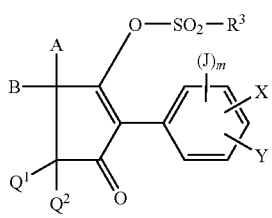

(I-6-e):

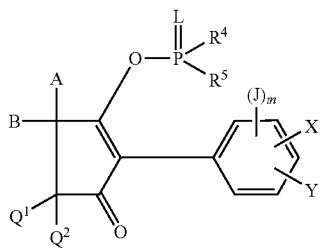

(I-6-f):

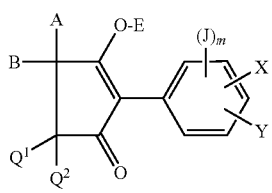

(I-6-g):

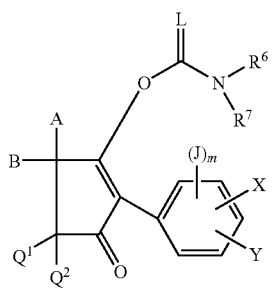

in which
A, B, J, $Q^1$, $Q^2$, E, L, m, M, X, Y, $R^1$, $R^2$, $R^3$, $R^4$, $R^5$, $R^6$ and $R^7$ are as defined above.

Depending on the position of the substituent G, the compounds of the formula (I-7) can be present in the two isomeric forms of the formulae (I-7-A) and (I-7-B), which is meant to be indicated by the dashed line in formula (I-7):

(I-7-A)

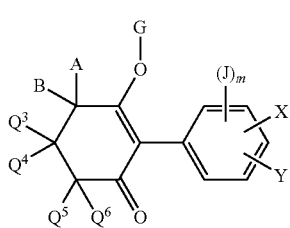

(I-7-B)

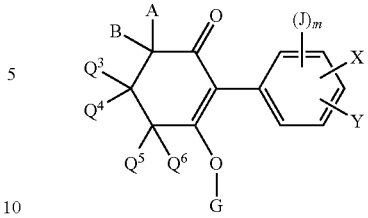

The compounds of the formulae (I-7-A) and (I-7-B) can be present both as mixtures and in the form of their pure isomers. If appropriate, mixtures of the compounds of the formulae (I-7-A) and (I-7-B) can be separated by physical methods, for example by chromatographic methods.

For reasons of clarity, hereinbelow in each case only one of the possible isomers is shown. This does not preclude that, if appropriate, the relevant compound may be present in the form of the isomer mixtures or the respective other isomeric form.

Including the different meanings (a), (b), (c), (d), (e), (f) and (g) of group G, the following principal structures (I-7-a) to (I-7-g) result:

(1-7-a):

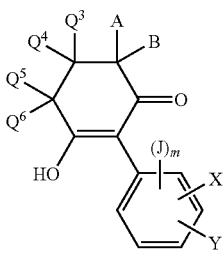

(1-7-b):

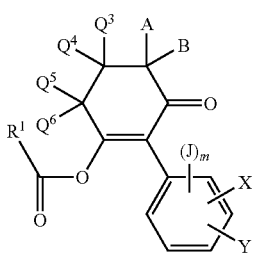

(1-7-c):

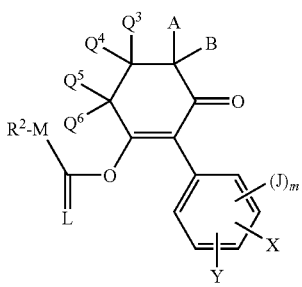

(1-7-d):

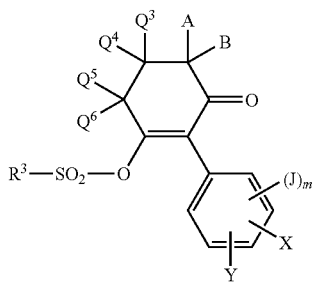

(1-7-e):

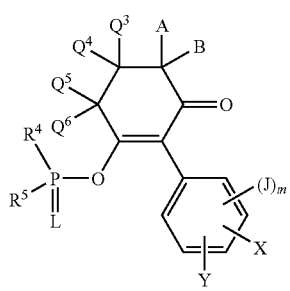

(1-7-f):

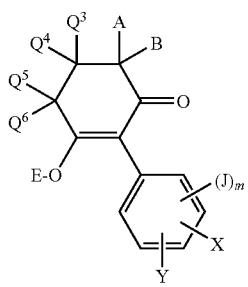

(1-7-g):

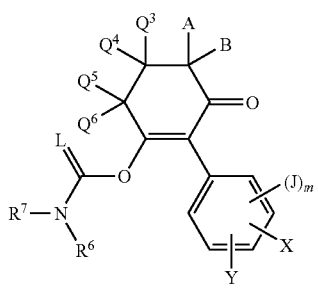

in which
A, B, J, E, L, m, M, $Q^3$, $Q^4$, $Q^5$, $Q^6$, X, Y, $R^1$, $R^2$, $R^3$, $R^4$, $R^5$, $R^6$ and $R^7$ are as defined above.

Depending on the position of the substituent G, the compounds of the formula (I-8) can be present in the two isomeric formulae (I-8-A) and (I-8-B)

(I-8-A)

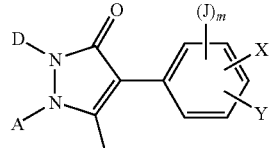

(I-8-B)

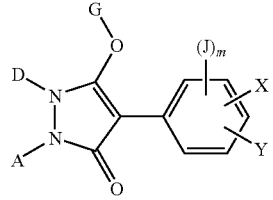

which is meant to be indicated by the dashed line in the formula (I-8).

The compounds of the formulae (I-8-A) and (I-8-B) can be present both as mixtures and in the form of their pure isomers. If appropriate, mixtures of the compounds of the formulae (I-8-A) and (I-8-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric form.

Including the different meanings (a), (b), (c), (d), (e), (f) and (g) of group G, the following principal structures (I-8-a) to (I-8-g) result if CKE represents group (8)

(I-8-a):

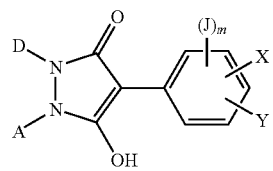

(I-8-b):

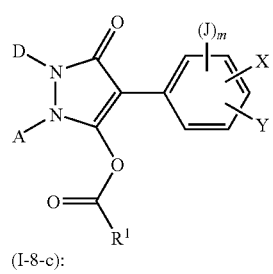

(I-8-c):

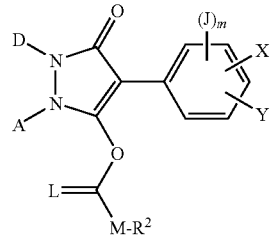

(I-8-d):

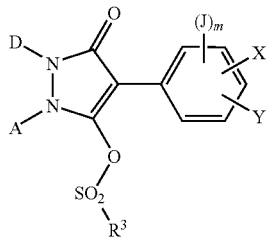

(I-8-e):

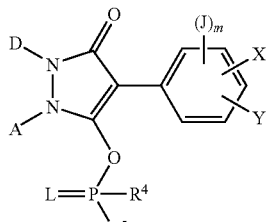

(I-8-f):

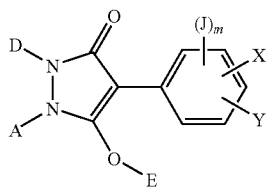

(I-8-g):

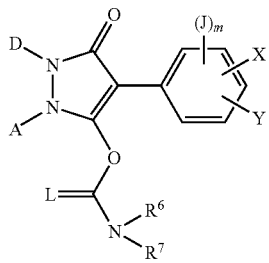

in which

A, D, E, J, L, M, m, X, Y, $R^1$, $R^2$, $R^3$, $R^4$, $R^5$, $R^6$ and $R^7$ are as defined above.

Depending on the position of the substituent G, the compounds of the formula (I-9) can be present in the two isomeric forms of the formulae (I-9-A) and (I-9-B)

(I-9-A)

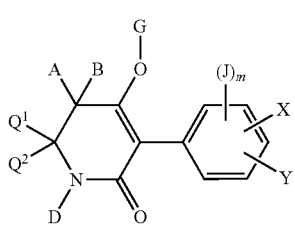

(I-9-B)

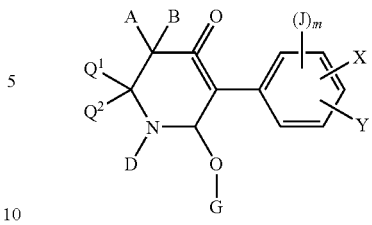

which is meant to be indicated by the dashed line in the formula (I-9).

The compounds of the formulae (I-9-A) and (I-9-B) can be present both as mixtures and in the form of their pure isomers. If appropriate, mixtures of the compounds of the formulae (I-9-A) and (I-9-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric form.

Including the different meanings (a), (b), (c), (d), (e), (f) and (g) of group G, the following principal structures (I-9-a) to (I-9-g) result if CKE represents group (9)

(1-9-a):

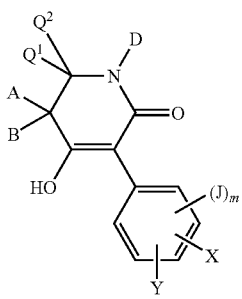

(1-9-b):

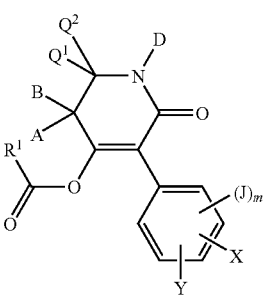

(1-9-c):

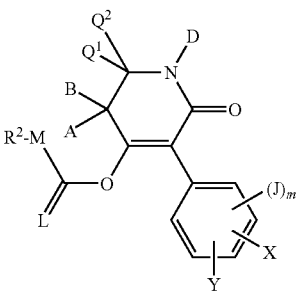

(1-9-d):

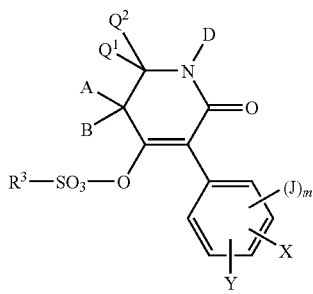

(1-9-e):

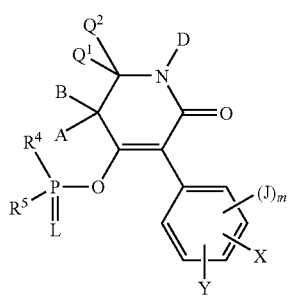

(1-9-f):

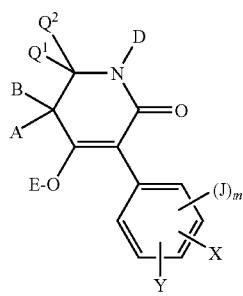

(1-9-g):

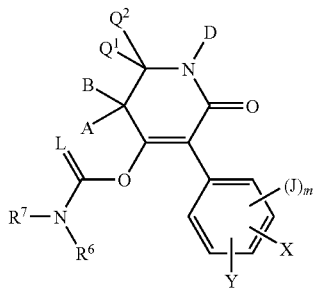

in which
A, B, D, E, J, L, m, M, $Q^1$, $Q^2$, X, Y, $R^1$, $R^2$, $R^3$, $R^4$, $R^5$, $R^6$ and $R^7$ are as defined above.

Depending on the position of the substituent G, the compounds of the formula (I-10) can be present in the two isomeric forms of the formulae (I-10-A) and (I-10-B)

(I-10-A)

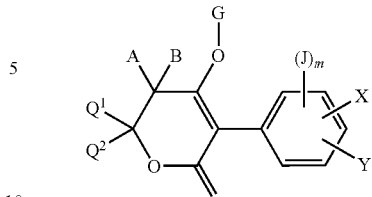

(I-10-B)

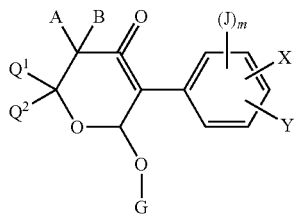

which is meant to be indicated by the dashed line in formula (I-10).

The compounds of the formulae (I-10-A) and (I-10-B) can be present both as mixtures and in the form of their pure isomers. If appropriate, mixtures of the compounds of the formulae (I-10-A) and (I-10-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric form.

Including the different meanings (a), (b), (c), (d), (e), (f) and (g) of group G, the following principal structures (I-10-a) to (I-10-g) result if CKE represents group (10)

(1-10-a):

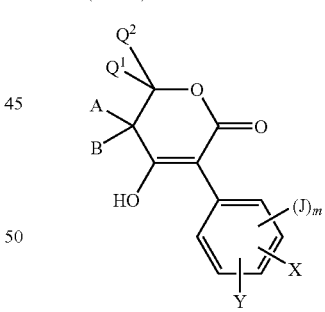

(1-10-b):

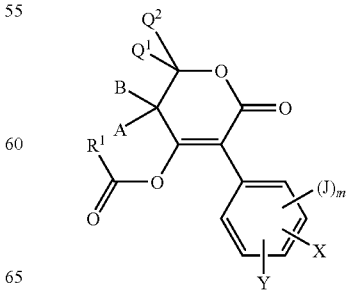

-continued (1-10-c):

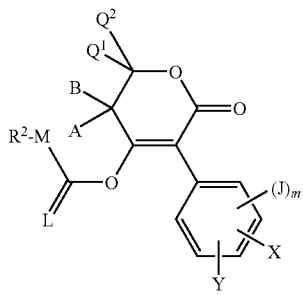

(1-10-d):

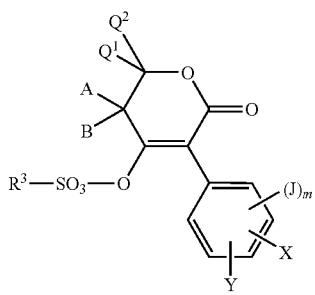

(1-10-e):

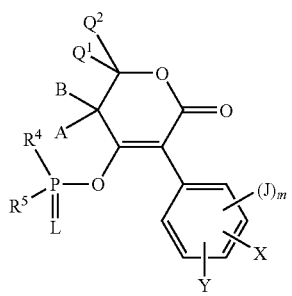

(1-10-f):

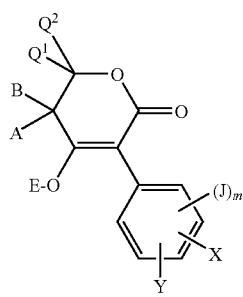

(1-10-g):

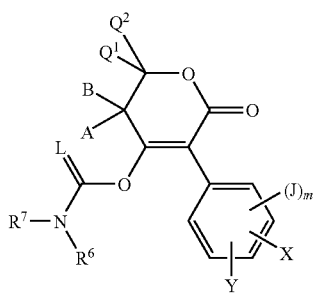

in which
A, B, E, L, m, M, $Q^1$, $Q^2$, X, Y, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) Substituted 3-phenylpyrrolidine-2,4-diones or their enols of the formula (I-1-a)

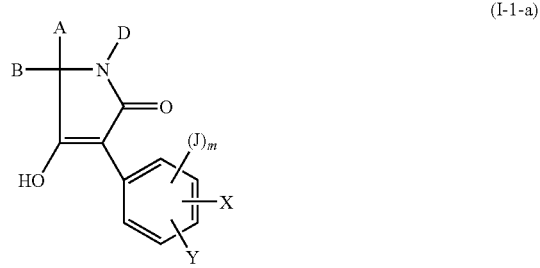

(I-1-a)

in which
A, B, D, J, m, X and Y are as defined above
are obtained when
N-acylamino acid esters of the formula (II)

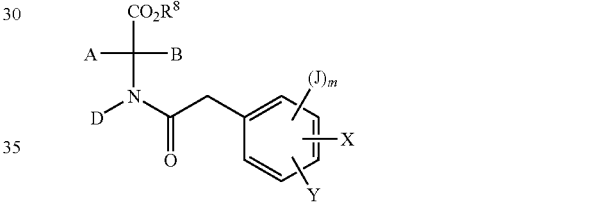

(II)

in which
A, B, D, J, m, X and Y are as defined above
and
$R^8$ represents alkyl (preferably $C_1$-$C_6$-alkyl)
are condensed intramolecularly in the presence of a diluent and in the presence of a base.

(B) Furthermore, it has been found that substituted 3-phenyl-4-hydroxy-$\Delta^3$-dihydrofuranone derivatives of the formula (I-2-a)

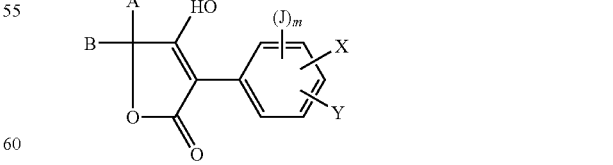

(I-2-a)

in which
A, B, J, m, X and Y are as defined above
are obtained when
carboxylic esters of the formula (III)

(III)

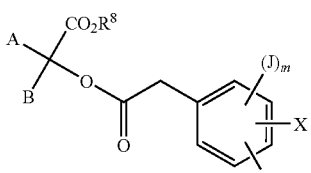

in which
A, B, J, m, X, Y and $R^8$ are as defined above
are condensed intramolecularly in the presence of a diluent and in the presence of a base.

(C) Furthermore, it has been found that substituted 3-phenyl-4-hydroxy-$\Delta^3$-dihydrothio-phenone derivatives of the formula (I-3-a)

(I-3-a)

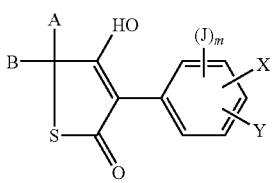

in which
A, B, J, m, X and Y are as defined above
are obtained when
β-ketocarboxylic acid esters of the formula (IV)

(IV)

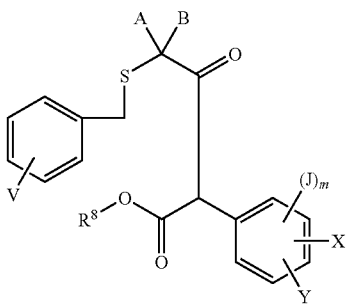

in which
A, B, J, m, X, Y and $R^8$ are as defined above and
V represents hydrogen, halogen, alkyl (preferably $C_1$-$C_6$-alkyl) or alkoxy (preferably $C_1$-$C_8$-alkoxy)
are cyclized intramolecularly, if appropriate in the presence of a diluent and in the presence of an acid.

(D) Furthermore, it has been found that the novel substituted 3-phenylpyrone derivatives of the formula (I-4-a)

(I-4-a)

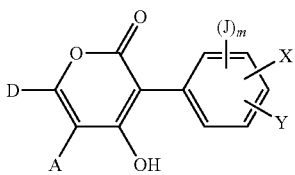

in which
A, D, J, m, X and Y are as defined above
are obtained when
carbonyl compounds of the formula (V)

(V)

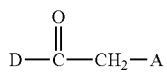

in which
A and D are as defined above
or their silylenol ethers of the formula (Va)

(Va)

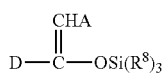

in which
A, D and $R^8$ are as defined above
are reacted with ketene acid halides of the formula (VI)

(VI)

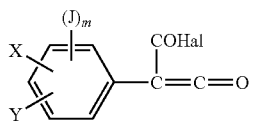

in which
J, m, X and Y are as defined above and
Hal represents halogen (preferably chlorine or bromine),
if appropriate in the presence of a diluent and if appropriate in the presence of an acid acceptor.

Furthermore, it has been found
(E) that the novel substituted phenyl-1,3-thiazine derivatives of the formula (I-5-a)

(I-5-a)

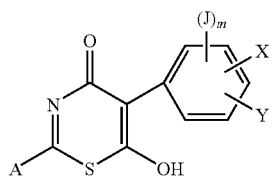

in which
A, J, m, X and Y are as defined above
are obtained when thioamides of the formula (VII)

(VII)

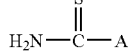

in which
A is as defined above
are reacted with ketene acid halides of the formula (VI)

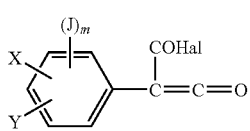

(VI)

in which
Hal, J, m, X and Y are as defined above,
if appropriate in the presence of a diluent and if appropriate in the presence of an acid acceptor.
Furthermore, it has been found
(F) that compounds of the formula (I-6-a)

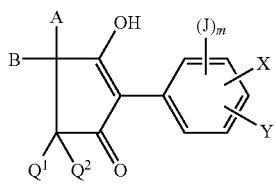

(I-6-a)

in which
A, B, $Q^1$, $Q^2$, J, m, X and Y are as defined above
are obtained when
ketocarboxylic esters of the formula (VIII)

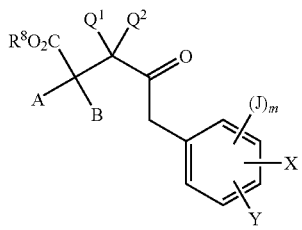

(VIII)

in which
A, B, $Q^1$, $Q^2$, J, m, X and Y are as defined above and
$R^8$ represents alkyl (in particular $C_1$-$C_8$-alkyl)
are cyclized intramolecularly, if appropriate in the presence of a diluent and in the presence of a base.
Moreover, it has been found
(G) that compounds of the formula (I-7-a)

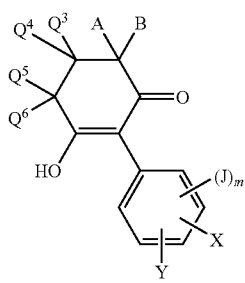

(I-7-a)

in which
A, B, J, m, $Q^3$, $Q^4$, $Q^5$, $Q^6$, X and Y are as defined above
are obtained when
6-aryl-5-ketohexanoic esters of the formula (IX)

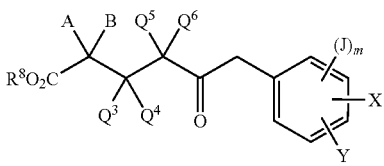

(IX)

in which
A, B, J, m, $Q^3$, $Q^4$, $Q^5$, $Q^6$, X and Y are as defined above
and
$R^8$ represents alkyl (preferably $C_1$-$C_6$-alkyl)
are condensed intramolecularly in the presence of a diluent and in the presence of a base.
(H) Furthermore, it has been found that the compounds of the formula (I-8-a)

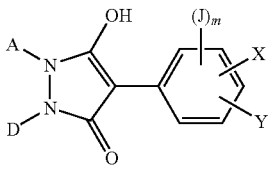

(I-8-a)

in which
A, D, J, m, X and Y are as defined above
are obtained when
compounds of the formula (X)

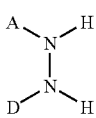

(X)

in which
A and D are as defined above
α) are reacted with compounds of the formula (VI)

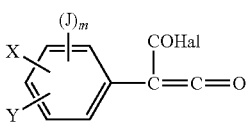

(VI)

in which
Hal, m, X, Y and J are as defined above,
if appropriate in the presence of a diluent and if appropriate in the presence of an acid acceptor, or
β) are reacted with compounds of the formula (XI)

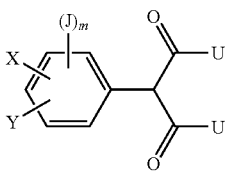

(XI)

in which
J, m, X and Y are as defined above
and U represents $NH_2$ or $O—R^8$, where $R^8$ is as defined above,
if appropriate in the presence of a diluent and if appropriate in the presence of a base, or
γ) are reacted with compounds of the formula (XII)

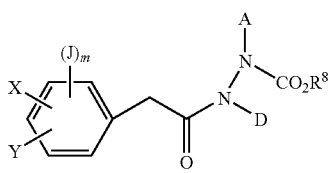
(XII)

in which
A, D, J, m, X, Y and $R^8$ are as defined above,
if appropriate in the presence of a diluent and if appropriate in the presence of a base.

Moreover, it has been found that the novel compounds of the formula (I) are obtained by one of the processes described below:
(I) Substituted tetrahydropyridine-2,4-diones or their enols of the formula (I-9-a)

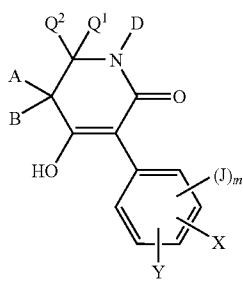
(I-9-a)

in which
A, B, D, J, m, $Q^1$, $Q^2$, X and Y are as defined above
are obtained when
N-acylamino acid esters of the formula (XIII)

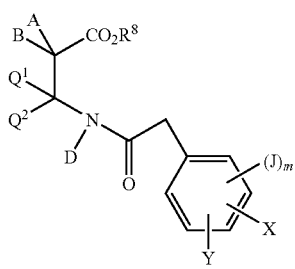
(XIII)

in which
A, B, D, J, m, $Q^1$, $Q^2$, X and Y are as defined above and
$R^8$ represents alkyl (preferably $C_1$-$C_6$-alkyl)
are condensed intramolecularly in the presence of a diluent and in the presence of a base.

Furthermore, it has been found
(J) that substituted 5,6-dihydropyrones of the formula (I-10-a)

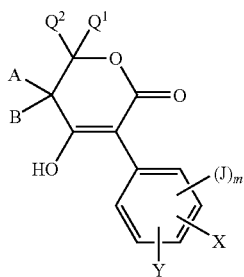
(I-10-a)

in which
A, B, J, m, $Q^1$, $Q^2$, X and Y are as defined above
are obtained when
O-acylhydroxycarboxylic esters of the formula (XIV)

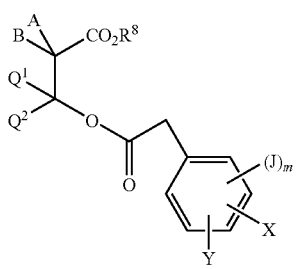
(XIV)

in which
A, B, J, m, $Q^1$, $Q^2$, X and Y are as defined above
and
$R^8$ represents alkyl (preferably $C_1$-$C_6$-alkyl)
are condensed intramolecularly in the presence of a diluent and in the presence of a base.

Moreover, it has been found
(K) that the compounds of the formulae (I-1-b) to (I-10-b) shown above in which A, B, D, J, m, $Q^1$, $Q^2$, $Q^3$, $Q^4$, $Q^5$, $Q^6$, $R^1$, X and Y are as defined above are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case reacted
(α) with acid halides of the formula (XV)

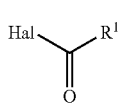
(XV)

in which
$R^1$ is as defined above and
Hal represents halogen (in particular chlorine or bromine)
or
(β) with carboxylic anhydrides of the formula (XVI)

$R^1$—CO—O—CO—$R^1$ (XVI)

in which
$R^1$ is as defined above,
if appropriate in the presence of a diluent and if appropriate in the presence of an acid binder;
(L) that the compounds of the formulae (I-1-c) to (I-10-c) shown above in which A, B, D, J, m, $Q^1$, $Q^2$, $Q^3$, $Q^4$, $Q^5$, $Q^6$, $R^2$, M, X and Y are as defined above and L represents oxygen are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case
reacted with chloroformic esters or chloroformic thioesters of the formula (XVII)

  (XVII)

in which
$R^2$ and M are as defined above,
if appropriate in the presence of a diluent and if appropriate in the presence of an acid binder;
(M) that compounds of the formulae (I-1-c) to (I-10-c) shown above in which A, B, D, J, m, $Q^1$, $Q^2$, $Q^3$, $Q^4$, $Q^5$, $Q^6$, $R^2$, M, X and Y are as defined above and L represents sulphur are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case reacted with chloromonothioformic esters or chlorodithioformic esters of the formula (XVIII)

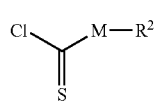 (XVIII)

in which
M and $R^2$ are as defined above,
if appropriate in the presence of a diluent and if appropriate in the presence of an acid binder,
and
(N) that compounds of the formulae (I-1-d) to (I-10-d) shown above in which A, B, D, J, m, $Q^1$, $Q^2$, $Q^3$, $Q^4$, $Q^5$, $Q^6$, $R^3$, X and Y are as defined above are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case
reacted with sulphonyl chlorides of the formula (XIX)

 (XIX)

in which
$R^3$ is as defined above,
if appropriate in the presence of a diluent and if appropriate in the presence of an acid binder,
(O) that compounds of the formulae (I-1-e) to (I-10-e) shown above in which A, B, D, J, m, L, $Q^1$, $Q^2$, $Q^3$, $Q^4$, $Q^5$, $Q^6$, $R^4$, $R^5$, X and Y are as defined above are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case
reacted with phosphorus compounds of the formula (XX)

 (XX)

in which
L, $R^4$ and $R^5$ are as defined above and
Hal represents halogen (in particular chlorine or bromine),
if appropriate in the presence of a diluent and if appropriate in the presence of an acid binder,
(P) that compounds of the formulae (I-1-f) to (I-10-f) shown above in which A, B, D, E, J, m, $Q^1$, $Q^2$, $Q^3$, $Q^4$, $Q^5$, $Q^6$, X and Y are as defined above are obtained when compounds of the formulae (I-1-a) to (I-10-a) in which A, B, D, J, m, $Q^1$, $Q^2$, $Q^3$, $Q^4$, $Q^5$, $Q^6$, X and Y are as defined above are in each case
reacted with metal compounds or amines of the formulae (XXI) or (XXII)

  (XXI)

  (XXII)

in which
Me represents a mono- or divalent metal (preferably an alkali metal or alkaline earth metal, such as lithium, sodium, potassium, magnesium or calcium), or represents an ammonium ion

t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent,
(Q) that compounds of the formulae (I-1-g) to (I-10-g) shown above in which A, B, D, J, m, L, $Q^1$, $Q^2$, $Q^3$, $Q^4$, $Q^5$, $Q^6$, $R^6$, $R^7$, X and Y are as defined above are obtained when compounds of the formulae (I-1-a) to (I-10-a) shown above in which A, B, D, J, m, $Q^1$, $Q^2$, $Q^3$, $Q^4$, $Q^5$, $Q^6$, X and Y are as defined above are in each case
(α) reacted with isocyanates or isothiocyanates of the formula (XXIII)

 (XXIII)

in which
$R^6$ and L are as defined above
if appropriate in the presence of a diluent and if appropriate in the presence of a catalyst, or
(β) reacted with carbamoyl chlorides or thiocarbamoyl chlorides of the formulae (XXIV)

 (XXIV)

in which
L, $R^6$ and $R^7$ are as defined above,
if appropriate in the presence of a diluent and if appropriate in the presence of an acid binder,
(R) that compounds of the formulae (I-1-a) to (I-10-g) shown above in which A, B, D, C, J, m, $Q^1$, $Q^2$, $Q^3$, $Q^4$, $Q^5$, $Q^6$, X and Y are as defined above are obtained when compounds of the formulae (I-1') to (I-10'-g) in which A, B, D, J, m, $Q^1$, $Q^2$, $Q^3$, $Q^4$, $Q^5$, $Q^6$, X and Y are as defined above and J' preferably represents bromine or iodine

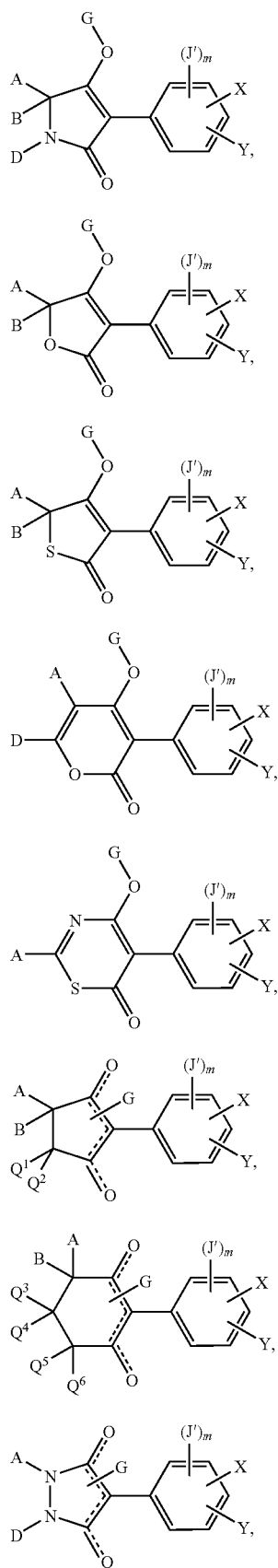

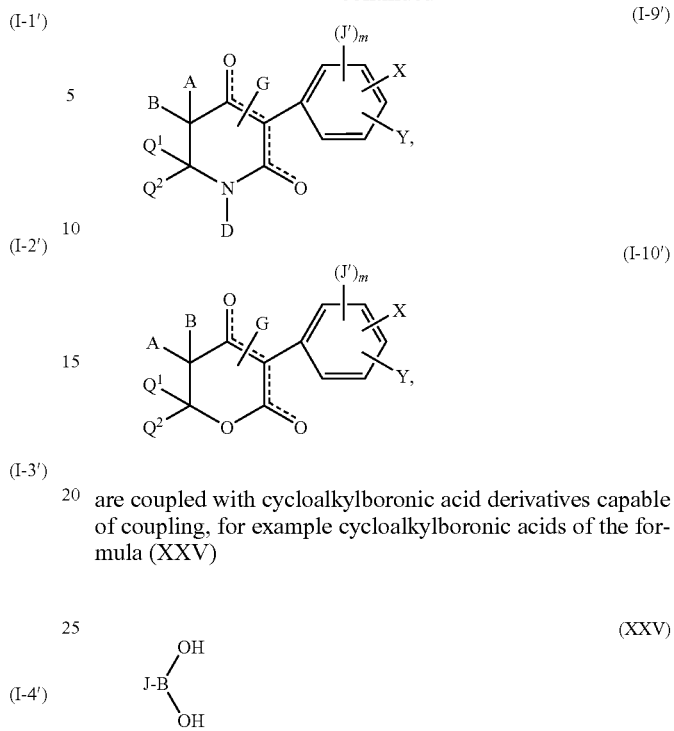

are coupled with cycloalkylboronic acid derivatives capable of coupling, for example cycloalkylboronic acids of the formula (XXV)

or their esters, in the presence of a solvent, in the presence of a catalyst (for example Pd complexes) and in the presence of a base (for example sodium carbonate, potassium dihydrogenphosphate).

Furthermore, it has been found that the novel compounds of the formula (I) have very good activity as pesticides, preferably as insecticides and/or acaricides and/or herbicides.

Surprisingly, it has now also been found that certain substituted cyclic ketoenols, when employed together with the crop plant compatibility-improving compounds (safeners/antidotes) described later on, are extremely good at preventing damage to the crop plants and can be used with particular advantage as broad-spectrum combination products for the selective control of unwanted plants in crops of useful plants, such as, for example, in cereals, but also in corn, soyabeans and rice.

The invention also provides selective herbicidal compositions comprising an effective amount of an active compound combination comprising, as components, (a') at least one substituted cyclic ketoenol of the formula (I) in which CKE, J, m, X and Y are as defined above and (b') at least one crop plant compatibility-improving compound from the following group of compounds:

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxy-acetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1- methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl -1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloro-acetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl -2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro -quinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxy-malonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxy-benzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl) -amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl) -phenyl]-3,3-dimethylurea, N-(2-methoxy-5-methylbenzoyl)-4-(cyclopropylaminocarbonyl)-benzenesulphonamide,
and/or one of the following compounds, defined by general formulae, of the general formula (IIa)

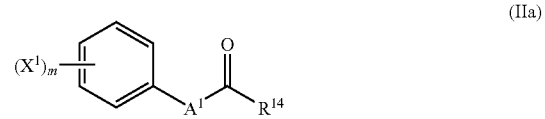

or of the general formula (IIb)

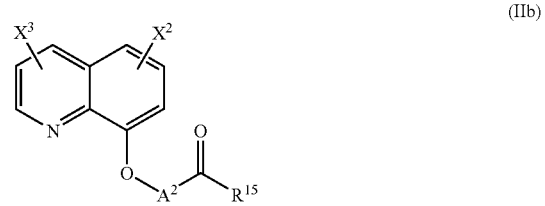

or of the formula (IIc)

where
m represents a number 0, 1, 2, 3, 4 or 5,
$A^1$ represents one of the divalent heterocyclic groupings shown below

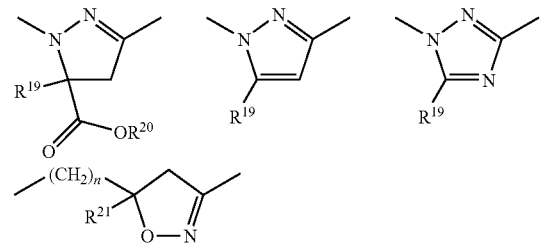

n represents a number 0, 1, 2, 3, 4 or 5,
$A^2$ represents optionally $C_1$-$C_4$-alkyl- and/or $C_1$-$C_4$-alkoxycarbonyl- and/or $C_1$-$C_4$-alkenyloxy-carbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl) amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl) amino,
$R^{16}$ represents in each case optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$- alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

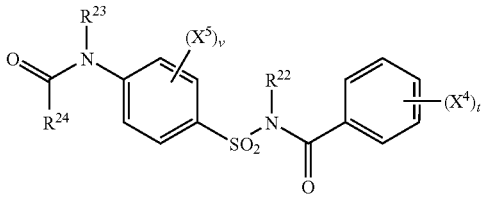

(IId)

or of the general formula (IIe)

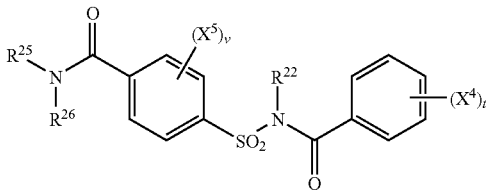

(IIe)

where
t represents a number 0, 1, 2, 3, 4 or 5,
V represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae given above and below are illustrated below:

J preferably represents $C_3$-$C_8$-cycloalkyl which may optionally be interrupted by oxygen and which may optionally be substituted by halogen, $C_1$-$C_6$-alkyl, $C_1$-$C_6$-alkoxy, $C_1$-$C_6$-haloalkyl or optionally by $C_1$-$C_4$-alkyl-, $C_1$-$C_4$-alkoxy-, halogen-, $C_1$-$C_4$-haloalkyl-, $C_1$-$C_4$-haloalkoxy-substituted phenyl or $C_3$-$C_6$-cycloalkyl, X preferably represents hydrogen, halogen, $C_1$-$C_6$-alkyl, $C_1$-$C_4$-haloalkyl, $C_1$-$C_6$-alkoxy or $C_1$-$C_4$-haloalkoxy, Y preferably represents hydrogen, $C_1$-$C_6$-alkyl, $C_1$-$C_4$-haloalkyl, halogen, $C_1$-$C_6$-alkoxy or $C_1$-$C_4$-haloalkoxy, m preferably represents a number 1, 2 or 3, with the proviso that at least one of the radicals J, X or Y is located in the 2-position of the phenyl radical and is not hydrogen, CKE preferably represents one of the groups

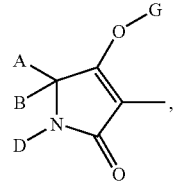

(1)

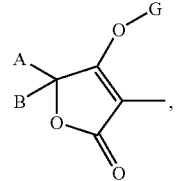

(2)

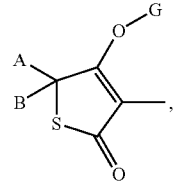

(3)

-continued (4)
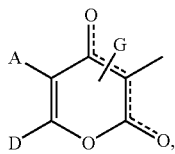

(5)
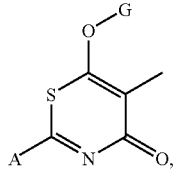

(6)
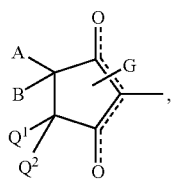

(7)
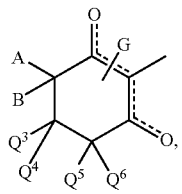

(8)
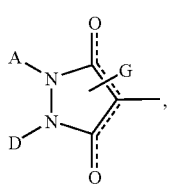

(9)
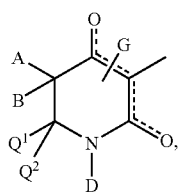

(10)
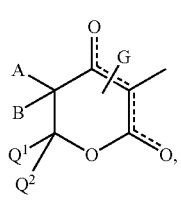

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 or 6 ring atoms (for example, furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B preferably represents hydrogen, $C_1$-$C_{12}$-alkyl or $C_1$-$C_8$-alkoxy-$C_1$-$C_6$-alkyl or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_9$-alkyl, $C_3$-$C_{10}$-cycloalkyl, $C_1$-$C_8$-haloalkyl, $C_1$-$C_8$-alkoxy, $C_1$-$C_4$-alkoxy-$C_1$-$C_4$-alkoxy, $C_1$-$C_8$-alkylthio, halogen or phenyl or A, B and the carbon atom to which they are attached preferably represent $C_3$-$C_6$-cycloalkyl which is substituted by an alkylenediyl group or by an alkylenedixyl group or by an alkylenedithioyl group which optionally contains one or two not directly adjacent oxygen and/or sulphur atoms and which is optionally substituted by $C_1$-$C_4$-alkyl, which group, together with the carbon atom to which it is attached, forms a further five- to eight-membered ring, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted, $C_3$-$C_8$-cycloalkyl, in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1) A and D in this case together with the atoms to which they are attached represent, for example, the groups AD-1 to AD-10 mentioned further below) that may contain oxygen or sulphur or which optionally contain one of the following groups

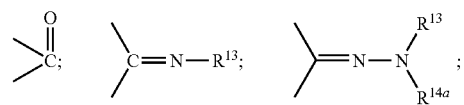

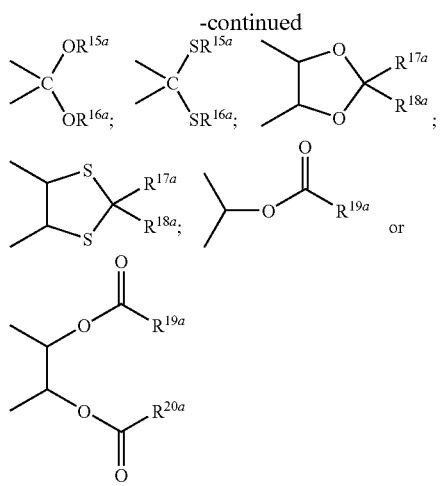

or

A and Q¹ together preferably represent $C_3$-$C_6$-alkanediyl or $C_4$-$C_6$-alkenediyl, each of which is optionally mono- or disubstituted by identical or different substituents from the group consisting of halogen; hydroxyl; $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogen substituents; and benzyloxy or phenyl, each of which is optionally mono- to trisubstituted by identical or different substituents from the group consisting of halogen, $C_1$-$C_6$-alkyl and $C_1$-$C_6$-alkoxy; which $C_3$-$C_6$-alkanediyl or $C_4$-$C_6$-alkenediyl furthermore optionally contains one of the groups below

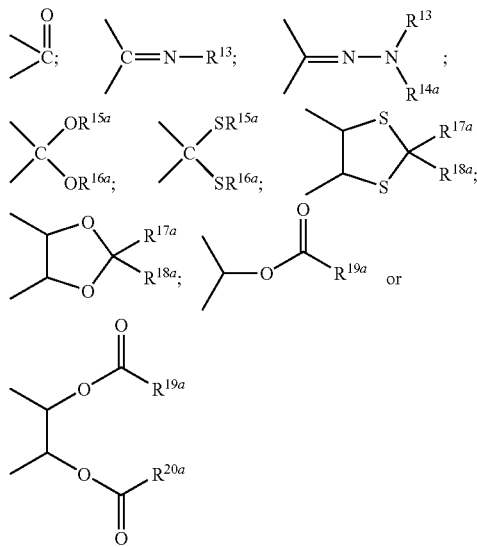

or is bridged by a $C_1$-$C_2$-alkanediyl group or by an oxygen atom or

D and Q¹ together preferably represent $C_3$-$C_6$-alkanediyl which is in each case optionally mono- or disubstituted by identical or different $C_1$-$C_4$-alkyl or $C_1$-$C_4$-alkoxy and is optionally interrupted by an oxygen atom or Q¹ preferably represents hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-haloalkyl- or $C_1$-$C_4$-alkoxy-substituted $C_3$-$C_8$-cycloalkyl in which optionally one methylene group is replaced by oxygen or sulphur or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl or Q², Q⁴, Q⁵ and Q⁶ independently of one another preferably represent hydrogen or $C_1$-$C_4$-alkyl, Q³ preferably represents hydrogen, $C_1$-$C_6$-alkyl, $C_1$-$C_6$-alkoxy-$C_1$-$C_2$-alkyl, $C_1$-$C_6$-alkyl-thio-$C_1$-$C_2$-alkyl, optionally $C_1$-$C_4$-alkyl- or $C_1$-$C_4$-alkoxy-substituted $C_3$-$C_8$-cycloalkyl in which optionally one methylene group is replaced by oxygen or sulphur or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, Q¹ and Q² together with the carbon atom to which they are attached preferably represent optionally $C_1$-$C_6$-alkyl-, $C_1$-$C_6$-alkoxy- or $C_1$-$C_2$-haloalkyl-substituted $C_3$-$C_7$-cycloalkyl in which optionally one ring member is replaced by oxygen or sulphur, or Q³ and Q⁴ together with the carbon atom to which they are attached preferably represent an optionally $C_1$-$C_4$-alkyl-, $C_1$-$C_4$-alkoxy- or $C_1$-$C_2$-haloalkyl-substituted $C_3$-$C_7$-ring in which optionally one ring member is replaced by oxygen or sulphur, G preferably represents hydrogen (a) or represents one of the groups

 (b)

 (c)

 (d)

 (e)

E or (f)

 (g)

in particular (a), (b), (c) or (g), in which

E represents a metal ion equivalent or an ammonium ion,
L represents oxygen or sulphur and
M represents oxygen or sulphur,
R¹ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio -$C_1$-$C_8$-alkyl, poly-$C_1$-$C_8$-alkoxy -$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, preferably represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio - or $C_1$-$C_6$-alkylsulphonyl-substituted phenyl, preferably represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, preferably represents optionally halogen- or $C_1$-$C_6$-alkyl-substituted 5- or 6-membered hetaryl (for example pyrazolyl, thiazolyl, pyridyl, pyrimidyl, furanyl or thienyl), preferably represents optionally halogen- or $C_1$-$C_6$-alkyl-substituted phenoxy-$C_1$-$C_6$-alkyl or preferably represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, preferably represents optionally halogen-, $C_1$-$C_6$-alkyl- or $C_1$-$C_6$-alkoxy-substituted $C_3$-$C_8$-cycloalkyl or preferably represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur, $R^{13}$ preferably represents hydrogen, preferably represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14a}$ preferably represents hydrogen or $C_1$-$C_8$-alkyl or $R^{13}$ and $R^{14a}$ together preferably represent $C_4$-$C_6$-alkanediyl, $R^{15a}$ and $R^{16a}$ are identical or different and preferably represent $C_1$-$C_6$-alkyl or $R^{15a}$ and $R^{16a}$ together preferably represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine.

J particularly preferably represents $C_3$-$C_6$-cycloalkyl which is optionally interrupted by an oxygen atom and is optionally mono- or disubstituted by fluorine, chlorine, $C_1$-$C_4$-alkyl, $C_3$-$C_6$-cycloalkyl, $C_1$-$C_4$-alkoxy or $C_1$-$C_2$-haloalkyl, X particularly preferably represents hydrogen, fluorine, chlorine, bromine, iodine, $C_1$-$C_4$-alkyl, trifluoromethyl, $C_1$-$C_4$-alkoxy, difluoromethoxy or trifluoromethoxy, Y particularly preferably represents hydrogen, fluorine, chlorine, bromine, iodine, $C_1$-$C_4$-alkyl, trifluoromethyl, $C_1$-$C_4$-alkoxy, difluoromethoxy or trifluoromethoxy, m particularly preferably represents a number 1 or 2 with the proviso that at least one of the radicals J, X or Y is located in the 2-position of the phenyl radical and is not hydrogen, CKE particularly preferably represents one of the groups

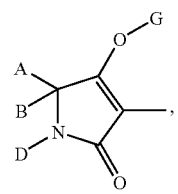

(1)

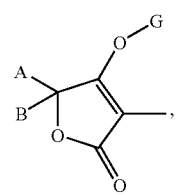

(2)

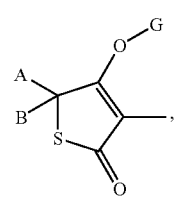

(3)

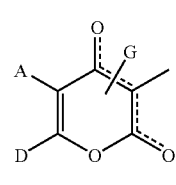

(4)

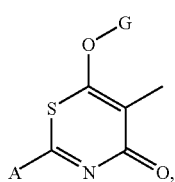
(5)

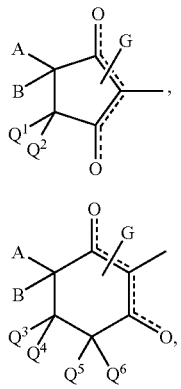
(6)

(7)

(8)

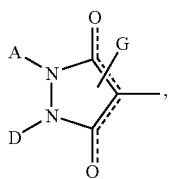
(9)

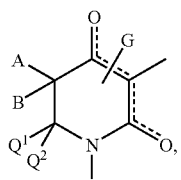
(10)

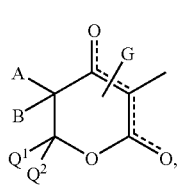

A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by $C_1$-$C_2$-alkyl or $C_1$-$C_2$-alkoxy or (but not in the case of the compounds of the formulae (I-3), (I-4), (I-6) and (I-7)) represents phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxy-$C_1$-$C_2$-alkyl or A, B and the carbon atom to which they are attached particularly preferably represent saturated or unsaturated $C_5$-$C_7$-cycloalkyl in which optionally one ring member is replaced by oxygen or sulphur and which is optionally mono- or disubstituted by $C_1$-$C_6$-alkyl, trifluoromethyl, $C_1$-$C_6$-alkoxy or $C_1$-$C_3$-alkoxy-$C_1$-$C_3$-alkoxy, with the proviso that in this case $Q^3$ particularly preferably represents hydrogen or methyl or A, B and the carbon atom to which they are attached particularly preferably represent $C_5$-$C_6$-cycloalkyl which is substituted by an alkylenediyl group or by an alkylenedioxyl group or by an alkylenedithiol group which optionally contains one or two not directly adjacent oxygen or sulphur atoms and which is optionally substituted by methyl or ethyl, which group together with the carbon atom to which it is attached forms a further five- or six-membered ring, with the proviso that $Q^3$ in this case particularly preferably represents hydrogen or methyl, or A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, with the proviso that $Q^3$ in this case particularly preferably represents hydrogen or methyl, D represents hydrogen, represents $C_1$-$C_6$-alkyl, $C_3$-$C_6$-alkenyl, $C_1$-$C_4$-alkoxy-$C_2$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl in which optionally one methylene group is replaced by oxygen or (but not in the case of the compounds of the formulae (I-1)) represents phenyl or pyridyl, each of which is optionally mono- or disubstituted by fluorine, chlorine, bromine, $C_1$-$C_4$-alkyl, $C_1$-$C_4$-haloalkyl, $C_1$-$C_4$-alkoxy or $C_1$-$C_4$-haloalkoxy, or A and D together particularly preferably represent optionally mono- or disubstituted $C_3$-$C_5$-alkanediyl in which one methylene group may be replaced by a carbonyl group (but not in the case of the compounds of the formula (I-1)), oxygen or sulphur, possible substituents being $C_1$-$C_2$-alkyl or $C_1$-$C_2$-alkoxy, or A and D (in the case of the compounds of the formula (I-1)) together with the atoms to which they are attached represent one of the groups AD-1 to AD-10:

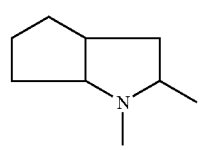
AD-1

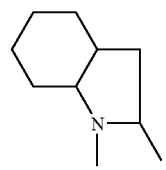
AD-2

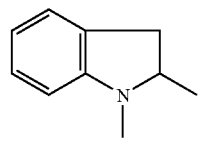
AD-3

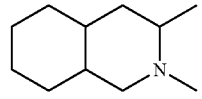
AD-4

AD-5 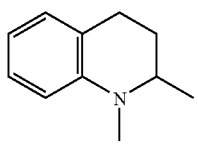

AD-6 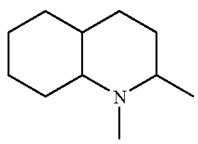

AD-7 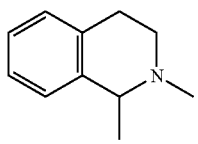

AD-8 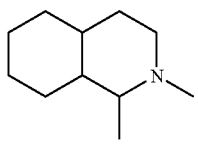

AD-9 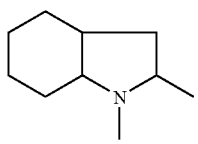

AD-10 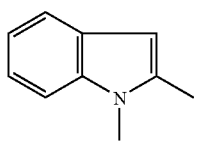

or
- A and $Q^1$ together particularly preferably represent $C_3$-$C_4$-alkanediyl which is in each case optionally mono- or disubstituted by identical or different substituents selected from the group consisting of $C_1$-$C_2$-alkyl and $C_1$-$C_2$-alkoxy or
- D and $Q^1$ together particularly preferably represent $C_3$-$C_4$-alkanediyl which is optionally interrupted by an oxygen atom, or
- $Q^1$ particularly preferably represents hydrogen, $C_1$-$C_4$-alkyl, $C_1$-$C_4$-alkoxy-$C_1$-$C_2$-alkyl or optionally methyl- or methoxy-substituted $C_3$-$C_6$-cycloalkyl in which optionally one methylene group is replaced by oxygen,
- $Q^2$ particularly preferably represents hydrogen, methyl or ethyl,
- $Q^4$, $Q^5$ and $Q^6$ independently of one another particularly preferably represent hydrogen or $C_1$-$C_3$-alkyl,
- $Q^3$ particularly preferably represents hydrogen, $C_1$-$C_4$-alkyl, or $C_3$-$C_6$-cycloalkyl which is optionally mono- or disubstituted by methyl or methoxy,
- $Q^1$ and $Q^2$ together with the carbon to which they attached particularly preferably represent optionally $C_1$-$C_4$-alkyl- or $C_1$-$C_4$-alkoxy-substituted saturated $C_5$-$C_6$-cycloalkyl in which optionally one ring member is replaced by oxygen, or
- $Q^3$ and $Q^4$ together with the carbon to which they are attached particularly preferably represent an optionally $C_1$-$C_2$-alkyl- or $C_1$-$C_2$-alkoxy-substituted saturated $C_5$-$C_6$-ring in which optionally one ring member is replaced by oxygen or sulphur, with the proviso that in this case A particularly preferably represents hydrogen or methyl, G particularly preferably represents hydrogen (a) or represents one of the groups (b) 

(c) 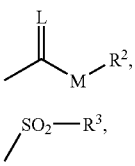

(d) 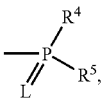

(e) 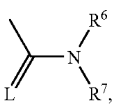

(f) E or (g)

in particular (a), (b), or (c), in which
E represents a metal ion equivalent or an ammonium ion,
L represents oxygen or sulphur
M represents oxygen or sulphur,
$R^1$ particularly preferably represents $C_1$-$C_8$-alkyl, $C_2$-$C_{18}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen,
particularly preferably represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy,
$R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
particularly preferably represents $C_3$-$C_6$-cycloalkyl which is optionally monosubstituted by $C_1$-$C_2$-alkyl or $C_1$-$C_2$-alkoxy or
particularly preferably represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy,
$R^3$ particularly preferably represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro,
$R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkyl-thio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent a $C_4$-$C_5$-alkylene radical which is optionally substituted by methyl or ethyl and in which optionally one methylene group is replaced by oxygen or sulphur.

In the radical definitions mentioned as being particularly preferred, halogen represents fluorine, chlorine and bromine, in particular fluorine and chlorine.

J very particularly preferably represents cyclopropyl, dicyclopropyl, cyclobutyl, cyclopentyl, cyclohexyl, oxetanyl, tetrahydrofurfuryl, tetrahydropyranyl, X very particularly preferably represents hydrogen, fluorine, chlorine, bromine, methyl, ethyl, propyl, methoxy or ethoxy, Y very particularly preferably represents hydrogen, chlorine, bromine, methyl, ethyl, propyl, trifluoromethyl, methoxy, ethoxy or trifluoromethoxy, m very particularly preferably represents the number 1 or 2, with the proviso that at least one of the radicals J, X or Y is located in the 2-position of the phenyl radical and is not hydrogen.

Here, the radicals J, X and Y having their very particularly preferred meanings, are very particularly preferably arranged in the following phenyl substitution patterns

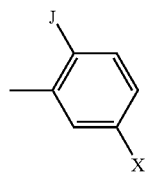
(A)

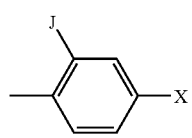
(B)

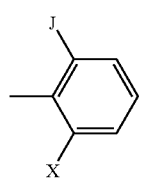
(C)

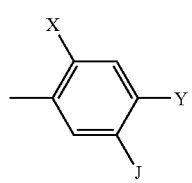
(D)

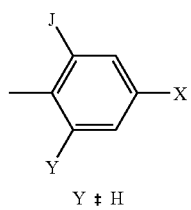
(E)

Y ≠ H

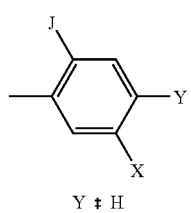
(F)

Y ≠ H

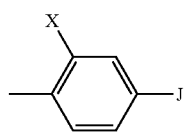
(G)

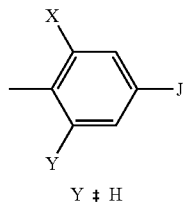
(H)

Y ≠ H

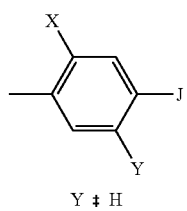
(I)

Y ≠ H

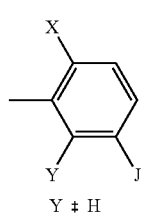
(J)

Y ≠ H

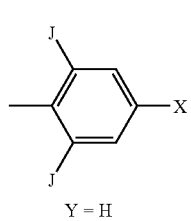
(K)

Y = H

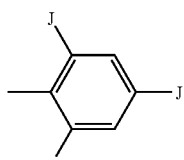

Y = H where only in the phenyl substitution patterns (B), (K) and (L), X may also represent hydrogen, CKE very particularly preferably represents one of the groups

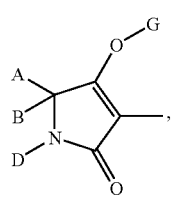 (1)

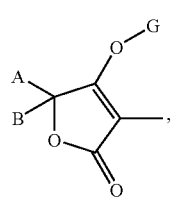 (2)

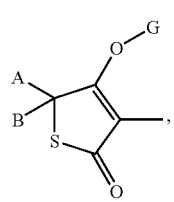 (3)

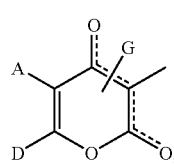 (4)

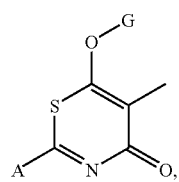 (5)

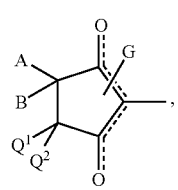 (6)

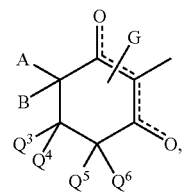 (7)

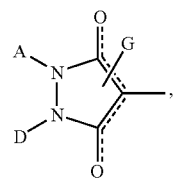 (8)

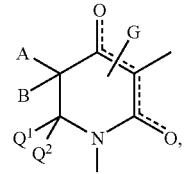 (9)

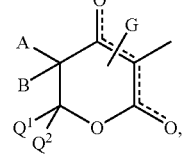 (10)

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl and, only in the case of the compounds of the formula (I-5) represents phenyl which is optionally mono- or disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl or ethyl, or A, B and the carbon atom to which they are attached very particularly preferably represents saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy, methoxyethoxy, butoxy, methoxymethyl or ethoxyethoxy, with the proviso that in this case $Q^3$ very particularly preferably represents hydrogen, or A, B and the carbon atom to which they are attached very particularly preferably represent $C_6$-cycloalkyl which is optionally substituted by an alkylenedioxyl group which contains two not directly adjacent oxygen atoms, with the proviso that in this case $Q^3$ very particularly preferably represents hydrogen, or A, B and the carbon atom to which they are attached very particularly preferably represents $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, with the proviso that in this case $Q^3$ very particularly preferably represents hydrogen, D very particularly preferably represents hydrogen, represents $C_1$-$C_4$-alkyl, $C_3$-$C_4$-alkenyl, $C_1$-$C_4$-alkoxy-$C_2$-$C_3$-alkyl, each of which is optionally mono- to trisubstituted by fluorine, represents cyclopropyl, cyclopentyl or cyclohexyl or (but not in the case of the compounds of the formulae (I-1)) represents phenyl or pyridyl, each of which is optionally monosubstituted by fluorine, chlorine, methyl, ethyl, n-propyl, isopropyl, methoxy, ethoxy or trifluoromethyl, or A and D together very particularly preferably represent $C_3$-$C_5$-alkanediyl which is optionally monosubstituted by methyl or methoxy and in which optionally one carbon atom is replaced by oxygen or sulphur or represents the group AD-1, A and $Q^1$ together very particularly preferably represent $C_3$-$C_4$-alkanediyl which is optionally mono- or disubstituted by methyl or methoxy or D and $Q^1$ together very particularly preferably represent $C_3$-$C_4$-alkanediyl, $Q^1$ very particularly preferably represents hydrogen, methyl, ethyl, propyl, isopropyl, cyclopropyl, cyclopentyl or cyclohexyl, $Q^2$ very particularly preferably represents hydrogen or methyl, $Q^4$, $Q^5$ and $Q^6$ independently of one another very particularly preferably represent hydrogen or methyl, $Q^3$ very particularly preferably represents hydrogen, methyl, ethyl or propyl, or $Q^1$ and $Q^2$ together with the carbon to which they are attached very particularly preferably represent saturated $C_5$-$C_6$-cycloalkyl which is optionally substituted by methyl, ethyl, propyl, isopropyl, methoxy, ethoxy, propoxy or butoxy and in which optionally one ring member is replaced by oxygen, or $Q^3$ and $Q^4$ together with the carbon to which they are attached very particularly preferably represent a saturated $C_5$-$C_6$-ring which is optionally monosubstituted by methyl or methoxy, with the proviso that in this case A very particularly preferably represents hydrogen, G very particularly preferably represents hydrogen (a) or represents one of the groups

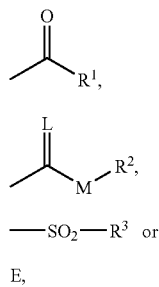 (b)

(c)

—SO$_2$—R$^3$ or (d)

E, (f)

in which

L represents oxygen or sulphur,

M represents oxygen or sulphur and

E represents an ammonium ion $R^1$ very particularly preferably represents $C_1$-$C_6$-alkyl, $C_2$-$C_{17}$-alkenyl, $C_1$-$C_2$-alkoxy -$C_1$-alkyl, $C_1$-$C_2$-alkylthio-$C_1$-alkyl, each of which is optionally monosubstituted by chlorine, or represents cyclopropyl or cyclohexyl, each of which is optionally monosubstituted by fluorine, chlorine, methyl or methoxy, very particularly preferably represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy -$C_2$-$C_3$-alkyl, each of which is optionally monosubstituted by fluorine, or represents phenyl or benzyl, $R^3$ very particularly preferably represents $C_1$-$C_8$-alkyl.

J most preferably represents cyclopropyl,

X most preferably represents chlorine, methyl or ethyl,

Y most preferably represents chlorine, methyl, ethyl or hydrogen, m most preferably represents the number 1 or 2, with the proviso that at least one of the radicals J, X or Y is located in the 2-position of the phenyl radical and is not hydrogen.

Here, the radicals J, X and Y, having their most preferred meanings, are especially preferably arranged in the following phenyl substitution patterns

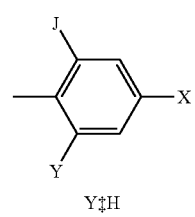 (E)

Y≠H

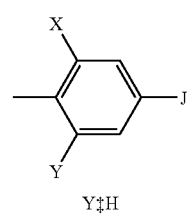 (H)

Y≠H

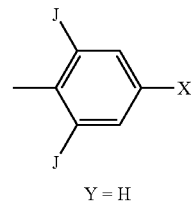 (K)

Y = H

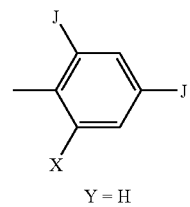 (L)

Y = H

CKE most preferably represents one of the groups (1)

[structure with A, B, D, N, O, O-G]

(2)

[structure with A, B, O, O-G]

(6)

[structure with A, B, Q¹, Q², O, G, O]

(8)

[structure with A, N, N, D, O, G, O]

A most preferably represents $C_1$-$C_4$-alkyl or cyclopropyl,
B most preferably represents hydrogen or methyl or
A, B and the carbon atom to which they are attached most preferably represent saturated $C_5$-$C_6$-cycloalkyl in which optionally one ring member is replaced by oxygen and which is optionally monosubstituted by methoxy, ethoxy, butoxy or methoxymethyl,
A, B and the carbon atom to which they are attached most preferably represent $C_6$-cycloalkyl which is optionally substituted by a $C_2$-$C_3$-alkylenedioxyl group having two not directly adjacent oxygen atoms,
D most preferably represents hydrogen or
A and D together most preferably represent $C_3$-$C_5$-alkanediyl,
A and $Q^1$ together most preferably represent $C_3$-$C_4$-alkanediyl,
$Q^2$ most preferably represents hydrogen,
G most preferably represents hydrogen (a) or represents one of the groups (b)

[structure: C(=O)-R¹]

(c)

[structure: C(=O)-O-R²] or (d)

$SO_2$—$R^3$, $R^1$ most preferably represents $C_1$-$C_6$-alkyl or represents phenyl which is monosubstituted by chlorine,
$R^2$ most preferably represents $C_1$-$C_8$-alkyl,
$R^3$ most preferably represents $C_1$-$C_8$-alkyl.

The general or preferred radical definitions or illustrations given above can be combined with one another as desired, i.e. including combinations between respective ranges and preferred ranges.

They apply both to the end products and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitution the substituents can be identical or different.

In addition to the compounds mentioned in the preparation examples, particular mention may be made of the following compounds of the formula (I-1-a):

TABLE 1

[structure with A, B, D, N, OH, O, J, X, Y on phenyl ring]

J = 2 - [cyclopropyl] ; X = H; Y = H.

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| [cyclopropyl] | $CH_3$ | H |

TABLE 1-continued

![structure: pyrrolinone with OH, A, B, N-D, phenyl with J, X, Y substituents]

J = 2-cyclopropyl; X = H; Y = H.

| A–B | D | X/Y |
|---|---|---|
| cyclopentyl-CH< | CH₃ | H |
| cyclohexyl-CH< | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —CH₂—O—(CH₂)₃— | | H |
| —(CH₂)₂—S—(CH₂)₂— | | H |
| —CH₂—CHCH₃—(CH₂)₃— | | H |
| —CH₂—CHOCH₃—(CH₂)₃— | | H |
| —CH₂—CHOC₂H₅—(CH₂)₃— | | H |
| —CH₂—CHOC₃H₇—(CH₂)₃— | | H |
| —CH₂—CHOC₄H₉—(CH₂)₃— | | H |
| —CH₂—CHO—(CH₂)₂—OCH₃—(CH₂)₃— | | H |
| —CH₂—CH(O-CH₂-cyclopropyl)—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHO-i-C₃H₇—(CH₂)₂— | | H |
| —(CH₂)₂—C(CH₃)₂—(CH₂)₂— | | H |
| —CH₂—(CHCH₃)₂—(CH₂)₂— | | H |
| —CH₂—CH—(CH₂)₂—CH— with —CH₂— bridge | | H |
| —CH₂—CH—CH—CH₂— with (CH₂)₄ bridge | | H |
| —CH₂—CH—CH—(CH₂)₂— with (CH₂)₃ bridge | | H |
| indanyl | | H |
| tetrahydronaphthyl | | H |
| —(CH₂)₂—C(1,3-dioxolane)—(CH₂)₂— | | H |
| —(CH₂)₂—C(4-methyl-1,3-dioxolane)—(CH₂)₂— | | H |
| —(CH₂)₂—C(4,5-dimethyl-1,3-dioxolane)—(CH₂)₂— | | H |
| —(CH₂)₂—C(1,3-dioxane)—(CH₂)₂— | | H |
| —(CH₂)₂—C(4-methyl-1,3-dioxane)—(CH₂)₂— | | H |
| —(CH₂)₂—C(5-methyl-1,3-dioxane)—(CH₂)₂— | | H |
| —(CH₂)₂—C(4,6-dimethyl-1,3-dioxane)—(CH₂)₂— | | H |

TABLE 1-continued

Structure: pyrrolinone with OH, A, B on one carbon, N-D, aryl substituent with J, X, Y J = 2-cyclopropyl; X = H; Y = H.

| A | | B |
|---|---|---|
| —(CH₂)₂—C(CH₂)₂— (forming 1,3-dioxane with 5,5-dimethyl) | | H |
| —CH₂—CH(CH₂OCH₃)—(CH₂)₃— | | H |
| —CH₂—CH((CH₂)₂OCH₃)—(CH₂)₃— | | H |
| —(CH₂)₂—CH(CH₂OCH₃)—(CH₂)₂— | | H |
| —(CH₂)₂—CH((CH₂)₂OCH₃)—(CH₂)₂— | | H |
| —CH₂—CH(CH₂OCH₂CH₃)—(CH₂)₃— | | H |
| —CH₂—CH((CH₂)₂OCH₂CH₃)—(CH₂)₃— | | H |
| —(CH₂)₂—CH(CH₂OCH₂CH₃)—(CH₂)₂— | | H |
| —(CH₂)₂—CH((CH₂)₂OCH₂CH₃)—(CH₂)₂— | | H |

| A | D | B |
|---|---|---|
| | —(CH₂)₃— | H |
| | —(CH₂)₄— | H |
| | —CH₂—CHCH₃—CH₂— | H |
| | —CH₂—CH₂—CHCH₃— | H |
| | —CH₂—CHCH₃—CHCH₃— | H |
| | —CH₂—CH(OCH₃)—CH₂— | H |
| | —CH₂—CH=CH—CH₂— | H |
| | —CH₂—CH(—O—)CH—CH₂— (epoxide) | H |
| | —CH₂—S—CH₂— | H |
| | —CH₂—S—(CH₂)₂— | H |
| | —CH₂—S—CH₂— | H |

TABLE 1-continued

J = 2-cyclopropyl; X = H; Y = H.

| A | B | D |
|---|---|---|
| —CH₂—CH—CH—(CH₂)₃— (forming ring) | | |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |

TABLE 2

A, B and D as stated in Table 1

J = 2-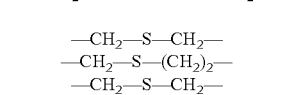; X = 4-CH₃; Y = H

TABLE 3

A, B and D as stated in Table 1

J = 2-cyclopropyl; X = 6-CH₃; Y = H.

TABLE 4

A, B and D as stated in Table 1

J = 2-cyclopropyl; X = 6-C₂H₅; Y = H.

TABLE 5

A, B and D as stated in Table 1

X = 2-CH$_3$; Y = H; J = 5 - 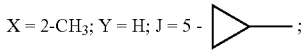;

TABLE 6

A, B and D as stated in Table 1

X = 2-CH$_3$; Y = 4-CH$_3$; J = 5 - 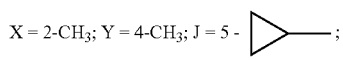;

TABLE 7

A, B and D as stated in Table 1

J = 2 - 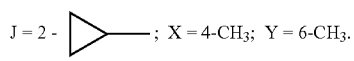; X = 4-CH$_3$; Y = 6-CH$_3$.

TABLE 8

A, B and D as stated in Table 1

J = 2 - 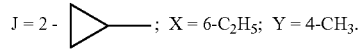; X = 6-C$_2$H$_5$; Y = 4-CH$_3$.

TABLE 9

A, B and D as stated in Table 1

J = 2 - 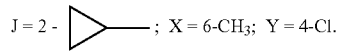; X = 6-CH$_3$; Y = 4-Cl.

TABLE 10

A, B and D as stated in Table 1

J = 2 - 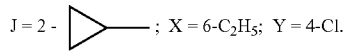; X = 6-C$_2$H$_5$; Y = 4-Cl.

TABLE 11

A, B and D as stated in Table 1

J = 2 - 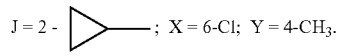; X = 6-Cl; Y = 4-CH$_3$.

TABLE 12

A, B and D as stated in Table 1

J = 2 - 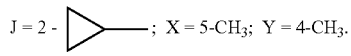; X = 5-CH$_3$; Y = 4-CH$_3$.

TABLE 13

A, B and D as stated in Table 1

X = 2-CH$_3$; J = 4 - ; Y = H.

TABLE 14

A, B and D as stated in Table 1

X = 2-C$_2$H$_5$; J = 4 - 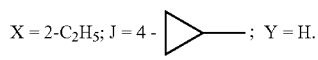; Y = H.

TABLE 15

A, B and D as stated in Table 1

X = 2-CH$_3$; J = 4 - ; Y = 6-CH$_3$.

TABLE 16

A, B and D as stated in Table 1

X = 2-C$_2$H$_5$; J = 4 - ; Y = 6-CH$_3$.

TABLE 17

A, B and D as stated in Table 1

X = 2-C$_2$H$_5$; J = 4 - ; Y = 6-C$_2$H$_5$.

TABLE 18

A, B and D as stated in Table 1

X = 2-Cl; J = 4 - 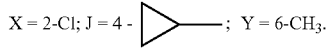; Y = 6-CH$_3$.

TABLE 19

A, B and D as stated in Table 1

X = 2-Cl; J = 4 - 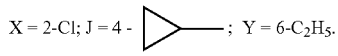; Y = 6-C$_2$H$_5$.

TABLE 20

A, B and D as stated in Table 1

X = 2-CH$_3$; J = 4 - ; Y = 5-CH$_3$.

TABLE 21

A, B and D as stated in Table 1

X = 2-CH₃; J = 3 - ◁ ; Y = 6-CH₃.

TABLE 22

A, B and D as stated in Table 1

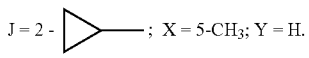
J = 2 - ◁ ; X = 5-CH₃; Y = H.

TABLE 22a

A and B as stated in Table 1

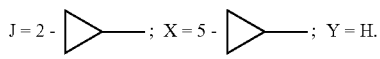
J = 2 - ◁ ; X = 5 - ◁ ; Y = H.

TABLE 23

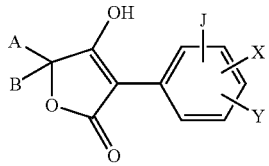

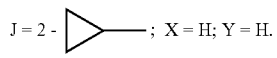
J = 2 - ◁ ; X = H; Y = H.

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
|  | CH₃ |
| 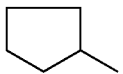 | CH₃ |
| 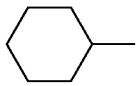 | CH₃ |
| —(CH₂)₂— | |
| —(CH₂)₄— | |
| —(CH₂)₅— | |
| —(CH₂)₆— | |
| —(CH₂)₇— | |

TABLE 23-continued

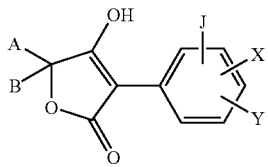

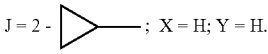
J = 2 - ◁ ; X = H; Y = H.

| A | B |
|---|---|
| —(CH₂)₂—O—(CH₂)₂— | |
| —CH₂—O—(CH₂)₃— | |
| —(CH₂)₂—S—(CH₂)₂— | |
| —CH₂—CHCH₃—(CH₂)₃— | |
| —CH₂—CHOCH₃—(CH₂)₃— | |
| —CH₂—CHOC₂H₅—(CH₂)₃— | |
| —CH₂—CHOC₃H₇—(CH₂)₃— | |
| —CH₂—CHOC₄H₉—(CH₂)₃— | |
| —CH₂—CHO—(CH₂)₂—OCH₃—(CH₂)₃— | |
| 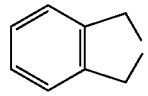 | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHO-i-C₃H₇—(CH₂)₂— | |
| —(CH₂)₂—C(CH₃)₂—(CH₂)₂— | |
| —CH₂(CHCH₃)₂—(CH₂)₂— | |
| 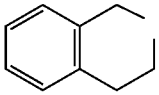 | |
| 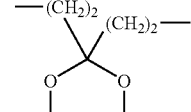 | |
| 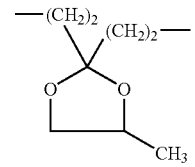 | |

TABLE 23-continued
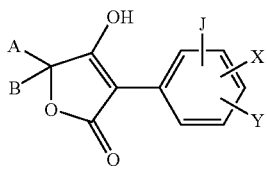
J = 2-△ ; X = H; Y = H.
| A | B |
|---|---|
| 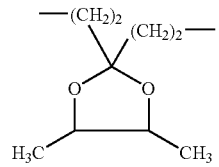 | |
| 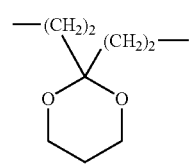 | |
| 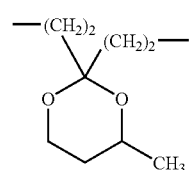 | |
| 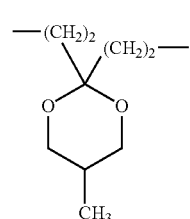 | |
| 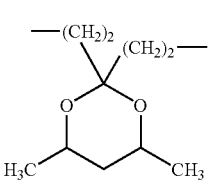 | |
| 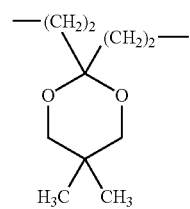 | |
| 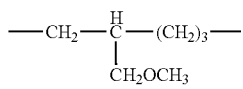 | |
| 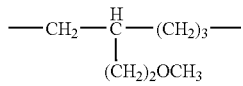 | |
TABLE 23-continued
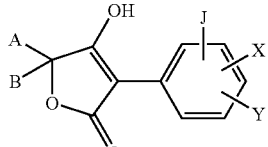
J = 2-△ ; X = H; Y = H.
| A | B |
|---|---|
| | 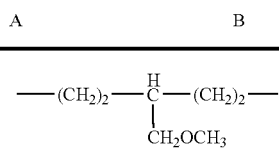 |
| | 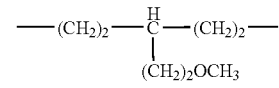 |
| | 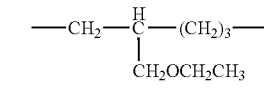 |
| | 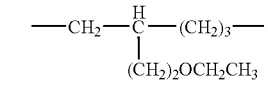 |
| | 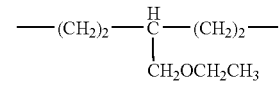 |
| | 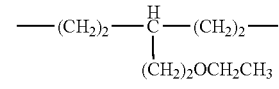 |
TABLE 24
A and B as stated in Table 23
J = 2-△ ; X = 4-CH$_3$; Y = H
TABLE 25
A and B as stated in Table 23
J = 2-△ ; X = 6-CH$_3$; Y = H.
TABLE 26
A and B as stated in Table 23
J = 2-△ ; X = 6-C$_2$H$_5$; Y = H.

TABLE 27

A and B as stated in Table 23

X = 2-CH$_3$; Y = H; J = 5-▷.

TABLE 28

A and B as stated in Table 23

X = 2-CH$_3$; Y = 4-CH$_3$; J = 5-▷—.

TABLE 29

A and B as stated in Table 23

J = 2-▷—; X = 4-CH$_3$; Y = 6-CH$_3$.

TABLE 30

A and B as stated in Table 23

J = 2-▷—; X = 6-C$_2$H$_5$; Y = 4-CH$_3$.

TABLE 31

A and B as stated in Table 23

J = 2-▷—; X = 6-CH$_3$; Y = 4-Cl.

TABLE 32

A and B as stated in Table 23

J = 2-▷—; X = 6-C$_2$H$_5$; Y = 4-Cl.

TABLE 33

A and B as stated in Table 23

J = 2-▷—; X = 6-Cl; Y = 4-CH$_3$.

TABLE 34

A and B as stated in Table 23

J = 2-▷—; X = 5-CH$_3$; Y = 4-CH$_3$.

TABLE 35

A and B as stated in Table 23

X = 2-CH$_3$; J = 4-▷—; Y = H.

TABLE 36

A and B as stated in Table 23

X = 2-C$_2$H$_5$; J = 4-▷—; Y = H.

TABLE 37

A and B as stated in Table 23

X = 2-CH$_3$; J = 4-▷—; Y = 6-CH$_3$.

TABLE 38

A and B as stated in Table 23

X = 2-C$_2$H$_5$; J = 4-▷—; Y = 6-CH$_3$.

TABLE 39

A and B as stated in Table 23

X = 2-C$_2$H$_5$; J = 4-▷—; Y = 6-C$_2$H$_5$.

TABLE 40

A and B as stated in Table 23

X = 2-Cl; J = 4-▷—; Y = 6-CH$_3$.

TABLE 41

A and B as stated in Table 23

X = 2-Cl; J = 4-▷—; Y = 6-C$_2$H$_5$.

TABLE 42

A and B as stated in Table 23

X = 2-CH$_3$; J = 4-▷—; Y = 5-CH$_3$.

TABLE 43

A and B as stated in Table 23

X = 2-CH₃; J = 3-△ ; Y = 6-CH₃.

TABLE 44

A and B as stated in Table 23

J = 2-△ ; X = 5-CH₃; Y = H.

TABLE 45

A and B as stated in Table 23

J = 2-△ ; X = 5-△ ; Y = H.

TABLE 46

A and B as stated in Table 23

[Structure: pyrazolidine-3,5-dione with A–N, D–N, H, J, X, Y substituents on phenyl]

J = 2-△ ; X = H; Y = H.

| A | D |
|---|---|
| CH₃ | CH₃ |
| CH₃ | —(CH₂)₂OH |
| CH₃ | —(CH₂)₂OCH₃ |
| CH₃ | —(CH₂)₂—O—(CH₂)₂—OCH₃ |
| —(CH₂)₂—O—CH₃ | —(CH₂)₂—O—CH₃ |
| —(CH₂)₂—O—(CH₂)₂—OCH₃ | —(CH₂)₂—O—(CH₂)₂—OCH₃ |
| —(CH₂)₃— | |
| —(CH₂)₄— | |
| —(CH2)₂—O—(CH₂)₂— | |

[Structure: isopropyl ether of pentan-3-yl]

[Structure: 4,5-diethyl-1,3-dioxolan-2-one]

[Structure: cis-alkene chain]

[Structure: epoxide fused to cyclohexane]

[Structure: 3-ethyl-tetrahydrofuran-fused ring]

TABLE 46-continued

[Structure: pyrazolidine-3,5-dione with A–N, D–N, H, J, X, Y substituents on phenyl]

J = 2-△ ; X = H; Y = H.

| A | D |
|---|---|

[Structure: H₃CO-pentan-3-yl]

[Structure: 2,2-dimethyl-4,5-diethyl-1,3-dioxolane]

[Structure: H₃CO, H₃CO on pentane backbone]

[Structure: 4,5-diethyl-1,3-dioxolane]

[Structure: H₃CO—CH₂CH₂—O—pentan-3-yl]

TABLE 47

A and D as stated in Table 46

J = 2-△ ; X = 4-CH₃; Y = H

TABLE 48

A and D as stated in Table 46

J = 2-△ ; X = 6-CH₃; Y = H.

TABLE 49

A and D as stated in Table 46

J = 2-△ ; X = 6-C₂H₅; Y = H.

TABLE 50

A and D as stated in Table 46

X = 2-CH$_3$; Y = H; J = 5-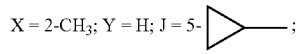;

TABLE 51

A and D as stated in Table 46

X = 2-CH$_3$; Y = 4-CH$_3$; J = 5-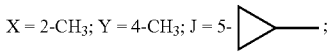;

TABLE 52

A and D as stated in Table 46

J = 2-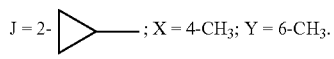; X = 4-CH$_3$; Y = 6-CH$_3$.

TABLE 53

A and D as stated in Table 46

J = 2-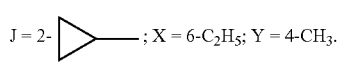; X = 6-C$_2$H$_5$; Y = 4-CH$_3$.

TABLE 54

A and D as stated in Table 46

J = 2-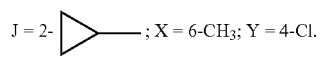; X = 6-CH$_3$; Y = 4-Cl.

TABLE 55

A and D as stated in Table 46

J = 2-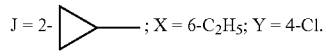; X = 6-C$_2$H$_5$; Y = 4-Cl.

TABLE 56

A and D as stated in Table 46

J = 2-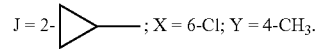; X = 6-Cl; Y = 4-CH$_3$.

TABLE 57

A and D as stated in Table 46

J = 2-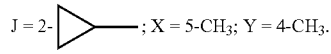; X = 5-CH$_3$; Y = 4-CH$_3$.

TABLE 58

A and D as stated in Table 46

X = 2-CH$_3$; J = 4-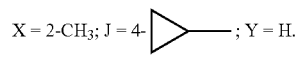; Y = H.

TABLE 59

A and D as stated in Table 46

X = 2-C$_2$H$_5$; J = 4-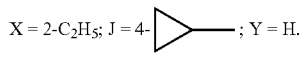; Y = H.

TABLE 60

A and D as stated in Table 46

X = 2-CH$_3$; J = 4-; Y = 6-CH$_3$.

TABLE 61

A and D as stated in Table 46

X = 2-C$_2$H$_5$; J = 4-; Y = 6-CH$_3$.

TABLE 62

A and D as stated in Table 46

X = 2-C$_2$H$_5$; J = 4-; Y = 6-C$_2$H$_5$.

TABLE 63

A and D as stated in Table 46

X = 2-Cl; J = 4-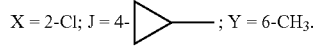; Y = 6-CH$_3$.

TABLE 64

A and D as stated in Table 46

X = 2-Cl; J = 4-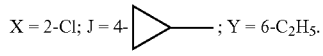; Y = 6-C$_2$H$_5$.

TABLE 65

A and D as stated in Table 46

X = 2-CH$_3$; J = 4-; Y = 5-CH$_3$.

TABLE 66

A and D as stated in Table 46

X = 2-CH$_3$; J = 3- ; Y = 6-CH$_3$.

TABLE 67

A and D as stated in Table 46

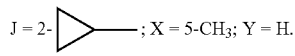
J = 2- ; X = 5-CH$_3$; Y = H.

TABLE 68

A and D as stated in Table 46

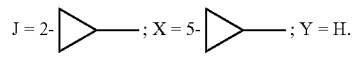
J = 2- ; X = 5- ; Y = H.

Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

A$^1$ preferably represents one of the divalent heterocyclic groupings shown below

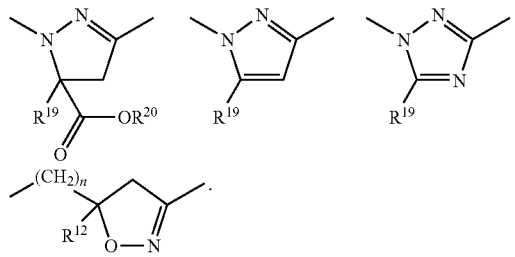

n preferably represents the numbers 0, 1, 2, 3 or 4.

A$^2$ preferably represents in each case optionally methyl-, ethyl-, methoxycarbonyl- or ethoxycarbonyl-substituted methylene or ethylene.

R$^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

R$^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

R$^{16}$ preferably represents in each case optionally fluorine-, chlorine- and/or bromine-substituted methyl, ethyl, n- or i-propyl.

R$^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

R$^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with R$^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

R$^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

R$^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

R$^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

X$^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

X$^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

X$^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, or 3.

R$^{22}$ preferably represents hydrogen, methyl, ethyl, n- or i-propyl.

R$^{23}$ preferably represents hydrogen, methyl, ethyl, n- or i-propyl.

R$^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

R$^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

| Example No. | (Positions) $(X^1)_m$ | $A^1$ | $R^{14}$ |
|---|---|---|---|
| IIa-1 | (2) Cl, (4) Cl | 1-methyl-3-methyl-5-(methoxycarbonyl)-4,5-dihydropyrazol-5-yl | $OCH_3$ |
| IIa-2 | (2) Cl, (4) Cl | 1-methyl-3-methyl-5-(ethoxycarbonyl)-4,5-dihydropyrazol-5-yl | $OCH_3$ |
| IIa-3 | (2) Cl, (4) Cl | 1-methyl-3-methyl-5-(methoxycarbonyl)-4,5-dihydropyrazol-5-yl | $OC_2H_5$ |
| IIa-4 | (2) Cl, (4) Cl | 1-methyl-3-methyl-5-(ethoxycarbonyl)-4,5-dihydropyrazol-5-yl | $OC_2H_5$ |
| IIa-5 | (2) Cl | 1-methyl-3-methyl-5-phenylpyrazol-5-yl | $OCH_3$ |
| IIa-6 | (2) Cl, (4) Cl | 1-methyl-3-methyl-5-phenylpyrazol-5-yl | $OCH_3$ |
| IIa-7 | (2) F | 1-methyl-3-methyl-5-phenylpyrazol-5-yl | $OCH_3$ |
| IIa-8 | (2) F | 1-methyl-3-methyl-5-(2-chlorophenyl)pyrazol-5-yl | $OCH_3$ |
| IIa-9 | (2) Cl, (4) Cl | 1-methyl-3-methyl-5-(trichloromethyl)-1,2,4-triazol-5-yl | $OC_2H_5$ |

TABLE-continued

Examples of the compounds of the formula (IIa)

(IIa)

| Example No. | (Positions) $(X^1)_m$ | $A^1$ | $R^{14}$ |
|---|---|---|---|
| IIa-10 | (2) Cl, (4) CF$_3$ | [1,2,4-triazole structure with phenyl] | OCH$_3$ |
| IIa-11 | (2) Cl | [pyrazole structure with 2-F-phenyl] | OCH$_3$ |
| IIa-12 | — | [isoxazoline with phenyl] | OC$_2$H$_5$ |
| IIa-13 | (2) Cl, (4) Cl | [pyrazole with CH$_3$] | OC$_2$H$_5$ |
| IIa-14 | (2) Cl, (4) Cl | [pyrazole with C$_3$H$_7$-i] | OC$_2$H$_5$ |
| IIa-15 | (2) Cl, (4) Cl | [pyrazole with C$_4$H$_9$-t] | OC$_2$H$_5$ |
| IIa-16 | (2) Cl, (4) Cl | [isoxazoline with CH$_2$] | OC$_2$H$_5$ |
| IIa-17 | (2) Cl, (4) Cl | [isoxazoline] | OC$_2$H$_5$ |
| IIa-18 | — | [isoxazoline with phenyl] | OH |

Examples of the compounds of the formula (IIb) which are very particularly preferred as herbicide safeners according to the invention are listed in the table below.

TABLE

Examples of the compounds of formula (IIb)

(IIb)

| Example No. | (Position) $X^2$ | (Position) $X^3$ | $A^2$ | $R^{15}$ |
|---|---|---|---|---|
| IIb-1 | (5) Cl | — | CH$_2$ | OH |
| IIb-2 | (5) Cl | — | CH$_2$ | OCH$_3$ |
| IIb-3 | (5) Cl | — | CH$_2$ | OC$_2$H$_5$ |
| IIb-4 | (5) Cl | — | CH$_2$ | OC$_3$H$_7$-n |
| IIb-5 | (5) Cl | — | CH$_2$ | OC$_3$H$_7$-i |
| IIb-6 | (5) Cl | — | CH$_2$ | OC$_4$H$_9$-n |
| IIb-7 | (5) Cl | — | CH$_2$ | OCH(CH$_3$)C$_5$H$_{11}$-n |
| IIb-8 | (5) Cl | (2) F | CH$_2$ | OH |
| IIb-9 | (5) Cl | (2) Cl | CH$_2$ | OH |
| IIb-10 | (5) Cl | — | CH$_2$ | OCH$_2$CH=CH$_2$ |
| IIb-11 | (5) Cl | — | CH$_2$ | OC$_4$H$_9$-i |
| IIb-12 | (5) Cl | — | CH$_2$ | [CH$_2$=CH-CH$_2$-O-CH$_2$-CH(OCH$_3$)-CH$_3$ group] |
| IIb-13 | (5) Cl | — | CH$_2$ [with CH(CH$_3$)-CH$_2$-O-C(=O)-] | OCH$_2$CH=CH$_2$ |
| IIb-14 | (5) Cl | — | C$_2$H$_5$ [with CH(CH$_3$)-C(=O)-O-] | OC$_2$H$_5$ |

TABLE-continued

Examples of the compounds of formula (IIb)

(IIb)

[Structure: quinoline with X³ at position 4 area, X² at position 5 area, positions labeled 2,3,4,5,6,7; 8-O-A²-C(=O)-R¹⁵]

| Example No. | (Position) X² | (Position) X³ | A² | R¹⁵ |
|---|---|---|---|---|
| IIb-15 | (5) Cl | — | [CH(CH₃)-C(=O)-O-] | OCH₃ |

Examples of the compounds of the formula (IIc) which are very particularly preferred as herbicide safeners according to the invention are listed in the table below.

TABLE

Examples of the compounds of the formula (IIc)

(IIc)

[Structure: R¹⁶-C(=O)-N(R¹⁷)(R¹⁸)]

| Example No. | R¹⁶ | N (R¹⁷, R¹⁸) |
|---|---|---|
| IIc-1 | CHCl₂ | N(CH₂CH=CH₂)₂ |
| IIc-2 | CHCl₂ | [2,2-dimethyl-3-methyl-oxazolidine] |
| IIc-3 | CHCl₂ | [2,2-dimethyl-3-methyl-5-methyl-oxazolidine] |
| IIc-4 | CHCl₂ | [spiro cyclohexane-oxazolidine, N-methyl] |
| IIc-5 | CHCl₂ | [2,2-dimethyl-3-methyl-5-phenyl-oxazolidine] |
| IIc-6 | CHCl₂ | [3,4-dihydro-4-methyl-3-methyl-2H-1,4-benzoxazine] |
| IIc-7 | CHCl₂ | [2,2-dimethyl-3-methyl-5-(2-furyl)-oxazolidine] |

Examples of the compounds of the formula (IId) which are very particularly preferred as herbicide safeners according to the invention are listed in the table below.

TABLE

Examples of the compounds of the formula (IId)

(IId)

| Example No. | R²² | R²³ | R²⁴ | (Positions) (X⁴)ₜ | (Positions) (X⁵)ᵥ |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | [cyclopropyl] | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

Examples of the compounds of the formula (IIe)

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | cyclopropyl | (2) $OCH$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, fiilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in the table below.

TABLE

Examples of the combinations according to the invention

| Active compounds of the formula (I) | Safeners |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-2 | cloquintocet-mexyl |
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-2 | IIe-5 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-7 | cloquintocet-mexyl |
| I-7 | fenchlorazole-ethyl |
| I-7 | isoxadifen-ethyl |
| I-7 | mefenpyr-diethyl |
| I-7 | furilazole |
| I-7 | fenclorim |
| I-7 | cumyluron |
| I-7 | daimuron/dymron |
| I-7 | dimepiperate |
| I-7 | IIe-5 |
| I-7 | IIe-11 |
| I-8 | cloquintocet-mexyl |
| I-8 | fenchlorazole-ethyl |
| I-8 | isoxadifen-ethyl |
| I-8 | mefenpyr-diethyl |
| I-8 | furilazole |
| I-8 | fenclorim |
| I-8 | cumyluron |
| I-8 | daimuron/dymron |
| I-8 | dimepiperate |
| I-8 | IIe-5 |
| I-8 | IIe-11 |
| I-9 | cloquintocet-mexyl |
| I-9 | fenchlorazole-ethyl |
| I-9 | isoxadifen-ethyl |
| I-9 | mefenpyr-diethyl |
| I-9 | furilazole |
| I-9 | fenclorim |
| I-9 | cumyluron |
| I-9 | daimuron/dymron |
| I-9 | dimepiperate |
| I-9 | IIe-5 |
| I-9 | IIe-11 |
| I-10 | cloquintocet-mexyl |
| I-10 | fenchlorazole-ethyl |
| I-10 | isoxadifen-ethyl |
| I-10 | mefenpyr-diethyl |
| I-10 | furilazole |
| I-10 | fenclorim |
| I-10 | cumyluron |
| I-10 | daimuron/dymron |
| I-10 | dimepiperate |
| I-10 | IIe-5 |
| I-10 | IIe-11 |

It has now surprisingly been found that the above-defined active compound combinations of cycloalkylphenyl-substituted cyclic ketoenols of the general formula (I) and safeners (antidotes) from the group (b') set out above combine very good useful plant tolerance with a particularly high herbicidal activity and can be used in various crops, in particular in cereals (especially wheat), but also in soya beans, potatoes, corn and rice, for selective weed control.

In this context it is considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of cycloalkylphenyl-substituted cyclic ketoenols on the crop plants, without at the same time having any critical adverse effect on the herbicidal activity against the weeds.

Emphasis may be given here to the particularly advantageous effect of the particularly preferred and most preferred combination partners from group (b'), particularly with regard to the gentle treatment of cereal plants, such as wheat, barley and rye, for example, but also corn and rice, as crop plants.

Descriptions have already been given in the literature to the effect that the activity of various active compounds can be increased through addition of ammonium salts. The salts in question, however, are salts with a detergent effect (for example WO 95/017817) and/or salts having relatively long alkyl and/or aryl substituents, which have a permeabilizing effect or which increase the solubility of the active compound (for example EP-A 0 453 086, EP-A 0 664 081, FR-A 2 600

494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active compounds and/or certain applications of the composition in question. In still other cases, they are salts of sulphonic acids where the acids for their part have a paralysing action on insects (U.S. Pat. No. 2,842,476). An activity increase for example through ammonium sulphate is described for the herbicides glyphosate and phosphinothricin (U.S. Pat. No. 6,645,914, EP-A2 0 036 106). However, this prior art neither discloses nor suggests a corresponding activity for insecticides.

Also, the use of ammonium sulphate as a formulating auxiliary has been described for certain active compounds and applications (WO 92/16108), but it is used there for the purpose of stabilizing the formulation, not for increasing activity.

It has now been found, entirely surprisingly, that the activity of insecticides and/or acaricides and/or herbicides from the class of the cycloalkylphenyl-substituted spirocyclic ketoenols can be increased significantly through the addition of ammonium salts or phosphonium salts to the use solution or through the incorporation of these salts into a formulation comprising cycloalkylphenyl-substituted cyclic ketoenols. Accordingly, the present invention provides the use of ammonium salts or phosphonium salts for increasing the activity of crop protection compositions comprising insecticidally and/or acaricidally active cycloalkylphenyl-substituted cyclic ketoenols as active compound. The invention also provides compositions comprising insecticidally active cycloalkylphenyl-substituted cyclic ketoenols and activity-increasing ammonium salts or phosphonium salts, specifically including not only formulated active compounds but also ready-to-use compositions (spray liquors). Finally, the invention also provides the use of these compositions for controlling harmful insects and/or spider mites and/or unwanted vegetation.

The compounds of the formula (I) have broad insecticidal and/or acaricidal and/or herbicidal action; however, in specific cases the activity and/or compatibility with crops is unsatisfactory.

The active compounds can be used in the compositions according to the invention in a broad concentration range. Here, the concentration of the active compounds in the formulation is usually 0.1-50% by weight.

Ammonium salts and phosphonium salts which, according to the invention, increase the activity of crop protection compositions comprising fatty acid biosynthesis inhibitors are defined by formula (III')

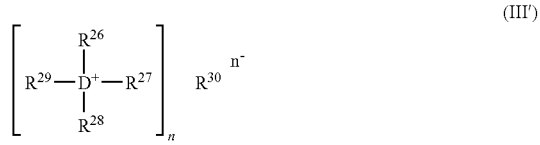

(III')

in which
D represents nitrogen or phosphorus,
D preferably represents nitrogen,
$R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano,
$R^{26'}$, $R^{27}$, $R^{28}$ and $R^{29}$ preferably independently of one another represent hydrogen or in each case optionally substituted $C_1$-$C_4$-alkyl, where the substituents may be selected from the group consisting of halogen, nitro and cyano,
$R^{26'}$, $R^{27}$, $R^{28}$ and $R^{29}$ particularly preferably independently of one another represent hydrogen, methyl, ethyl, n-propyl, isopropyl, n-butyl, isobutyl, s-butyl or t-butyl,
$R^{26'}$, $R^{27}$, $R^{28}$ and $R^{29}$ very particularly preferably represent hydrogen,
n represents 1, 2, 3 or 4,
n preferably represents 1 or 2,
$R^{30}$ represents an inorganic or organic anion,
$R^{30}$ preferably represents bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, sulphate, nitrate, thiosulphate, thiocyanate, oxalate or formate,
$R^{30}$ very particularly preferably represents sulphate.

Combinations of active compound, salt and penetrant which are especially preferred according to the invention are listed in the table below. Here, "penetrant according to test" means that each compound which acts as a penetrant in the cuticle penetration test (Baur et al., 1997, Pesticide Science 51, 131-152) is suitable.

The ammonium salts and phosphonium salts of the formula (III') can be used in a broad concentration range to increase the activity of crop protection compositions comprising ketoenols. In general, the ammonium salts or phosphonium salts are used in the ready-to-use crop protection composition in a concentration of from 0.5 to 80 mmol/l, preferably from 0.75 to 37.5 mmol/l, particularly preferably from 1.5 to 25 mmol/l. In the case of a formulated product, the ammonium salt concentration and/or phosphonium salt concentration in the formulation is chosen such that it is within these stated general, preferred or very preferred ranges after the formulation has been diluted to the desired active compound concentration. The concentration of the salt in the formulation here is typically 1-50% by weight.

In a preferred embodiment of the invention, the activity is increased by adding to the crop protection compositions not only an ammonium salt and/or phosphonium salt but also, additionally, a penetrant. It is considered entirely surprising that even in these cases an even greater activity increase is observed. The present invention therefore likewise provides the use of a combination of penetrant and ammonium salts and/or phosphonium salts for increasing the activity of crop protection compositions comprising insecticidally active cycloalkylphenyl-substituted cyclic ketoenols as active compound. The invention likewise provides compositions which comprise insecticidally active cycloalkylphenyl-substituted cyclic ketoenols, penetrants and ammonium salts and/or phosphonium salts, including specifically not only formulated active compounds but also ready-to-use compositions (spray liquors). The invention additionally provides, finally, for the use of these compositions for controlling harmful insects.

Suitable penetrants in the present context include all those substances which are typically used to enhance the penetration of agrochemically active compounds into plants. Penetrants are defined in this context by their ability to penetrate from the aqueous spray liquor and/or from the spray coating into the cuticle of the plant and thereby to increase the mobility of active compounds in the cuticle. The method described in the literature (Baur et al., 1997, *Pesticide Science* 51, 131-152) can be used in order to determine this property.

Suitable penetrants are, for example, alkanol alkoxylates. Penetrants according to the invention are alkanol alkoxylates of the formula (IV')

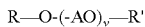 (IV')

in which
R represents straight-chain or branched alkyl having 4 to 20 carbon atoms,
R' represents hydrogen, methyl, ethyl, n-propyl, isopropyl, n-butyl, isobutyl, t-butyl, n-pentyl or n-hexyl,
AO represents an ethylene oxide radical, a propylene oxide radical, a butylene oxide radical or represents mixtures of ethylene oxide and propylene oxide radicals or butylene oxide radicals and
v represents numbers from 2 to 30.

A preferred group of penetrants are alkanol alkoxylates of the formula

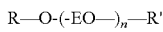 (IV'-a)

in which
R is as defined above,
R' is as defined above,
EO represents —$CH_2$—$CH_2$—O— and
n represents numbers from 2 to 20.

A further preferred group of penetrants are alkanol alkoxylates of the formula

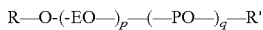 (IV'-b)

in which
R is as defined above,
R' is as defined above,
EO represents —$CH_2$—$CH_2$—O—,
PO represents

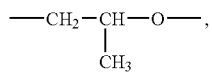

p represents numbers from 1 to 10 and
q represents numbers from 1 to 10.

A further preferred group of penetrants are alkanol alkoxylates of the formula

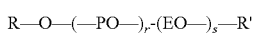 (IV'-c)

in which
R is as defined above,
R' is as defined above,
EO represents —$CH_2$—$CH_2$—O—,
PO represents

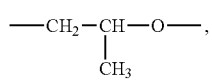

r represents numbers from 1 to 10 and
s represents numbers from 1 to 10.

A further preferred group of penetrants are alkanol alkoxylates of the formula

 (IV'-d)

in which
R and R' are as defined above,
EO represents $CH_2$—$CH_2$—O—,
BO represents

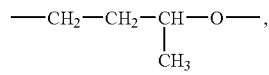

p represents numbers from 1 to 10 and
q represents numbers from 1 to 10.

A further preferred group of penetrants are alkanol alkoxylates of the formula

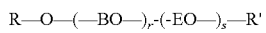 (IV'-e)

in which
R and R' are as defined above,
BO represents

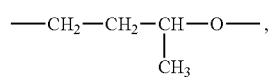

EO represents $CH_2$—$CH_2$—O—,
r represents numbers from 1 to 10 and
s represents numbers from 1 to 10.

A further preferred group of penetrants are alkanol alkoxylates of the formula

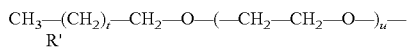 (IV'-f)

in which
R' is as defined above,
t represents numbers from 8 to 13
u represents numbers from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

An example which may be mentioned of an alkanol alkoxylate of the formula (III-c) is 2-ethyl-hexyl alkoxylate of the formula

 (IV'-c-1)

in which
EO represents —$CH_2$—$CH_2$—O—,
PO represents

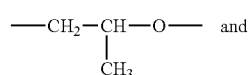 and the numbers 8 and 6 are average values.

An example which may be mentioned of an alkanol alkoxylate of the formula (IV-d) is the formula

 (IV'-d-1)

in which
EO represents $CH_2$—$CH_2$—O—,

BO represents

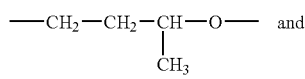 and the numbers 10, 6 and 2 are average values.

Particularly preferred alkanol alkoxylates of the formula (IV'-f) are compounds of this formula in which t represents numbers from 9 to 12 and
u represents numbers from 7 to 9.

The alkanol alkoxylate of the formula (IV'-f-1)

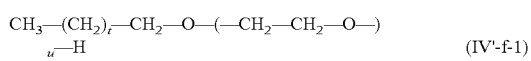 (IV'-f-1)

in which t represents the average value 10.5 and
u represents the average value 8.4 may be mentioned as being very particularly preferred.

The above formulae provide a general definition of the alkanol alkoxylates. These substances are mixtures of substances of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in a spray coating. These include, for example, mineral and vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maizeseed oil, cottonseed oil and soybean oil, or the esters of said oils. Preference is given to rapeseed oil, sunflower oil and their methyl or ethyl esters.

The concentration of penetrants in the compositions according to the invention can be varied within a wide range. In the case of a formulated crop protection composition, it is generally from 1 to 95% by weight, preferably from 1 to 55% by weight, particularly preferably from 15 to 40% by weight. In the ready-to-use compositions (spray liquors), the concentration is generally between 0.1 and 10 g/l, preferably between 0.5 and 5 g/l.

Crop protection compositions according to the invention may also comprise further components, for example, surfactants and/or dispersing auxiliaries or emulsifiers.

Suitable nonionic surfactants and/or dispersing auxiliaries include all substances of this type that can usually be used in agrochemical compositions. Polyethylene oxide/polypropylene oxide block copolymers, polyethylene glycol ethers of straight-chain alcohols, reaction products of fatty acids with ethylene oxide and/or propylene oxide, furthermore polyvinyl alcohol, polyvinyl pyrrolidone, copolymers of polyvinyl alcohol and polyvinyl pyrrolidone and copolymers of (meth) acrylic acid and (meth)acrylic esters, and additionally alkyl ethoxylates and alkylaryl ethoxylates, which optionally may be phosphated and optionally may be neutralized with bases, examples of which may be mentioned being sorbitol ethoxylates, and also polyoxyalkyleneamine derivatives may be mentioned as being preferred.

Suitable anionic surfactants are all substances of this type that can usually be used in agrochemical compositions. Preference is given to alkali metal salts and alkaline earth metal salts of alkylsulphonic acids or alkylarylsulphonic acids.

A further preferred group of anionic surfactants and/or dispersing auxiliaries are the following salts that are of low solubility in plant oil: salts of polystyrenesulphonic acids, salts of polyvinylsulphonic acids, salts of naphthalenesulphonic acid/formaldehyde condensation products, salts of condensation products of naphthalenesulphonic acid, phenolsulphonic acid and formaldehyde, and salts of lignosulphonic acid.

Suitable additives which may be included in the formulations according to the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide sorbitan fatty acid esters and sorbitan fatty acid esters.

Using, for example, according to process (A) ethyl N-(2, 6-dimethyl-4-cyclopropylphenylacetyl)-1-aminocyclohexanecarboxylate as starting material, the course of the process according to the invention can be represented by the reaction scheme below:

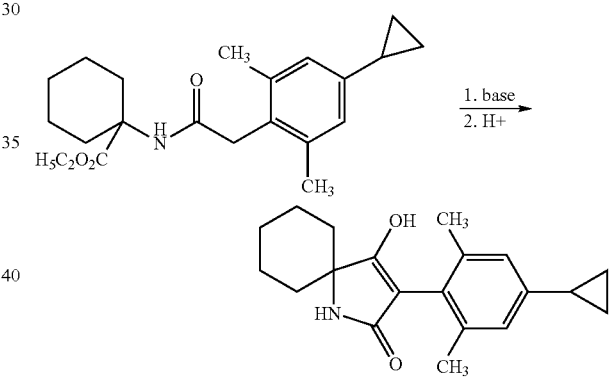

Using, for example, according to process (B) ethyl O-(2, 6-dimethyl-4-cyclopropylphenylacetyl)-2-hydroxyisobutyrate, the course of the process according to the invention can be represented by the reaction scheme below:

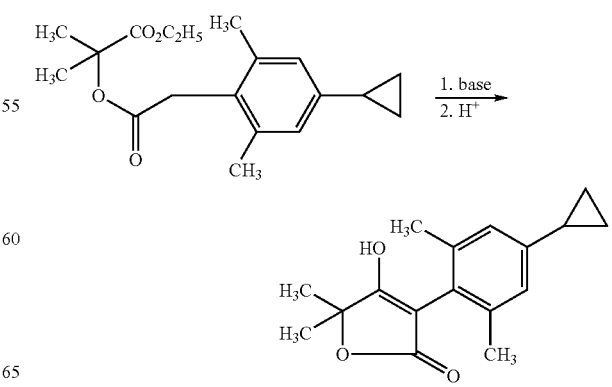

Using, for example, according to process (C) ethyl 2-(2,6-dimethyl-4-cyclopropylphenyl)-4-(4-methoxy)benzylmercapto-4-methyl-3-oxovalerate, the course of the process according to the invention can be represented by the reaction scheme below:

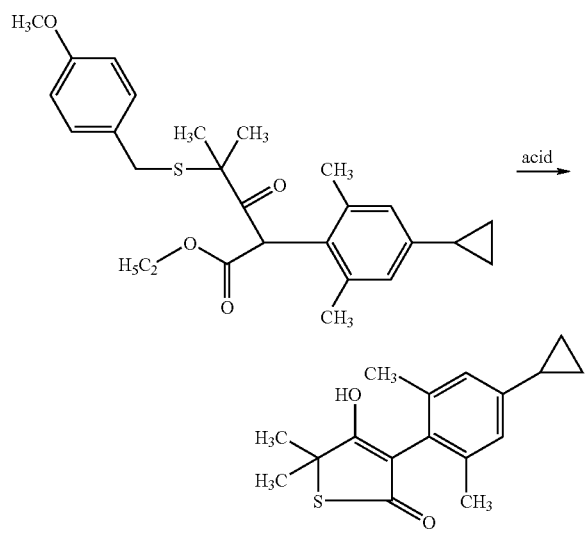

Using, for example, according to process (D) chlorocarbonyl 2-(2,6-dimethyl-4-cyclopropyl-phenyl) ketene and acetone as starting materials, the course of the process according to the invention can be represented by the reaction scheme below:

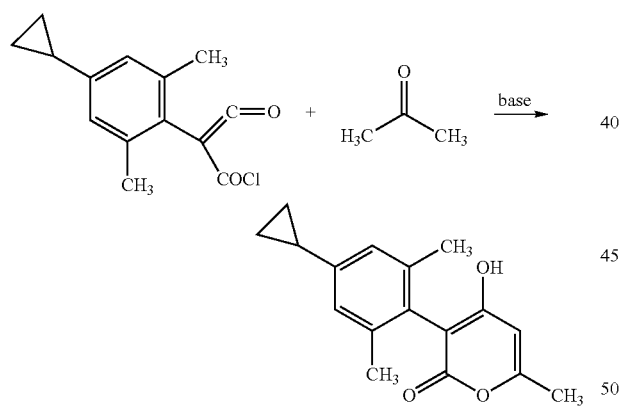

Using, for example, according to process (E) chlorocarbonyl 2-(2,6-dimethyl-4-cyclopropylphenyl) ketene and thiobenzamide as starting materials, the course of the process according to the invention can be represented by the reaction scheme below:

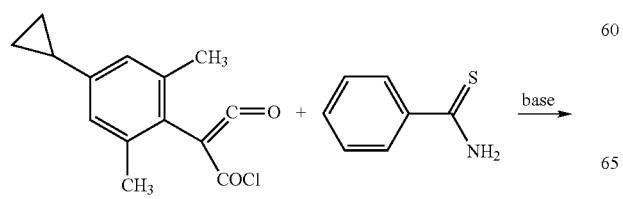

-continued

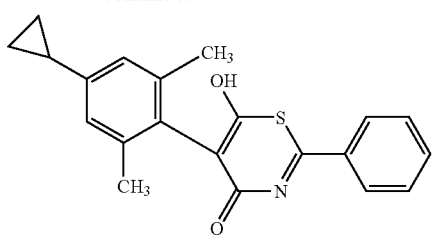

Using, for example, according to process (F) ethyl 5-(2,6-dimethyl-4-cyclopropylphenyl)-2,3-trimethylene-4-oxovalerate, the course of the process according to the invention can be represented by the reaction scheme below:

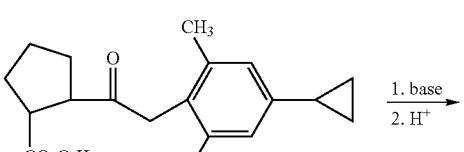

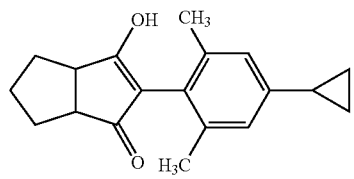

Using, for example, according to process (G) ethyl 5-[(2,6-dimethyl-4-cyclopropyl)phenyl]-2-methyl-5-oxohexanoate, the course of the process according to the invention can be represented by the reaction scheme below:

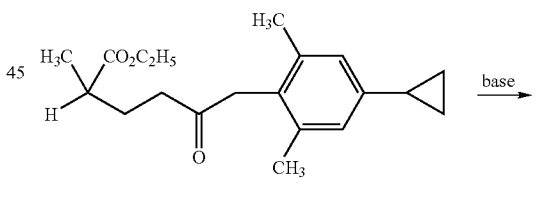

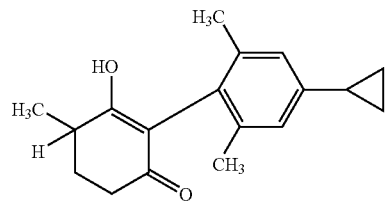

Using, for example, according to process (Hα) hexahydropyridazine and chlorocarbonyl 2-(2,6-dimethyl-4-cyclopropyl)phenyl ketene as starting materials, the course of the reaction of the process according to the invention can be represented by the reaction scheme below:

Using, for example, according to process (Hβ) hexahydropyridazine and dimethyl 2-(2,6-dimethyl-4-cyclopropyl)phenylmalonate as starting materials, the course of the process according to the invention can be represented by the reaction scheme below:

Using, for example, according to process (Hγ) 1-ethoxycarbonyl-2-[(2,6-dimethyl-4-cyclopropyl)-phenylacetyl] hexahydropyridazine as starting material, the course of the reaction can be represented by the scheme below:

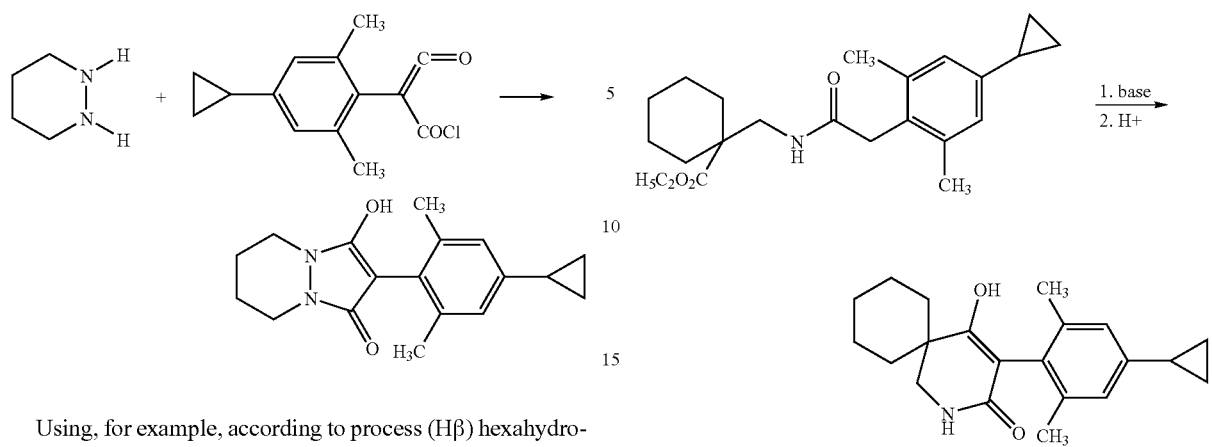

Using, for example, according to process (I) ethyl N-(2,6-dimethyl-4-cyclopropylphenylacetyl)-1-aminocyclohexanecarboxylate as starting material, the course of the process according to the invention can be represented by the reaction scheme below:

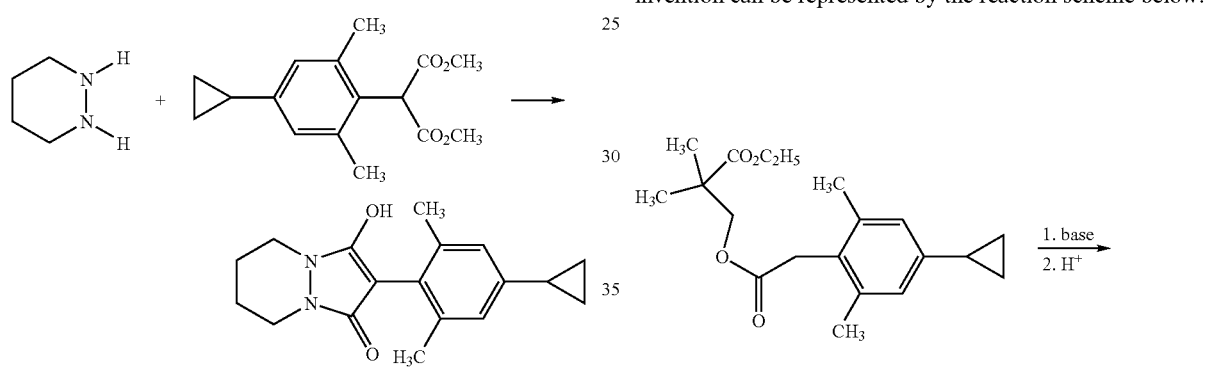

Using, for example, according to process (J) ethyl O-(2,6-dimethyl-4-cyclopropylphenylacetyl)-3-hydroxy-2,2-dimethylpropionate, the course of the process according to the invention can be represented by the reaction scheme below:

Using, for example, according to process (Kα) 3-(2-methyl-4-cyclopropyl-6-ethylphenyl)-5,5-dimethylpyrrolidine-2,4-dione and pivaloyl chloride as starting materials, the course of the process according to the invention can be represented by the reaction scheme below:

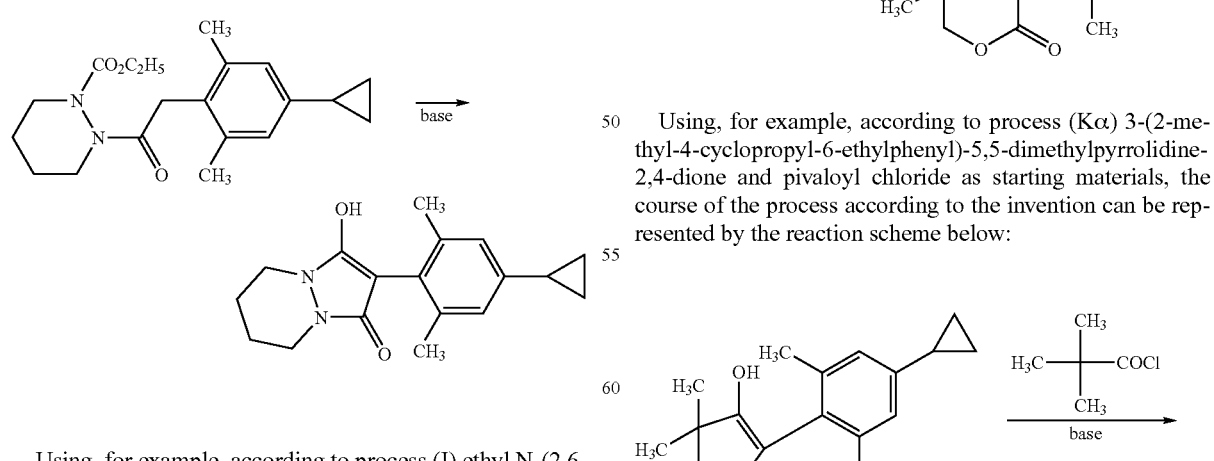

-continued

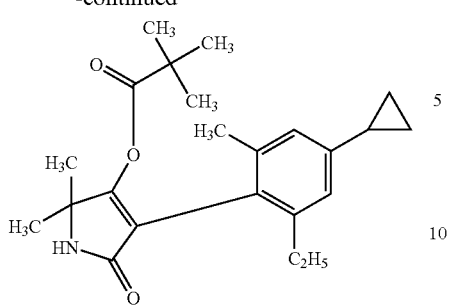

Using, for example, according to process (Kβ) 3-(2,6-dimethyl-4-cyclopropylphenyl)-5,5-dimethylpyrrolidine-2,4-dione and acetic anhydride as starting materials, the course of the process according to the invention can be represented by the reaction scheme below:

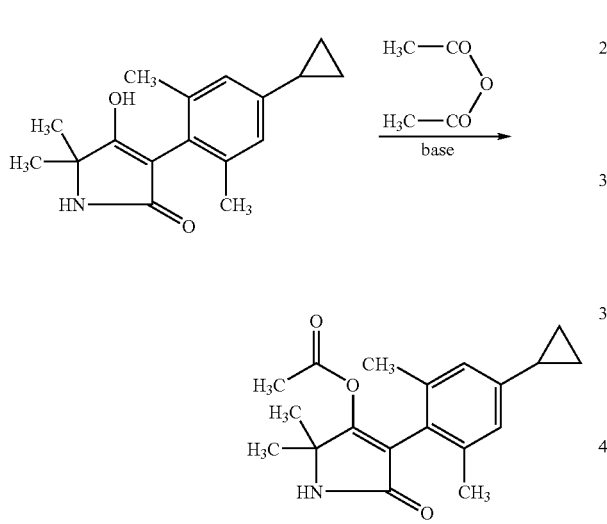

Using, for example, according to process (J) 8-[(2,6-dimethyl-4-cyclopropyl)phenyl]-1-aza-bicyclo(4.3.0$^{1.6}$)nonane-7,9-dione and ethyl chloroformate as starting materials, the course of the process according to the invention can be represented by the reaction scheme below:

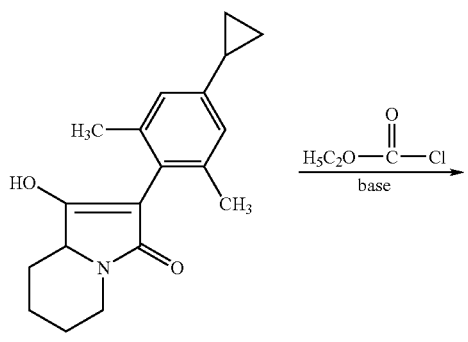

-continued

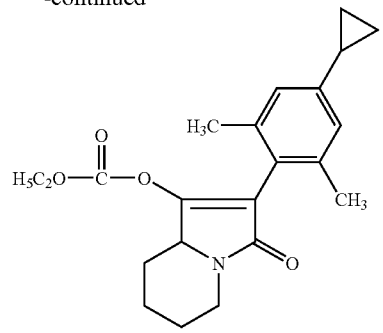

Using, for example, according to process (M), 3-(2,6-dimethyl-4-cyclopropylphenyl)-4-hydroxy-5-methyl-6-(3-pyridyl)pyrone and methyl chloromonothioformate as starting materials, the course of the reaction can be represented as follows:

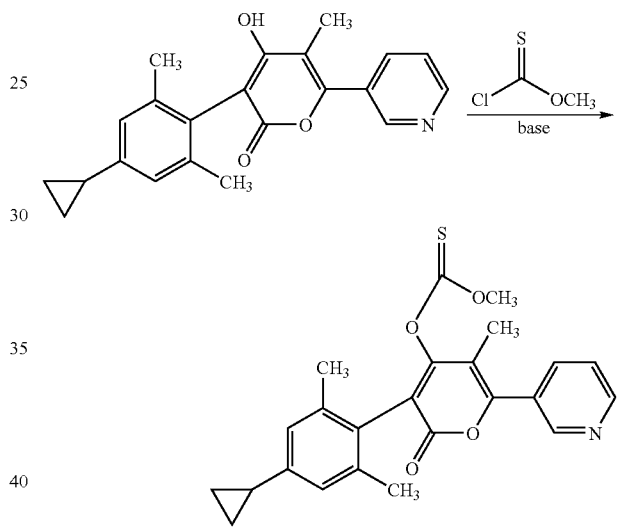

Using, for example, according to process (N) 3-(2,6-dimethyl-4-cyclopropylphenyl)-5,5-pentamethylenepyrrolidine-2,4-dione and methanesulphonyl chloride as starting materials, the course of the reaction can be represented by the reaction scheme below:

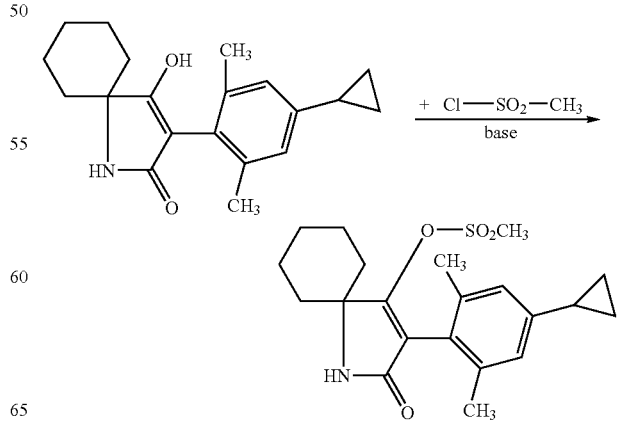

Using, for example, according to process (O) 3-(2,6-dimethyl-4-cyclopropylphenyl)-4-hydroxy-5,5-dimethylpyrrolidine-2,4-dione and 2,2,2-trifluoroethyl methanethiophosphonyl chloride as starting materials, the course of the reaction can be represented by the reaction scheme below:

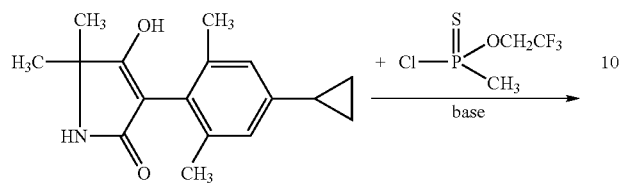

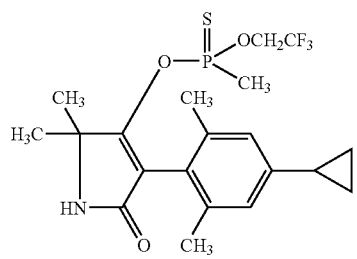

Using, for example, according to process (P) 3-(2-ethyl-4-cyclopropyl-6-methylphenyl)-5-cyclo-propyl-5-methylpyrrolidine-2,4-dione and NaOH as components, the course of the process according to the invention can be represented by the reaction scheme below

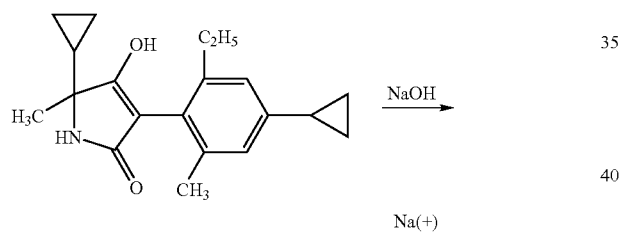

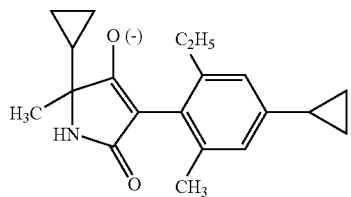

Using, for example, according to process (Q) variant α 3-(2,6-dimethylcyclopropylphenyl)-4-hydroxy-5,5-tetramethylene-Δ³-dihydrofuran-2-one and ethyl isocyanate as starting materials, the course of the reaction can be represented by the reaction scheme below:

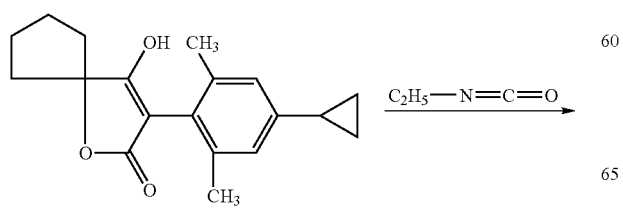

-continued

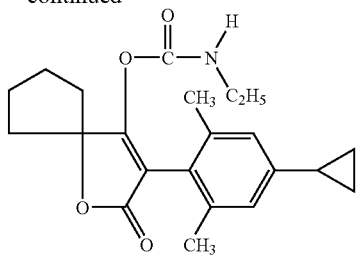

Using, for example, according to process (Q) variant β 3-(2-methyl-4-cyclopropyl-6-ethylphenyl)-5-methylpyrrolidine-2,4-dione and dimethylcarbamoyl chloride as starting materials, the course of the reaction can be represented by the scheme below:

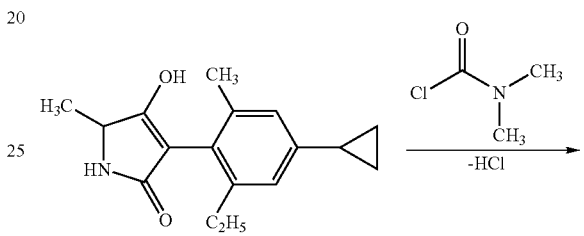

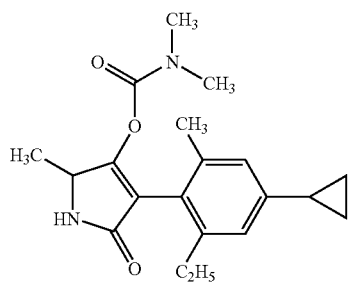

Using, for example, according to process (R) 3-(4-bromo-2,6-dimethylphenyl)-5,5-dimethyl-pyrrolidine-2,4-dione and cyclopropylboronic acid as starting materials, the course of the reaction can be represented by the scheme below:

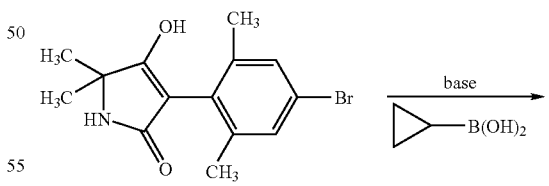

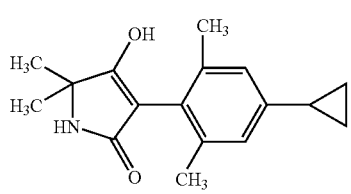

The compounds, required as starting materials in the process (a) according to the invention, of the formula (II)

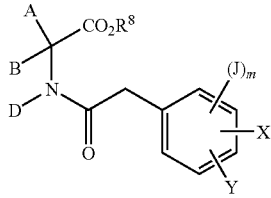
(II)

in which
A, B, D, J, m, X, Y and $R^8$ are as defined above,
are novel.

The acylamino acid esters of the formula (II) are obtained, for example, when amino acid derivatives of the formula (XXVI)

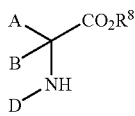
(XXVI)

in which
A, B, $R^8$ and D are as defined above
are acylated with substituted phenyl acetic acid derivatives of the formula (XXVII)

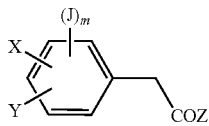
(XXVII)

in which
J, m, X and Y are as defined above and
Z represents a leaving group introduced by carboxylic acid-activating reagents, such as carbonyldiimidazole, carbodiimides (such as, for example, dicyclohexylcarbodiimide), phosphorylating agents (such as, for example, $POCl_3$, BOP—Cl), halogenating agents, for example thionyl chloride, oxalyl chloride, phosgene or chloroformic esters (Chem. Reviews 52, 237-416 (1953); Bhattacharya, Indian J. Chem. 6, 341-5, 1968)
or when acylamino acids of the formula (XXVIII)

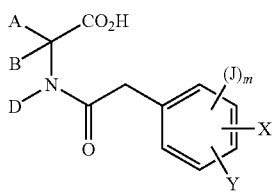
(XXVIII)

in which
A, B, D, J, m, X and Y are as defined above
are esterified (Chem. Ind. (London) 1568 (1968)).

The compounds of the formula (XXVIII)

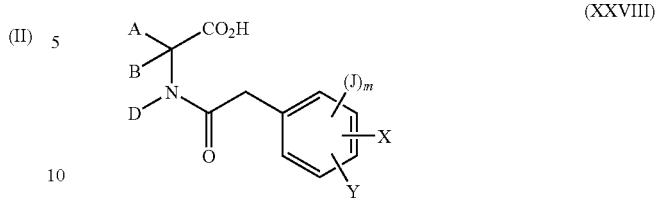
(XXVIII)

in which
A, B, D, J, m, X and Y are as defined above
are novel.

The compounds of the formula (XXVIII) are obtained when amino acids of the formula (XXIX)

(XXIX)

in which
A, B and D are as defined above
are acylated with substituted phenylacetic acid derivatives of the formula (XXVII)

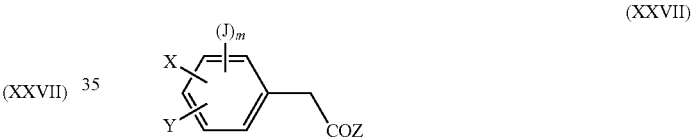
(XXVII)

in which
J, m, X and Y are as defined above and
Z is as defined above,
for example according to Schotten-Baumann (Organikum, VEB Deutscher Verlag der Wissen-schaften, Berlin 1977, p. 505).

The compounds of the formula (XXVII) are novel. They can be prepared by processes known in principle and as shown in the examples (see, for example, H. Henecka, Houben-Weyl, Methoden der Organischen Chemie [Methods of Organic Chemistry], Vol. 8, pp. 467-469 (1952)).

The compounds of the formula (XXVII) are obtained, for example, when substituted phenylacetic acids of the formula (XXX)

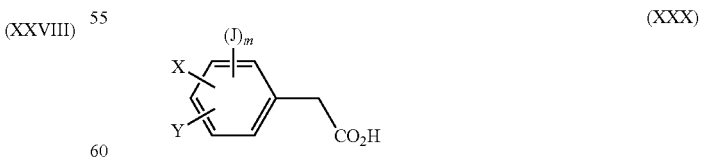
(XXX)

in which
J, m, X and Y are as defined above
are reacted with halogenating agents (for example thionyl chloride, thionyl bromide, oxalyl chloride, phosgene, phosphorus trichloride, phosphorus tribromide or phosphorus pentachloride), phosphonylating agents (such as, for example, POCl$_3$, BOP—Cl), carbonyldiimidazole, carbodiimides (for example dicyclohexylcarbodiimide), if appropriate in the presence of a diluent (for example optionally chlorinated aliphatic or aromatic hydrocarbons, such as toluene or methylene chloride, or ethers, for example tetrahydrofuran, dioxane, methyl tert-butyl ether), at temperatures of from −20° C. to 150° C., preferably from −10° C. to 100° C.

Some of the compounds of the formulae (XXVI) and (XXIX) are known from the patent literature cited at the outset, and/or they can be prepared by known processes (see, for example, Compagnon, Miocque Ann. Chim. (Paris) 5, pp. 11-22, 23-27 (1970)).

The substituted cyclic aminocarboxylic acids of the formula (XXIX) in which A and B form a ring are generally obtainable by the Bucherer-Bergs synthesis or by the Strecker synthesis, where they are obtained in each case in different isomeric forms. Thus, the conditions of the Bucherer-Bergs synthesis afford predominantly the isomers (hereinbelow for the sake of simplicity referred to as β) in which the radicals R and the carbonyl group are in equatorial positions, whereas the conditions of the Strecker synthesis afford predominantly the isomers (hereinbelow for the sake of simplicity referred to as α) in which the amino group and the radicals R are in equatorial positions.

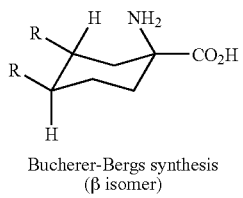  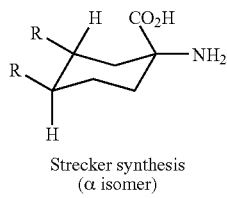

Bucherer-Bergs synthesis (β isomer)    Strecker synthesis (α isomer)

(L. Munday, J. Chem. Soc. 4372 (1961); J. T. Eward, C. Jitrangeri, Can. J. Chem. 53, 3339 (1975).

The starting materials, used in the above process (A), of the formula (II)

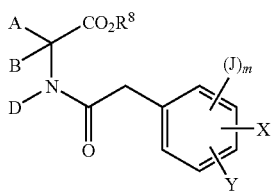

(II)

in which
A, B, D, J, m, X, Y and R$^8$ are as defined above
can furthermore be prepared by reacting aminonitriles of the formula (XXXI)

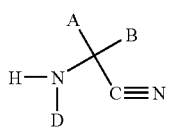

(XXXI)

in which
A, B and D are as defined above
with substituted phenylacetic acid derivatives of the formula (XXVII)

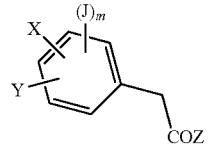

(XXVII)

in which
J, m, X, Y and Z are as defined above
to give compounds of the formula (XXXII)

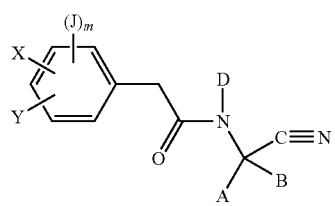

(XXXII)

in which
A, B, D, J, m, X and Y are as defined above,
and then subjecting these to an acidic alcoholysis.

The compounds of the formula (XXXII) are likewise novel.

The compounds, required as starting materials in the process (B) according to the invention, of the formula (III)

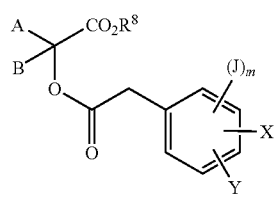

(III)

in which
A, B, J, m, X, Y and R$^8$ are as defined above are novel.

They can be prepared by methods known in principle.

Thus, the compounds of the formula (III) are obtained, for example, when 2-hydroxycarboxylic esters of the formula (XXXIII-A)

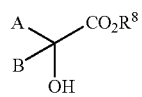

(XXXIII-A)

in which

A, B and R$^8$ are as defined above
are acylated with substituted phenylacetic acid derivatives of the formula (XXVII)

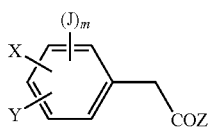
(XXVII)

in which
J, m, X, Y and Z are as defined above
(Chem. Reviews 52, 237-416 (1953)).

Furthermore, compounds of the formula (III) are obtained when substituted phenylacetic acids of the formula (XXX)

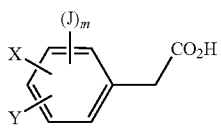
(XXX)

in which
J, m, X and Y are as defined above
are alkylated with α-halocarboxylic esters of the formula (XXXIII-B)

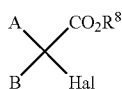
(XXXIII-B)

in which
A, B and $R^8$ are as defined above and
Hal represents chlorine or bromine.

Some of the compounds of the formula (XXXIII) are commercially available, some are known; however, some are also novel.

The compounds of the formula (XXXIII-B) are commercially available.

The compounds of the formula (XXX) are novel.

The compounds of the formula (XXX),

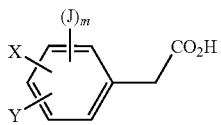
(XXX)

in which
J, m, X and Y are as defined above
are obtained, for example, when phenylacetic esters of the formula (XXXIV)

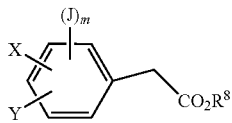
(XXXIV)

in which
J, m, X, Y and $R^8$ are as defined above are hydrolysed in the presence of acids or bases, in the presence of a solvent under generally known standard conditions.

The compounds of the formula (XXXIV) are novel.

The compounds of the formula (XXXIV)

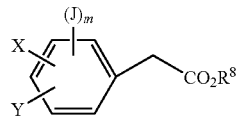
(XXXIV)

in which
J, m, X, Y and $R^8$ are as defined above
are obtained by the process described in the examples analogously to process (R) when phenylacetic esters of the formula (XXXIV-a)

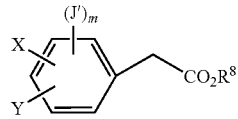
(XXXIV-a)

in which
$R^8$, m, X and Y are as defined above
and J' represents bromine or iodine
are reacted in the presence of cycloalkylboronic acid derivatives capable of coupling, for example cyclopropaneboronic acid, in the presence of a base and, if appropriate, in the presence of a catalyst (preferably palladium salts and a complex former, such as, for example, palladium acetate/tricyclohexylphosphine).

The phenylacetic esters of the formula (XXXIV-a) are known in principle, for example from the laid-open applications WO 96/35 664, WO 97/02243, WO 97/01535, WO 98/05638 and DE-A-10 301 804, and they can be prepared by the processes described in these publications.

The compounds, required as starting materials for the process (C) above, of the formula (IV)

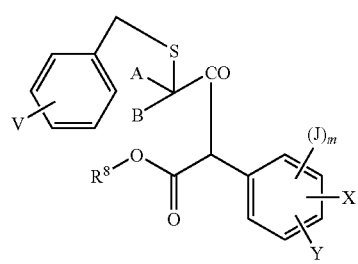
(IV)

in which
A, B, J, m, V, X, Y and $R^8$ are as defined above
are novel.

They can be prepared by methods known in principle.

The compounds of the formula (IV) are obtained, for example, when substituted phenylacetic esters of the formula (XXXIV)

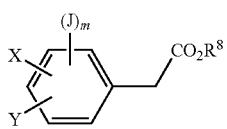

(XXXIV)

in which
J, m, X, Y and R$^8$ are as defined above
are acylated with 2-benzylthiocarbonyl halides of the formula (XXXV)

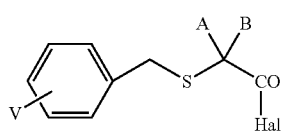

(XXXV)

in which
A, B and V are as defined above and
Hal represents halogen (in particular chlorine or bromine)
in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXV) are known, and/or they can be prepared by known processes (J. Antibiotics (1983), 26, 1589).

The halocarbonyl ketenes of the formula (VI) required as starting materials for the above processes (D), (E) and (H-α) are novel. They can be prepared by methods known in principle (cf., for example, Org. Prep. Proced. Int., 7, (4), 155-158, 1975 and DE 1 945 703). Thus, for example, the compounds of the formula (VI)

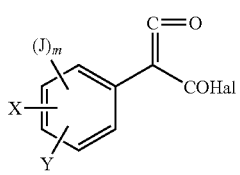

(VI)

in which
J, m, X and Y are as defined above and
Hal represents chlorine or bromine
are obtained when
substituted phenylmalonic acids of the formula (XXXVI)

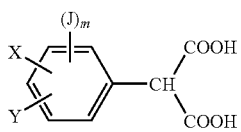

(XXXVI)

in which
J, m, X and Y are as defined above
are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, dimethylformamide, methylstearylformamide or triphenylphosphine, and, if appropriate, in the presence of bases, such as, for example, pyridine or triethylamine.

The substituted phenylmalonic acids of the formula (XXXVI) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (XXXVI)

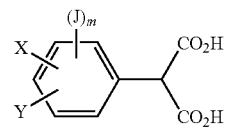

(XXXVI)

in which
J, m, X and Y are as defined above
are obtained when phenylmalonic esters of the formula (XI)

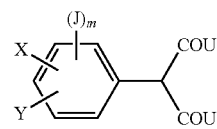

(XI)

in which
J, m, X and Y are as defined above
and U represents OR$^8$,
where R$^8$ is as defined above,
are initially hydrolysed in the presence of a base and of a solvent and then carefully acidified (see, for example, EP-A-528 156, WO 96/35 664, WO 97/02 243).

The malonic esters of the formula (XI)

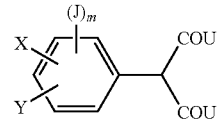

(XI)

in which
J, m, X and Y are as defined above
and U represents OR$^8$,
where R$^8$ is as defined above,
are novel.

They can be prepared by generally known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds, required as starting materials for the process (D) according to the invention, of the formula (V)

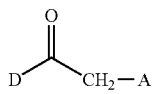
(V)

in which

A and D are as defined above or silylenol ethers thereof of the formula (Va)

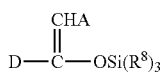
(Va)

in which

A, D and $R^8$ are as defined above are commercially available compounds, generally known compounds or compounds which can be obtained by known processes.

The preparation of the ketene acid chlorides of the formula (VI), required as starting materials for carrying out the process (E) according to the invention, have already been described above. The thioamides, required for carrying out the process (E) according to the invention, of the formula (VII)

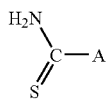
(VII)

in which

A is as defined above are compounds which are generally known in organic chemistry.

The compounds, required as starting materials in the above process (F), of the formula (VIII)

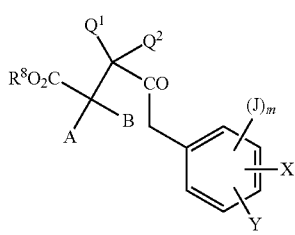
(VIII)

in which

A, B, J, m, $Q^1$, $Q^2$, X, Y and $R^8$ are as defined above are novel.

They can be prepared by methods known in principle.

The 5-aryl-4-ketocarboxylic esters of the formula (VIII) are obtained, for example, when 5-aryl-4-ketocarboxylic acids of the formula (XXXVII)

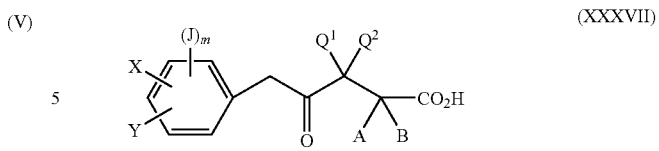
(XXXVII)

in which

J, m, X, Y, A, B, $Q^1$ and $Q^2$ are as defined above are esterified (cf., for example, Organikum, 15th edition, Berlin, 1977, page 499) or alkylated (see Preparation Example)

The 5-aryl-4-ketocarboxylic acids of the formula (XXXVII)

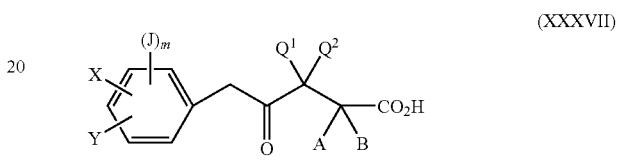
(XXXVII)

in which

A, B, J, m, $Q^1$, $Q^2$, X and Y are as defined above are novel; however, they can be prepared by methods known in principle (WO 96/01 798, WO 97/14667, WO 98/39281).

The 5-aryl-4-ketocarboxylic acids of the formula (XXX-VII) are obtained, for example, when 2-phenyl-3-oxoadipic esters of the formula (XXXVIII)

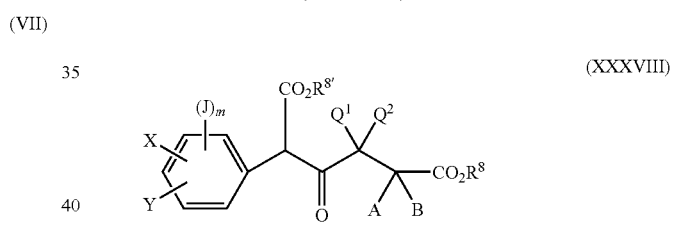
(XXXVIII)

in which

A, B, J, m, $Q^1$, $Q^2$, X and Y are as defined above and $R^8$ and $R^{8'}$ represent alkyl (in particular $C_1$-$C_8$-alkyl) and, when the compound of the formula (XL-a) is used, $R^8$ represents hydrogen, are decarboxylated, if appropriate in the presence of a diluent and if appropriate in the presence of a base or an acid (cf., for example, Organikum, 15th edition, Berlin, 1977, pages 519 to 521, WO 96/01798, WO 97/14667, WO 98/39281). The compounds of the formula (XXXVIII)

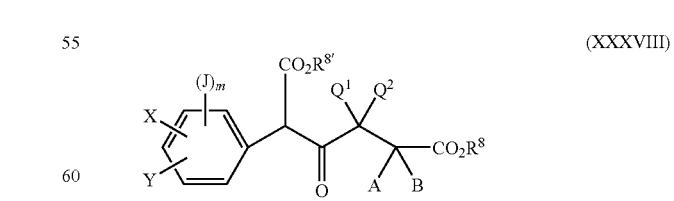
(XXXVIII)

in which

A, B, J, m, $Q^1$, $Q^2$, X, Y, $R^8$, $R^{8'}$ are as defined above and, when the compound of the formula (XL-a) is used, $R^8$ represents hydrogen, are novel.

The compounds of the formula (XXXVIII) are obtained, for example,
when dicarboxylic monoester chlorides of the formula (XXXIX),

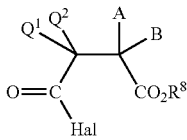
(XXXIX)

in which
A, B, $Q^1$, $Q^2$ and $R^8$ are as defined above and
Hal represents chlorine or bromine
or carboxylic anhydrides of the formula (XL-a)

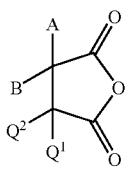
(XL-a)

in which
A, B, $Q^1$ and $Q^2$ are as defined above
are acylated with a phenylacetic ester of the formula (XXXIV)

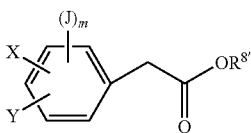
(XXXIV)

in which
J, m, X, Y and $R^{8'}$ are as defined above
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XXXIX) and (XL-a) are known compounds of organic chemistry, and/or they can be prepared in a simple manner by methods known in principle.

The compounds, required as starting materials in the above process (G), of the formula (IX)

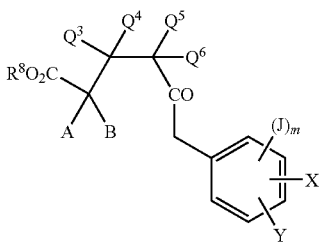
(IX)

in which
A, B, J, m, $Q^3$, $Q^4$, $Q^5$, $Q^6$, X, Y and $R^8$ are as defined above,
are novel.

They can be prepared by methods known in principle.

The 6-aryl-5-ketocarboxylic esters of the formula (IX) are obtained, for example, when 6-aryl-5-ketocarboxylic acids of the formula (XLI)

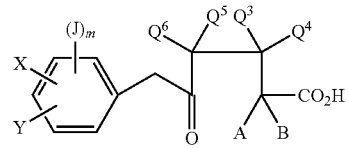
(XLI)

in which
A, B, J, m, $Q^3$, $Q^4$, $Q^5$, $Q^6$, X and Y are as defined above
are esterified (cf., for example, Organikum, 15th edition, Berlin, 1977, page 499, WO 99/43649, WO 99/48869).

The 6-aryl-5-ketocarboxylic acids of the formula (XLI)

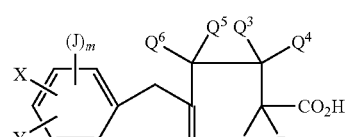
(XLI)

in which
A, B, J, m, $Q^3$, $Q^4$, $Q^5$, $Q^6$, X and Y are as defined above
are novel. They can be prepared by methods known in principle (WO 99/43649, WO 99/48869), for example when
substituted 2-phenyl-3-oxoheptanedioic esters of the formula (XLII)

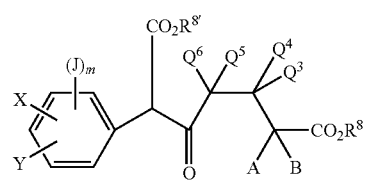
(XLII)

in which
A, B, J, m, $Q^3$, $Q^4$, $Q^5$, $Q^6$, X and Y are as defined above and
$R^8$ and $R^{8'}$ represent alkyl (preferably $C_1$-$C_6$-alkyl) and,
when the compound of the formula (XL-b) is used, $R^8$ represents hydrogen
are hydrolysed and decarboxylated, if appropriate in the presence of a diluent and if appropriate in the presence of a base or an acid (cf., for example, Organikum, 15th edition, Berlin, 1977, pages 519 to 521, WO 99/43649, WO 99/48869).

The compounds of the formula (XLII)

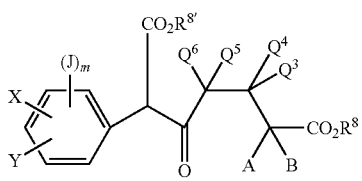
(XLII)

in which
A, B, J, m, $Q^3$, $Q^4$, $Q^5$, $Q^6$, X, Y, $R^8$ and $R^{8'}$ are as defined above
are novel and can be obtained
when dicarboxylic esters of the formula (XLIII),

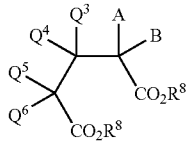
(XLIII)

in which
A, B, $Q^3$, $Q^4$, $Q^5$, $Q^6$ and $R^8$ are as defined above
or carboxylic anhydrides of the formula (XL-b)

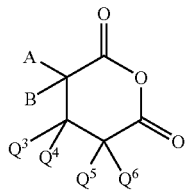
(XL-b)

in which A, B, $Q^3$, $Q^4$, $Q^5$, $Q^6$ are as defined above
are condensed with a substituted phenylacetic ester of the formula (XXXIV)

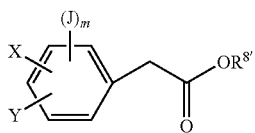
(XXXIV)

in which
J, m, X, Y and $R^{8'}$ are as defined above
in the presence of a diluent and in the presence of a base.

Some of the compounds of the formula (XLIII) are known, and/or they can be prepared by known processes.

Some of the hydrazines, required as starting materials for the processes (H-α) and (H-β) according to the invention, of the formula (X)

A-NH—NH-D (X)

in which
A and D are as defined above
are known, and/or they can be prepared by methods known from the literature (cf., for example, Liebigs Ann. Chem. 585, 6 (1954); Reaktionen der organischen Synthese [Reactions of Organic Synthesis], C. Ferri, pages 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds, required for the process (H-γ) according to the invention, of the formula (XII)

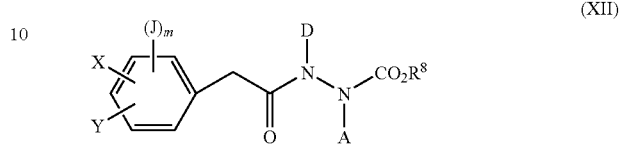
(XII)

in which
A, D, J, m, X, Y and $R^8$ are as defined above
are novel.

The acylcarbazates of the formula (XII) are obtained, for example, when carbazates of the formula (XLIV)

(XLIV)

in which
A, $R^8$ and D are as defined above
are acylated with substituted phenylacetic acid derivatives of the formula (XXVII)

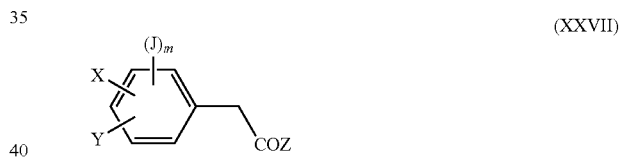
(XXVII)

in which
J, m, X, Y and Z are as defined above
(Chem. Reviews 52, 237-416 (1953); Bhattacharya, Indian J. Chem. 6, 341-5, 1968).

Some of the carbazates of the formula (XLIV) are commercially available compounds and some are known compounds, or they can be prepared by processes of organic chemistry known in principle.

The compounds of the formula (XXVII) have already been described in connection with the precursors for the processes (A) and (B).

The compounds, required as starting materials for the process (I) according to the invention, of the formula (XIII)

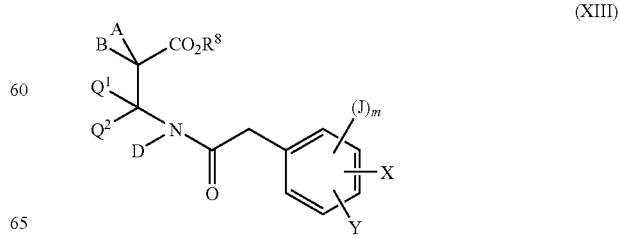
(XIII)

in which
A, B, D, J, m, $Q^1$, $Q^2$, X, Y and $R^8$ are as defined above, are novel.

The acylamino acid esters of the formula (XIII) are obtained, for example, when amino acid derivatives of the formula (XLV)

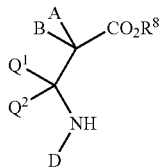
(XLV)

in which
A, B, $Q^1$, $Q^2$, $R^8$ and D are as defined above
are acylated with substituted hetarylacetic acid derivatives of the formula (XXVII)

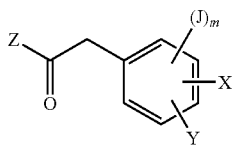
(XXVII)

in which
J, m, X, Y and Z are as defined above
(Chem. Reviews 52, 237-416 (1953); Bhattacharya, Indian J. Chem. 6, 341-5, 1968)
or when acylamino acids of the formula (LXVI)

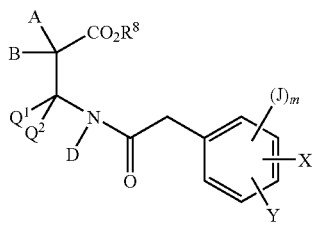
(LXVI)

in which
A, B, J, m, D, $Q^1$, $Q^2$, X and Y are as defined above
are esterified (Chem. Ind. (London) 1568 (1968)).

The compounds of the formula (LXVI)

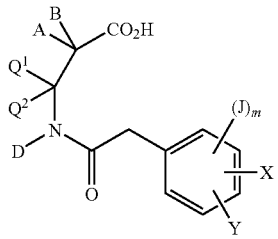
(LXVI)

in which
A, B, D, J, m, $Q^1$, $Q^2$, X and Y are as defined above
are novel.

The compounds of the formula (XLVI) are obtained when β-amino acids of the formula (XLVII)

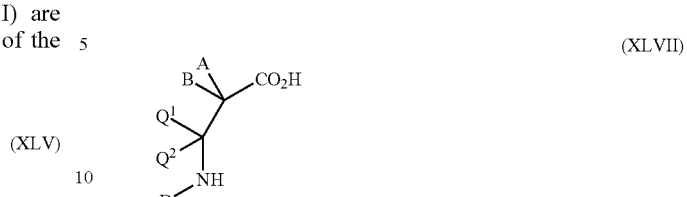
(XLVII)

in which
A, B, $Q^1$, $Q^2$ and D are as defined above
are acylated with substituted phenylacetic acid derivatives of the formula (XXVII)

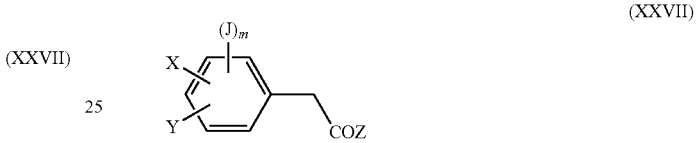
(XXVII)

in which
J, m, X, Y and Z are as defined above, for example according to Schotten-Baumann (Organikum, VEB Deutscher Verlag der Wissen-schaften, Berlin 1977, p. 505).

The compounds of the formula (XXVII) are novel. They can be prepared by processes known in principle (see, for example, H. Henecka, Houben-Weyl, Methoden der Organischen Chemie, Vol. 8, pp. 467-469 (1952), WO 97/02243, WO 99/43699), or they are generated in situ using the reagents listed above.

Some of the compounds of the formulae (XLV) and (XLVII) are known from WO 01/79204, or they can be prepared by the process, known in principle, given in this publication.

The compounds, required as starting materials for the process (J) according to the invention, of the formula (XIV)

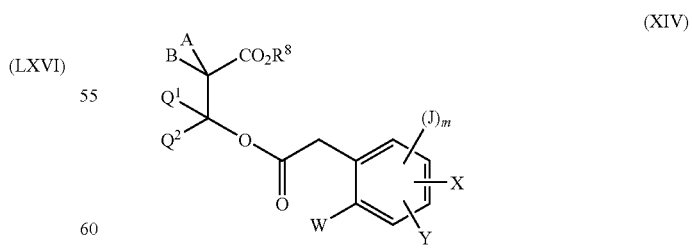
(XIV)

in which
A, B, J, m, $Q^1$, $Q^2$, X, Y and $R^8$ are as defined above,
are novel.

The acylhydroxycarboxylic esters of the formula (XIV) are obtained, for example, when hydroxycarboxylic esters of the formula (XLVIII)

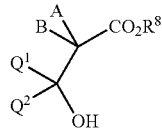
(XLVIII)

in which
A, B, Q¹, Q² and R⁸ are as defined above
are acylated with substituted phenylacetic acid derivatives of the formula (XXVII)

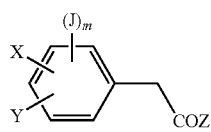
(XXVII)

in which
J, m, X, Y and Z are as defined above
(see Preparation Examples of formula (II)).

Some of the compounds of the formula (XLVIII) are known from WO 01/98288, or they can be prepared by processes known in principle, for example by the Reformatskij synthesis (Organikum, VEB Deutscher Verlag der Wissenschaften, Berlin 1990, 18th ed., p. 501 ff.)

The compounds of the formula (XXVII) are novel. They can be prepared by processes known in principle (see for example, H. Henecka, Houben-Weyl, Methoden der Organischen Chemie, Vol. 8, pp. 467-469 (1952), WO 97/02243, WO 99/43649).

The acid halides of the formula (XV), carboxylic anhydrides of the formula (XVI), chloroformic esters or chloroformic thioesters of the formula (XVII), chloromonothioformic esters or chlorodithioformic esters of the formula (XVIII), sulphonyl chlorides of the formula (XIX), phosphorus compounds of the formula (XX) and metal hydroxides, metal alkoxides or amines of the formulae (XXI) and (XXII) and isocyanates of the formula (XXIII) and carbamoyl chlorides of the formula (XXIV) and also cycloalkylboronic acid derivatives (XXV) furthermore required as starting materials for carrying out the processes (K), (L), (M), (N), (O), (P), (Q) and (R) according to the invention are generally known compounds of organic or inorganic chemistry.

In addition, the compounds of the formulae (V), (VII), (X), (XXVI), (XXIX), (XXXI), (XXXIII-A), (XXXIII-B), (XXXV), (XXXIX), (XL-a), (XL-b), (XLIII), (XLIV), (XLV), (XLVII) and (XLVIII) are furthermore known from the patent applications cited at the outset, and/or they can be prepared by the methods given in these publications.

The process (A) is characterized in that compounds of the formula (II) in which A, B, D, J, m, X, Y and R⁸ are as defined above are subjected to an intramolecular condensation in the presence of a base.

Suitable for use as diluents in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately doubly equimolar amounts. However, it is also possible to use a relatively large excess (up to 3 mol) of one or the other component.

The process (B) is characterized in that compounds of the formula (III) in which A, B, J, m, X, Y and R⁸ are as defined above are subjected to an intramolecular condensation in the presence of a diluent and in the presence of a base.

Suitable for use as diluents in the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (II) and the deprotonating bases are generally employed in approximately equimolar amounts. However, it is also possible to use a relatively large excess (up to 3 mol) of one or the other component.

The process (C) is characterized in that compounds of the formula (IV) in which A, B, V, J, m, X, Y and $R^8$ are as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

If appropriate, the acid used may also serve as diluent.

Suitable for use as acid in the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the process is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are, for example, employed in equimolar amounts. However, it is also possible, if appropriate, to use the acid as solvent or as catalyst.

The process (D) according to the invention is characterized in that carbonyl compounds of the formula (V) or their enole ethers of the formula (V-a) are reacted with ketene acid halides of the formula (VI) in the presence of a diluent and, if appropriate, in the presence of an acid acceptor.

Suitable diluents for use in the process (D) according to the invention are all inert organic solvents. Preference is given to using optionally halogenated hydrocarbons, such as toluene, xylene, mesitylene, chlorobenzene and dichlorobenzene, furthermore ethers, such as dibutyl ether, glycol dimethyl ether, diglycol dimethyl ether and diphenyl ether, moreover polar solvents, such as dimethyl sulphoxide, sulpholane, dimethylformamide or N-methylpyrrolidone.

Suitable acid acceptors for carrying out the process variant (D) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (D) according to the invention, the reaction temperatures can be varied within a relatively wide range. Expediently, the process is carried out at temperatures between 0° C. and 250° C., preferably between 50° C. and 220° C.

The process (D) according to the invention is expediently carried out under atmospheric pressure.

When carrying out the process (D) according to the invention, the reaction components of the formulae (V) and (VI), in which A, D, J, m, X and Y are as defined above and Hal represents halogen, and, if appropriate, the acid acceptors are generally employed in approximately equimolar amounts. However, it is also possible to use a relatively large excess (up to 5 mol) of one component or the other.

The process (E) according to the invention is characterized in that thioamides of the formula (VII) are reacted with ketene acid halides of the formula (VI) in the presence of a diluent and, if appropriate, in the presence of an acid acceptor.

Suitable for use as diluents for the process variant (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methylpyrrolidone.

Suitable for use as acid acceptors for carrying out the process (E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process (E) according to the invention, the reaction temperatures can be varied within a relatively wide range. Expediently, the process is carried out at temperatures between 0° C. and 250° C., preferably between 20° C. and 220° C.

The process (E) according to the invention is expediently carried out under atmospheric pressure.

When carrying out the process (E) according to the invention, the reaction components of the formulae (VII) and (VI), in which A, J, m, X and Y are as defined above and Hal represents halogen, and, if appropriate, the acid acceptors are generally employed in approximately equimolar amounts. However, it is also possible to use a relatively large excess (up to 5 mol) of one component or the other.

The process (F) is characterized in that compounds of the formula (VIII) in which A, B, J, m, $Q^1$, $Q^2$, X, Y and $R^8$ are as defined above are subjected to an intramolecular condensation in the presence of a base.

Suitable diluents for use in the process (F) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (F) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (F) according to the invention, the reaction temperatures can be varied within a relatively wide range. In general, the process is carried out at temperatures between −75° C. and 250° C., preferably between −50° C. and 150° C.

The process (F) according to the invention is generally carried out under atmospheric pressure.

When carrying out the process (F) according to the invention, the reaction components of the formula (VIII) and the deprotonating bases are generally employed in approximately equimolar amounts. However, it is also possible to use a relatively large excess (up to 3 mol) of one or the other component.

The process (G) is characterized in that compounds of the formula (IX) in which A, B, $Q^3$, $Q^4$, $Q^5$, $Q^6$, J, m, X, Y and $R^8$ are as defined above are subjected to an intramolecular condensation in the presence of bases.

Suitable diluents for use in the process (G) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (G) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (G) according to the invention, the reaction temperatures can be varied within a relatively wide range. In general, the process is carried out at temperatures between 0° C. and 250° C., preferably between 50° C. and 150° C.

The process (G) according to the invention is generally carried out under atmospheric pressure.

When carrying out the process (G) according to the invention, the reaction components of the formula (IX) and the deprotonating bases are generally employed in approximately equimolar amounts. However, it is also possible to use a relatively large excess (up to 3 mol) of one or the other component.

The process (H-α) according to the invention is characterized in that hydrazines of the formula (X) or salts of these compounds are reacted with ketene acid halides of the formula (VI) in the presence of a diluent and, if appropriate, in the presence of an acid acceptor.

Suitable diluents for use in the process (H-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenylethane, moreover polar solvents, such as dimethyl sulphoxide, sulpholane, dimethylformamide or N-methylpyrrolidone.

Suitable acid acceptors for carrying out the process variant (H-α) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (H-α) according to the invention, the reaction temperatures can be varied within a relatively wide range. Expediently, the process is carried out at temperatures between 0° C. and 250° C., preferably between 50° C. and 220° C.

The process (H-α) according to the invention is expediently carried out under atmospheric pressure.

When carrying out the process (H-α) according to the invention, the reaction components of the formulae (VI) and (X), in which A, D, J, m, X and Y are as defined above and Hal represents halogen, and, if appropriate, the acid acceptors are generally employed in approximately equimolar amounts. However, it is also possible to use a relatively large excess (up to 5 mol) of one component or the other.

The process (H-β) is characterized in that hydrazines of the formula (X) or salts of this compound, in which A and D are as defined above, are subjected to a condensation with malonic esters or malonamides of the formula (XI) in which U, J, m, X, Y and $R^8$ are as defined above, in the presence of a base.

Suitable diluents for use in the process (H-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetrahydrofuran, dioxane, diphenyl ether, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (H-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyl-trialkyl($C_9$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

It is also possible to use tertiary amines, such as triethylamine, pyridine, diazabicyclooctane (DABCO), diazabicycloundecane (DBU), diazabicyclononene (DBN), Hünig base and N,N-dimethylaniline.

When carrying out the process (H-β) according to the invention, the reaction temperatures can be varied within a relatively wide range. In general, the process is carried out at temperatures between 0° C. and 280° C., preferably between 50° C. and 180° C.

The process (H-β) according to the invention is generally carried out under atmospheric pressure.

When carrying out the process (H-β) according to the invention, the reaction components of the formulae (XI) and (X) are generally employed in approximately equimolar amounts. However, it is also possible to use a relatively large excess (up to 3 mol) of one component or the other.

The process (H-γ) is characterized in that compounds of the formula (XII) in which A, D, J, m, X, Y and $R^8$ are as defined above are subjected to an intramolecular condensation in the presence of a base.

Suitable for use as diluents in the process (H-γ) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (H-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyl-trialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (H-γ) according to the invention, the reaction temperatures can be varied within a relatively wide range. In general, the process is carried out at temperatures between 0° C. and 250° C., preferably between 50° C. and 150° C.

The process (H-γ) according to the invention is generally carried out under atmospheric pressure.

When carrying out the process (H-γ) according to the invention, the reaction components of the formula (XII) and the deprotonating bases are generally employed in approximately doubly equimolar amounts. However, it is also possible to use a relatively large excess (up to 3 mol) of one or the other component.

The process (I) is characterized in that compounds of the formula (XIII) in which A, B, D, J, m, $Q^1$, $Q^2$, X, Y and $R^8$ are as defined above are subjected to an intramolecular condensation in the presence of a base.

Suitable for use as diluents in the process (I) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (I) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (I) according to the invention, the reaction temperatures can be varied within a relatively wide range. In general, the process is carried out at temperatures between −80° C. and 180° C., preferably between −50° C. and 120° C.

The process (I) according to the invention is generally carried out under atmospheric pressure.

When carrying out the process (I) according to the invention, the reaction components of the formula (XIII) and the deprotonating bases are generally employed in approximately doubly equimolar amounts. However, it is also possible to use a relatively large excess (up to 3 mol) of one or the other components.

The process (J) is characterized in that compounds of the formula (XIV) in which A, B, $Q^1$, $Q^2$, J, m, X, Y and $R^8$ are as defined above, are subjected to an intramolecular condensation in the presence of a base.

Suitable for use as diluents in the process (J) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (J) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyl-trialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (J) according to the invention, the reaction temperatures can be varied within a relatively wide range. In general, the process is carried out at temperatures between 0° C. and 250° C., preferably between 50° C. and 150° C.

The process (J) according to the invention is generally carried out under atmospheric pressure.

When carrying out the process (J) according to the invention, the reaction components of the formula (XIV) and the deprotonating bases are generally employed in approximately equimolar amounts. However, it is also possible to use a relatively large excess (up to 3 mol) of one or the other component.

The process (K-α) is characterized in that compounds of the formulae (I-1-a) to (I-10-a) are in each case reacted with carbonyl halides of the formula (XV), if appropriate in the presence of a diluent and if appropriate in the presence of an acid binder.

Suitable diluents for use in the process (K-α) according to the invention are all solvents which are inert toward the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction according to the process (K-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (K-α) according to the invention may be varied within a relatively wide range. In general, the process is carried out at temperatures between −20° C. and +150° C., preferably between 0° C. and 100° C.

When carrying out the process (K-α) according to the invention, the starting materials of the formulae (I-1-a) to (I-10-a) and the carbonyl halide of the formula (XV) are generally each employed in approximately equivalent amounts. However, it is also possible to use a relatively large excess (up to 5 mol) of the carbonyl halide. Work-up is carried out by customary methods.

The process (K-β) is characterized in that compounds of the formulae (I-1-a) to (I-10-a) are reacted with carboxylic anhydrides of the formula (XVI), if appropriate in the presence of a diluent and if appropriate in the presence of an acid binder.

Suitable for use as diluents in the process (K-β) according to the invention are, preferably, those diluents which are also preferred when acid halides are used. Besides, it is also possible for excess carboxylic anhydride to act simultaneously as diluent.

Suitable acid binders for process (K-β), which are added, if appropriate, are preferably those acid binders which are also preferred when acid halides are used.

The reaction temperatures in the process (K-β) according to the invention can be varied within a relatively wide range. In general, the process is carried out at temperatures between −20° C. and +150° C., preferably between 0° C. and 100° C.

When carrying out the process (K-β) according to the invention, the starting materials of the formulae (I-1-a) to (I-10-a) and the carboxylic anhydride of the formula (XVI) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (L) is characterized in that compounds of the formulae (I-1-a) to (I-10-a) are in each case reacted with chloroformic esters or chloroformic thioesters of the formula (XVII), if appropriate in the presence of a diluent and if appropriate in the presence of an acid binder.

Suitable acid binders for the reaction according to process (L) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (L) according to the invention are all solvents which are inert toward the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (L) according to the invention, the reaction temperatures can be varied within a relatively wide range. If the reaction is carried out in the presence of a diluent and an acid binder, reaction temperatures are generally between −20° C. and +100° C., preferably between 0° C. and 50° C.

The process (L) according to the invention is generally carried out under atmospheric pressure.

When carrying out the process (L) according to the invention, the starting materials of the formulae (I-1-a) to (I-10-a) and the appropriate chloroformic ester or chloroformic thioester of the formula (XVII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (M) according to the invention is characterized in that compounds of the formulae (I-1-a) to (I-10-a) are in each case reacted with compounds of the formula (XVIII) in the presence of a diluent and, if appropriate, in the presence of an acid binder.

In preparation process (M), about 1 mol of chloromonothioformic ester or chlorodithioformic ester of the formula (XVIII) is reacted per mole of the starting material of the formulae (I-1-a) to (I-10-a) at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-10-a) is prepared by addition of strong deprotonating agents, such as, for example, sodium hydride or potassium tert-butoxide, the further addition of acid binders may be dispensed with.

If acid binders are used, customary inorganic or organic bases are suitable, by way of example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (N) according to the invention is characterized in that compounds of the formulae (I-1-a) to (I-10-a) are in each case reacted with sulphonyl chlorides of the formula (XIX), if appropriate in the presence of a diluent and if appropriate in the presence of an acid binder. In preparation process (N), about 1 mol of sulphonyl chloride of the formula (XIX) is reacted per mole of starting material of the formula (I-1-a to I-10-a), at from −20 to 150° C., preferably from 20 to 70° C.

Suitable diluents, which are added, if appropriate, are all inert polar organic solvents, such as ethers, amides, nitrites, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-10-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (O) according to the invention is characterized in that compounds of the formulae (I-1-a) to (I-10-a) are in each case reacted with phosphorus compounds of the formula (XX), if appropriate in the presence of a diluent and if appropriate in the presence of an acid binder.

In preparation process (O), to obtain compounds of the formulae (I-1-e) to (I-10-e) 1 to 2, preferably 1 to 1.3, mol of the phosphorus compound of the formula (XX) are employed per mole of the compounds (I-1-a) to (I-10-a), at temperatures between −40° C. and 150° C., preferably between −10 and 110° C.

Suitable diluents which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders, which are added if appropriate, are customary inorganic or organic bases, such as hydroxides, carbonates or amines. Sodium hydroxide, sodium carbonate, potassium carbonate, pyridine, triethylamine may be mentioned by way of example.

The reaction can be carried out at atmospheric pressure or under elevated pressure and is preferably carried out at atmospheric pressure. Work-up is carried out by customary methods of organic chemistry. The end products obtained are preferably purified by crystallization, chromatographic purification or by so-called "incipient distillation", i.e. removal of the volatile components under reduced pressure.

The process (P) is characterized in that compounds of the formulae (I-1-a) to (I-10-a) are reacted with metal hydroxides or metal alkoxides of the formula (XXI) or amines of the formula (XXII), if appropriate in the presence of a diluent.

Suitable for use as diluents in the process (P) according to the invention are, preferably, ethers, such as tetrahydrofuran, dioxane, diethyl ether, or else alcohols, such as methanol, ethanol, isopropanol, but also water.

The process (P) according to the invention is generally carried out under atmospheric pressure.

The reaction temperatures are generally between −20° C. and 100° C., preferably between 0° C. and 50° C.

The process (Q) according to the invention is characterized in that compounds of the formulae (I-1-a) to (I-10-a) are in each case reacted with (Q-α) compounds of the formula (XXIII), if appropriate in the presence of a diluent and if appropriate in the presence of a catalyst, or (Q-β) with compounds of the formula (XXIV), if appropriate in the presence of a diluent and if appropriate in the presence of an acid binder.

In preparation process (Q-α), about 1 mol of isocyanate of the formula (XXIII) is employed per mole of starting material of the formulae (I-1-a) to (I-10-a), at from 0 to 100° C., preferably from 20 to 50° C.

Suitable diluents, which are added, if appropriate, are all inert organic solvents, such as ethers, amides, nitrites, sulphones, sulphoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (Q-β), about 1 mol of carbamoyl chloride of the formula (XXIV) is employed per mole of starting material of the formulae (I-1-a) to (I-10-a) at from −20 to 150° C., preferably from 0 to 70° C.

Suitable diluents, which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-10-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, triethylamine or pyridine.

The reaction may be carried out at atmospheric pressure or under elevated pressure and is preferably carried out at atmospheric pressure. Work-up is carried out by customary methods.

Suitable catalysts for carrying out the process (R) according to the invention are palladium(0) complexes. Preference is given, for example, to tetrakis(triphenylphosphine)palladium. If appropriate, it is also possible to use palladium(II) compounds, for example $PdCl_2$, $Pd(OAC)_2$. If palladium(II)

compounds are used, phosphines, such as, for example, tricyclohexylphosphine, are generally employed as complex formers.

Suitable acid acceptors for carrying out the process (R) according to the invention are inorganic or organic bases. These preferably include alkaline earth metal or alkali metal hydroxides, acetates, carbonates or bicarbonates, such as; for example, sodium hydroxide, potassium hydroxide, barium hydroxide or ammonium hydroxide, sodium acetate, potassium acetate, calcium acetate or ammonium acetate, sodium carbonate, potassium carbonate, caesium carbonate or ammonium carbonate, sodium bicarbonate or potassium bicarbonate, alkali metal fluorides, such as, for example, caesium fluoride, alkali metal phosphates, such as, for example, potassium dihydrogen phosphate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicyclo-undecene (DBU).

Suitable diluents for carrying out the process (R) according to the invention are water, organic solvents and any mixtures thereof. The following may be mentioned by way of example: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisoproypl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monomethyl ether; water.

In the process (R) according to the invention, the reaction temperature can be varied within a relatively wide range. In general, the process is carried out at temperatures between 0° C. and +140° C., preferably between 50° C. and +100° C.

When carrying out the process (R) according to the invention, the boronic acids of the formula (XXV), in which J is as defined above and the compounds of the formulae (I-1') to (I-10'), in which A, B, D, G, m, $Q^1$, $Q^2$, $Q^3$, $Q^4$, $Q^5$, $Q^6$, X, Y, and J' are as defined above are employed in a molar ratio of from 1:1 to 3:1, preferably from 1:1 to 2:1. In general from 0.005 to 0.5 mol, preferably from 0.01 mol of 0.1 mol, of catalyst are employed per mole of the compounds of the formulae (I-1') to (I-10'). The base is generally employed in excess.

The inventive active compounds/active compound combinations, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the *Dermaptera*, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa*.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Clcadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus dipsaci, Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds/active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds/active compound combinations is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds/active compound combinations can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds/active compound combinations with extenders, that is liquid solvents and/or solid carriers, optionally with the use of surfactants, that is emulsifiers and/or dispersants and/or foam-formers.

If the extender used is water, it is also possible to use organic solvents, for example, as auxiliary solvents. Suitable liquid solvents are essentially aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone or cyclohexanone, strongly polar solvents, such as dimethyl sulphoxide, and also water.

Suitable solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils. It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound/active compound combinations according to the invention can be present in their commercially available formulations, as well as in the use forms prepared from these formulations, in a mixture with other active compounds such as insecticides, attractants, sterilizers, bactericides, acaricides, nematicides, fungicides, growth-regulating substances, herbicides, safeners, fertilizers or semiochemicals.

Particularly favourable mixing components are, for example, the following compounds:
Fungicides:
Inhibitors of Nucleic Acid Synthesis
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
Inhibitors of Mitosis and Cell Division
  benomyl, carbendazim, diethofencarb, fuberidazole, pencycuron, thiabendazole, thiophanatmethyl, zoxamide
Inhibitors of Respiratory Chain Complex I
  diflumetorim
Inhibitors of Respiratory Chain Complex II
  boscalid, carboxin, fenfuram, flutolanil, furametpyr, mepronil, oxycarboxin, penthiopyrad, thifluzamide
Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
  dinocap, fluazinam
Inhibitors of ATP Production
  fentin acetate, fentin chloride, fentin hydroxide, silthiofam
Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil
Inhibitors of Signal Transduction
  fenpiclonil, fludioxonil, quinoxyfen
Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride
Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
  aldimorph, dodemorph, dodemorph acetate, fenpropimorph, tridemorph, fenpropidin, spiroxarine,
  naftifine, pyributicarb, terbinafine
Inhibitors of Cell Wall Synthesis
  benthiavalicarb, bialaphos, dimethomorph, flumorph, iprovalicarb, polyoxins, polyoxorim, validamycin A
Inhibitors of Melanin Biosynthesis
  capropamid, diclocymet, fenoxanil, phthalid, pyroquilon, tricyclazole Resistance Induction
: acibenzolar-S-methyl, probenazole, tiadinil Multisite
: captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
: amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxy-quinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazolecarboxamide, 2-chloro-N-(2,3-dihydro-1,1,3-trimethyl-1H-inden-4-yl)-3-pyridine-carboxamide, 3-[5-(4-chlorophenyl)-2,3-dimethylisoxazolidin-3-yl]pyridine, cis-1-(4-chloro-phenyl)-2-(1H-1,2,4-triazol-1-yl)cycloheptanol, 2,4-dihydro-5-methoxy-2-methyl-4-[[[[1-[3-(trifluoromethyl)phenyl]ethylidenelamino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)-N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl)[1,2,4]-triazolo[1,5-a]pyrimidine, 5-chloro-6(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)-imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenyl-ethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl) 1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

Acetylcholine Esterase (AChE) Inhibitors
: carbamates,
: for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
: organophosphates,
: for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
: pyrethroids,
: for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cyprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, peimethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
DDT
oxadiazines,
for example indoxacarb
semicarbazones,
for example metaflumizone (BAS 320 1)
Acetylcholine Receptor Agonists/Antagonists
chloronicotinyls,
for example acetamiprid, clothianidin, dinotefuran, imidacloprid, nitenpyram, nithiazine, thiacloprid, thiamethoxam
nicotine, bensultap, cartap
Acetylcholine Receptor Modulators
spinosyns,
for example spinosad
GABA-Controlled Chloride Channel Antagonists
organochlorines,
for example camphechlor, chlordane, endosulphan, gamma-HCH, HCH, heptachlor, lindane, methoxychlor
fiprols,
for example acetoprole, ethiprole, fipronil, pyrafluprole, pyriprole, vaniliprole
Chloride Channel Activators
mectins,
for example avermectin, emamectin, emamectin-benzoate, ivermectin, milbemycin
Juvenile hormone mimetics,
for example diofenolan, epofenonane, fenoxycarb, hydroprene, kinoprene, methoprene, pyriproxifen, triprene
Ecdysone Agonists/Disruptors
diacylhydrazines,
for example chromafenozide, halofenozide, methoxyfenozide, tebufenozide
Chitin Biosynthesis Inhibitors
benzoylureas,
for example bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine
Oxidative Phosphorylation Inhibitors, ATP Disruptors
diafenthiuron
organotin compounds,
for example azocyclotin, cyhexatin, fenbutatin-oxide
Oxidative Phosphorylation Decouplers Acting by Interrupting the H-Proton Gradient
pyrroles,
for example chlorfenapyr
dinitrophenols,
for example binapacyrl, dinobuton, dinocap, DNOC
Site-I Electron Transport Inhibitors
METI's,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
Bacillus thuringiensis strains
Lipid Synthesis Inhibitors
tetronic acids,
for example spirodiclofen, spiromesifen
tetramic acids,
for example spirotetramat
carboxamides,
for example flonicamid
octopaminergic agonists,
for example amitraz
Inhibitors of Magnesium-Stimulated ATPase,
propargite
Ryanodine Receptor Effectors
a) benzoic acid dicarboxamides,
for example flubenediamide
b) anthranilamides, for example
rynaxapyr (3-bromo-N-{4-chloro-2-methyl-6-[(methylamino)carbonyl]phenyl}-1-(3-chloropyridin-2-yl)-1H-pyrazole-5-carboxamide)
nereistoxin analogues,
for example thiocyclam hydrogen oxalate, thiosultap-sodium
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
fumigants,
for example aluminium phosphide, methyl bromide, sulphuryl fluoride
antifeedants,
for example cryolite, flonicamid, pymetrozine
Mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds/active compound combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds/active compound combinations according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are further-more particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds/active compound compositions according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderna* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds/active compound combinations of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds/active compound compositions according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds/active compound compositions according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and timber products and coating compositions.

The materials to be very particularly preferably protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flash point of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range of 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flash point of above 30° C., preferably above 45° C., can be partially replaced by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or relatively high molecular weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypennethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin, and fungicides, such as epoxyconazole, hexaconazole, azaconazole, propiconazole, tebuconazole, cyproconazole, metconazole, imazalil, dichlorfluanid, tolylfluanid, 3-iodo-2-propynyl butylcarbamate, N-octyl-isothiazolin-3-one and 4,5-dichloro-N-octylisothiazolin-3-one.

The compounds according to the invention can at the same time be employed for protecting objects which come into contact with saltwater or brackish water, in particular hulls, screens, nets, buildings, moorings and signaling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;
molluscicides such as fentin acetate, metaldehyde, methiocarb, niclosamid, thiodicarb and trimethacarb, Fe chelates;

or conventional antifouling active compounds such as 4,5-dichloro-2-octyl-4-isothiazolin-3-one, diiodomethylparatryl sulphone, 2-(N,N-dimethyl-thiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in saltwater. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coloptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds/active compound combinations according to the invention can also be used as defoliants, desiccants, haulm killers and, in particular, as weed killers. Weeds in the broadest sense are understood as meaning all plants which grow at locations where they are undesired.

Whether the substances according to the invention act as nonselective or selective herbicides depends essentially on the application rate.

The active compounds/active compound combinations according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds/active compound combinations according to the invention is in no way restricted to these genera, but extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian blue, and organic colorants, such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzolenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfuron, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), pyroxsulam, pyroxasulfone, quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazonemethyl, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

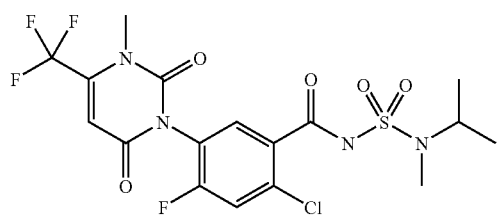

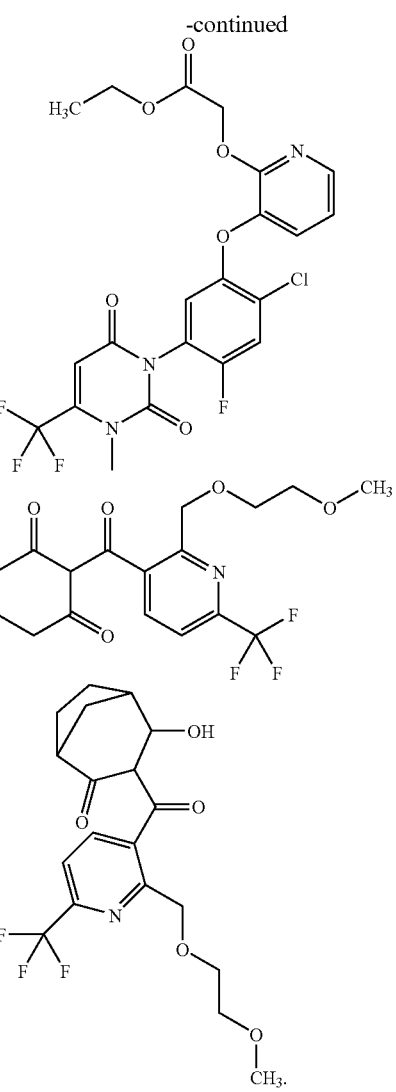

A mixture with other known active compounds, such as fungicides, insecticides, acaricides, nematicides, bird repellents, plant nutrients and soil conditioners, is also possible.

The active compounds/active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds/active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are compatible with plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soybeans, potatoes, cotton, oilseed rape, beet, sugar cane and also fruit plants (with the fruits apples, pears, citrus fruits and grape vines), great emphasis being given to cereals, maize, soybeans, potatoes, cotton and oilseed rape.

The term "active compounds" always also includes the active compound combinations mentioned here.

PREPARATION EXAMPLES

Example I-1-a-1

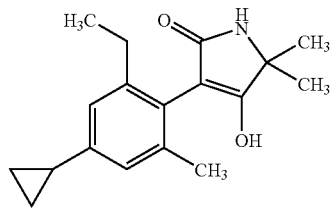

0.88 g of potassium tert-butoxide are initially charged in 10 ml of N,N-dimethylformamide, at 60° C., 1 g of the compound of Example II-1, dissolved in 5 ml of N,N-dimethylformamide, is added dropwise over a period of 30 min and the mixture is stirred at 60° C. for 4 h. The mixture is taken up in 100 ml of water, adjusted to pH 1 using 1N HCl, concentrated, again taken up in water and concentrated. The residue is taken up in 10 ml of water and extracted with dichloromethane, and the extract is dried with sodium sulphate and concentrated. The residue is then stirred in 4 ml of ethyl acetate and filtered off with suction. This gives 0.3 g of a colourless solid (yield 36% of theory) of m.p.: 218° C.

Analogously to Example (I-1-a-1) and in accordance with the general statements on the preparation, the following compounds of the formula (I-1-a) are obtained (I-1-a)

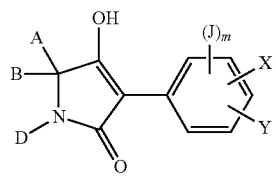

| Ex. No. | m | J | X | Y | D | A | B | m. p. °C. | Isomer |
|---|---|---|---|---|---|---|---|---|---|
| I-1-a-2 | 1 | 4-cyclopropyl | 2-C$_2$H$_5$ | 6-CH$_3$ | H | —(CH$_2$)$_2$—CHOCH$_3$—(CH$_2$)$_2$— | | 222 | β |
| I-1-a-3 | 1 | 4-cyclopropyl | 2-C$_2$H$_5$ | 6-CH$_3$ | H | —CH$_2$—CHOC$_4$H$_9$—(CH$_2$)$_3$— | | 203 | β |
| I-1-a-4 | 1 | 4-cyclopropyl | 2-CH$_3$ | 6-CH$_3$ | H | —(CH$_2$)$_2$—CHOCH$_3$—(CH$_2$)$_2$— | | 264 | β |
| 1-1-a-5 | 1 | 2-cyclopropyl | 6-C$_2$H$_5$ | 4-CH$_3$ | H | CH$_3$ | CH$_3$ | 262 | — |
| I-1-a-6 | 1 | 2-cyclopropyl | 6-C$_2$H$_5$ | 4-CH$_3$ | H | —(CH$_2$)$_2$—CHOCH$_3$—(CH$_2$)$_2$— | | 245 | β |
| I-1-a-7 | 1 | 2-cyclopropyl | 4-CH$_3$ | 6-CH$_3$ | H | —(CH$_2$)$_2$—CHOCH$_3$—(CH$_2$)$_2$— | | 113 | β |

-continued (I-1-a)

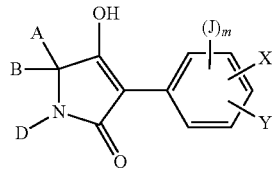

| Ex. No. | m | J | X | Y | D | A | B | m. p. °C. | Isomer |
|---|---|---|---|---|---|---|---|---|---|
| I-1-a-8 | 1 | 2- ◁ | 4-CH₃ | 6-CH₃ | H | CH₃ | CH₃ | 100 | — |
| I-1-a-9 | 1 | 2- ◁ | 4-CH₃ | 6-CH₃ | H | —(CH₂)₂—CHOC₂H₅—(CH₂)₃— | | 109 | β |
| I-1-a-10 | 1 | 2- ◁ | 6-Cl | 4-CH₃ | H | CH₃ | CH₃ | *1.33 ppm (s, 6 H, C(CH₃)₂), 0.75 (m, 2 H, CH₂ (cyclopropyl)), 0.60 and 0.51 ppm (in each case m, 1 H, CH₂(cyclopropyl)) | — |
| I-1-a-11 | 1 | 2- ◁ | 6-Cl | 4-CH₃ | H | —(CH₂)₂—CHOCH₃—(CH₂)₂— | | *3.26 ppm (s, 3 H, O—CH₃), 0.75 (m, 2 H, CH₂ (cyclopropyl)), 0.59 and 0.51 ppm (in each case m, 1 H, CH₂(cyclopropyl)) | β |
| I-1-a-12 | 1 | 2- ◁ | 6-Cl | 4-CH₃ | H | —CH₂—CHOC₄H₉—(CH₂)₃— | | *3.58 ppm (m, 2 H, OCH₂), 0.80 (m, 2 H, CH₂ (cyclopropyl)), 0.67 and 0.53 ppm (in each case m, 1 H, CH₂(cyclopropyl)) | β |
| I-1-a-13 | 1 | 4- ◁ | 2-CH₃ | 6-CH₃ | H | —(CH₂)₂—O—CH₂)₂— | | 263 | — |
| I-1-a-14 | 1 | 2- ◁ | 6-Cl | 4-CH₃ | H | —CH₂—CHOC₂H₅—(CH₂)₃— | | *3.45 ppm (m, 2 H, OCH₂), 0.75 (m, 2 H, CH₂ (cyclopropyl)), 0.59 and 0.51 ppm (in each case m, 1 H, CH₂(cyclopropyl)) | β |
| I-1-a-15 | 2 | 2,6- ◁ | 4-CH₃ | H | H | —(CH₂)₂—CHOCH₃—(CH₂)₂— | | 258-260 | β |
| I-1-a-16 | 1 | 4 ◁ | 2-CH₃ | 6-CH₃ | H | —(CH₂)₂—C(OO)—(CH₂)₂— (dioxolane) | | 283 | β |
| I-1-a-17 | 1 | 2- ◁ | 4-CH₃ | 6-CH₃ | H | —CH₂—CHOC₄H₉—(CH₂)₃— | | *3.55 ppm (m, 2 H, OCH₂), 0.75 (m, 2 H, CH₂ (cyclopropyl)), 0.64 and 0.49 ppm (in each case m, 1 H, CH₂(cyclopropyl)) | β |
| I-1-a-18 | 1 | 2- ◁ | 6-C₂H₅ | 4-CH₃ | H | —(CH₂)₃— | H | 224-226 | — |
| I-1-a-19 | 2 | 2,6- ◁ | 4-CH₃ | H | H | CH₃ | CH₃ | 248-250 | — |
| I-1-a-20 | 1 | 2- ◁ | 6-CH₃ | 4-Cl | H | —(CH₂)₂—CHOCH₃—(CH₂)₂— | | *3.41 ppm (s, 3 H, O—CH₃), 0.88 (m, 2 H, CH₂ (cyclopropyl)), 0.72 and 0.51 ppm (in each case m, 1 H, CH₂(cyclopropyl)) | β |

(I-1-a)

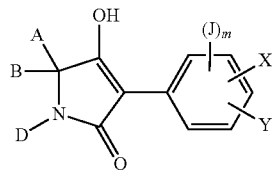

| Ex. No. | m | J | X | Y | D | A | B | m. p. °C. | Isomer |
|---|---|---|---|---|---|---|---|---|---|
| I-1-a-21 | 2 | 2,4-◁ | 6-C$_2$H$_5$ | H | H | CH$_3$ | CH$_3$ | 216-219 | — |
| I-1-a-22 | 2 | 2,4-◁ | 6-C$_2$H$_5$ | H | H | —(CH$_2$)$_2$—CHOCH$_3$—(CH$_2$)$_2$— | | 245-248 | β |
| I-1-a-23 | 2 | 2,6-◁ | 4-CH$_3$ | H | H | △ | CH$_3$ | 222-225 | — |
| I-1-a-24 | 1 | 4-◁ | 2-CH$_3$ | 6-CH$_3$ | H | —CH$_2$—CHOCH$_3$—(CH$_2$)$_2$— | | 202-205 | cis |
| I-1-a-25 | 1 | 4-◁ | 2-CH$_3$ | 6-CH$_3$ | H | —CH$_2$—CHOCH$_3$—(CH$_2$)$_2$— | | 80-90 | trans |
| I-1-a-26 | 1 | 4-◁ | 2-CH$_3$ | 6-CH$_3$ | H | —(CH$_2$)$_2$—CH(CH$_2$OCH$_3$)—(CH$_2$)$_2$— | | 251 | β |

Example I-1-b-1

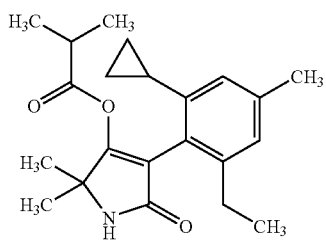

0.14 g of the compound of Example I-1-a-5 is initially charged in 8 ml of ethyl acetate, 0.05 g of triethylamine and 1.5 mg of 4-N,N'-dimethylaminopyridine are added and the mixture is heated to 60° C. A solution of 0.05 g of isobutyl chloride in 2 ml of ethyl acetate is added in 7 portions over a period of 60 min, and the mixture is stirred at 60° C. for 6 h. The mixture is allowed to stand overnight, semiconcentrated sodium chloride solution is then added and the organic phase is separated off and purified by column chromatography on silica gel (gradient EtOAc/n-heptane 1:9 to ethyl acetate/n-heptane 100:0). This gives 90 mg of a colourless solid (yield 60% of theory). m.p.: 151° C.

Analogously to Example (I-1-b-1) and in accordance with the general statements on the preparation, the following compounds of the formula (I-1-b) are obtained (I-1-b)

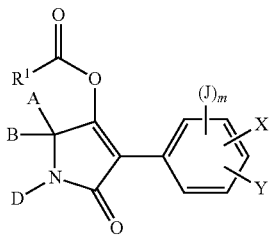

| Ex. No. | m | J | X | Y | D | A | B | R$^1$ | m. p. ° C. | Isomer |
|---|---|---|---|---|---|---|---|---|---|---|
| I-1-b-2 | 1 | 4-◁ | 2-C$_2$H$_5$ | 6-CH$_3$ | H | —CH$_2$—CHOC$_4$H$_9$—(CH$_2$)$_3$— | | i-C$_3$H$_7$ | 173 | β |
| I-1-b-3 | 1 | 4-◁ | 2-C$_2$H$_5$ | 6-CH$_3$ | H | —(CH$_2$)$_2$—CHOCH$_3$—(CH$_2$)$_2$— | | i-C$_3$H$_7$ | *0.99 (dd, 6 H, CH(C<u>H</u>$_3$)$_2$) 2.18 (s, 3 H, Ar—C<u>H</u>$_3$) 3.21 (m, 1 H, C<u>H</u>OCH$_3$) | β |

-continued

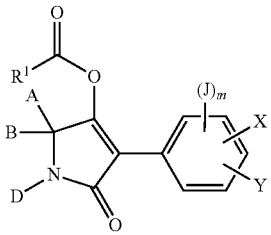

(I-1-b)

| Ex. No. | m | J | X | Y | D | A | B | R¹ | m. p. °C | Isomer |
|---|---|---|---|---|---|---|---|---|---|---|
| I-1-b-4 | 1 | 4-▷ | 2-CH₃ | 6-CH₃ | H | —(CH₂)₂—CHOCH₃—(CH₂)₂— | | i-C₃H₇ | 194-196 | β |
| I-1-b-5 | 1 | 4-▷ | 2-CH₃ | 6-CH₃ | H | —CH₂—CHOC₂H₅—(CH₂)₃— | | i-C₃H₇ | 199-202 | β |
| I-1-b-6 | 1 | 2-▷ | 6-C₂H₅ | 4-CH₃ | H | —(CH₂)₂—CHOCH₃—(CH₂)₂— | | i-C₃H₇ | 190 | β |
| I-1-b-7 | 2 | 2,6-▷ | 4-CH₃ | H | H | △ (cyclopropyl) | CH₃ | i-C₃H₇ | 162-163 | — |
| I-1-b-8 | 1 | 2-▷ | 4-CH₃ | 6-CH₃ | H | CH₃ | CH₃ | 2-Cl-C₆H₄ | 154-155 | — |
| I-1-b-9 | 2 | 2,6-▷ | 4-CH₃ | H | H | CH₃ | CH₃ | i-C₃H₇ | 171 | — |
| 1-1-b-10 | 1 | 2-▷ | 4-CH₃ | 6-CH₃ | H | —CH₂—CHOC₄H₉—(CH₂)₃— | | CH₃ | *3.47 ppm (m, 2 H, OCH₂), 2.04 ppm (s, 3 H, COCH₃), 0.85-0.50 ppm (broad multiplet, 4 H, CH₂ (cyclopropyl)) | β |
| 1-1-b-11 | 2 | 2,6-▷ | 4-CH₃ | H | H | —(CH₂)₂—CHOCH₃—(CH₂)₂— | | i-C₃H₇ | 220-222 | β |
| I-1-b-12 | 1 | 2-▷ | 6-Cl | 4-CH₃ | H | —(CH₂)₂—CHOCH₃—(CH₂)₂— | | i-C₃H₇ | 186-187 | β |
| I-1-b-13 | 2 | 2,4-▷ | 6-CH₃ | H | H | CH₃ | CH₃ | i-C₃H₇ | 176-177 | — |
| I-1-b-14 | 2 | 2,4-▷ | 6-C₂H₅ | H | H | —(CH₂)₂—CHOCH₃—(CH₂)₂— | | i-C₃H₇ | 190-192 | β |
| I-1-b-15 | 1 | 2-▷ | 6-C₂H₅ | 4-CH₃ | —(CH₂)₃— | | H | i-C₃H₇ | *4.75 ppm (m, 1 H, CH—N (bridge head)), 1.10 ppm (m, 9 H, Ar—CH2)—CH₃, and CH(CH₃)₂), 0.95-0.54 ppm (broad heap of signals, 4 H, CH₂ (cyclopropyl)) | — |

¹H-NMR (400 MHz, CDCl₃): shifts δ in ppm

Example I-1-c-1

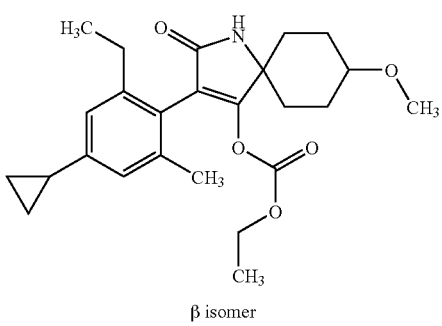

β isomer 0.15 g of the compound of Example I-1-a-2 and 0.05 g of triethylamine are initially charged in 8 ml of dichloromethane, the mixture is stirred at RT for 5 min, 0.05 g of ethyl chloroformate is added and the mixture is stirred at RT overnight. 5 ml of 10% strength $Na_2CO_3$ solution are added, the mixture is stirred at RT for 10 min, separated using extraction cartridges and concentrated using a rotary evaporator, and the residue is purified by column chromatography on silica gel using 1/1 ethyl acetate/n-heptane. This gives 68 g of an oil (yield 38% of theory).

$^1$H-NMR (400 MHz, $CDCl_3$): δ=2.18 (s, 3H; Ar—$CH_3$), 3.23 (m, 1H, $CHOCH_3$), 4.01 (q, 2H, $OCH_2CH_3$) ppm.

Analogously to Example (I-1-c-1) and in accordance with the general statements on the preparation, the following compounds of the formula (I-1-c) are obtained

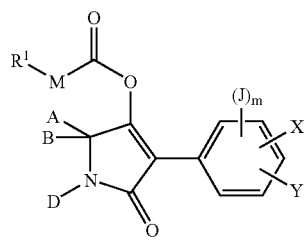

(I-1-c)

| Ex. No. | m | J | X | Y | D | A | B | M | R² | m. p. ° C. | Isomer |
|---|---|---|---|---|---|---|---|---|---|---|---|
| I-1-c-2 | 1 | 4- cyclopropyl | 2-C₂H₅ | 6-CH₃ | H | —CH₂—CHOC₄H₉—(CH₂)₂— | | O | C₂H₅ | *2.46 (m, 2 H, Ar—CH₂) 3.38 (m, 1 H, CHO—CH₂) 4.01 (q, 2 H, O—CH₂—CH₃) | β |
| I-1-c-3 | 1 | 4- cyclopropyl | 2-CH₃ | 6-CH₃ | H | —(CH₂)₂—CHOCH₃—(CH₂)₂— | | O | C₂H₅ | 200-202 | β |
| I-1-c-4 | 1 | 4- cyclopropyl | 2-CH₃ | 6-CH₃ | H | —CH₂—CHOC₂H₅—(CH₂)₃— | | O | C₂H₅ | 190-192 | β |
| I-1-c-5 | 1 | 4- cyclopropyl | 2-CH₃ | 6-CH₃ | H | —CH₂—CHOCH₃—(CH₂)₂— | | O | C₂H₅ | 114-116 | cis |
| I-1-c-6 | 1 | 4- cyclopropyl | 2-CH₃ | 6-CH₃ | H | —CH₂—CHOCH₃—(CH₂)₂— | | O | C₂H₅ | 177 | trans |
| I-1-c-7 | 1 | 2- cyclopropyl | 4-CH₃ | 6-CH₃ | H | —(CH₂)₂—CHOCH₃—(CH₂)₃— | | O | C₂H₅ | *4.01 ppm (q, 2 H, O—CH₂), 3.38 ppm (s, 3 H, OCH₃), 0.83 0.75, 0.66, 0.56 ppm (in each case m, 1 H, CH₂(cyclopropyl)) | β |
| I-1-c-8 | 1 | 2- cyclopropyl | 4-CH₃ | 6-CH₃ | H | —CH₂—CHOC₂H₅—(CH₂)₃— | | O | C₂H₅ | *4.01 ppm (q, 2 H, O—CH₂), 3.53 ppm (s, 2 H, OCH₂), 0.86-0.5 ppm (Heap of signals, together 4 H, CH₂(cyclopropyl)) | β |
| I-1-c-9 | 1 | 2- cyclopropyl | 6-Cl | 4-CH₃ | H | —(CH₂)₂—CHOCH₃—(CH₂)₂— | | O | C₂H₅ | 199-202 | β |
| I-1-c-10 | 1 | 2- cyclopropyl | 4-CH₃ | 6-CH₃ | H | CH₃ | CH₃ | O | C₂H₅ | *4.03 ppm (q, 2 H, O—CH₂), 1.51 ppm (s, 6 H, C(CH₃)₂), 0.81 0.74, 0.64, 0.55 ppm (in each case m, 1 H, CH₂(cyclopropyl)) | — |
| 1-1-c-11 | 1 | 4- cyclopropyl | 2-CH₃ | 6-CH₃ | H | —(CH₂)₂—O—(CH₂)₂— | | O | C₂H₅ | 210 | — |
| I-1-c-12 | 1 | 2- cyclopropyl | 6-Cl | 4-CH₃ | H | —CH₂—CHOC₂H₅—(CH₂)₃— | | O | C₂H₅ | 188-189 | β |

-continued (I-1-c)

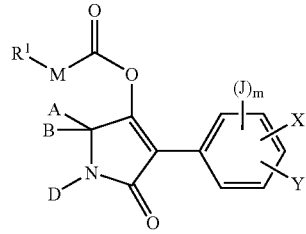

| Ex. No. | m | J | X | Y | D | A | B | M | R² | m. p. ° C. | Isomer |
|---|---|---|---|---|---|---|---|---|---|---|---|
| I-1-c-13 | 2 | 2,6—◁ | 4-CH₃ | H | H | CH₃ | CH₃ | O | C₂H₅ | *4.05 ppm (q, 2 H, OCH₂), 1.51 ppm (s, 6 H, C(CH₃)₂), 0.79 ppm (m, 4 H, CH₂ (cyclopropyl)), 0.70 and 0.59 ppm (in each case m, 2 H, CH₂(cyclopropyl)) | — |
| I-1-c-14 | 1 | 2—◁ | 4-CH₃ | 6-CH₃ | H | —CH₂—CHOC₂H₅—(CH₂)₃— | | O | C₂H₅ | 236-237 | β |
| I-1-c-15 | 1 | 2—◁ | 6-Cl | 4-CH₃ | H | —CH₂—CHOC₂H₅—(CH₂)₃— | | O | CH₃ | 230-231 | β |
| I-1-c-16 | 1 | 2—◁ | 4-CH₃ | 6-CH₃ | H | —CH₂—CHOC₄H₉—(CH₂)₃— | | O | C₂H₅ | 173 | β |
| I-1-c-17 | 1 | 2—◁ | 4-CH₃ | 6-CH₃ | H | —CH₂—CHOC₄H₉—(CH₂)₃— | | O | CH₃ | 180-183 | β |
| I-1-c-18 | 2 | 2,6—◁ | 4-CH₃ | H | H | △— | CH₃ | O | C₂H₅ | 155-156 | — |
| I-1-c-19 | 2 | 2,6—◁ | 4-CH₃ | H | H | —(CH₂)₂—CHOCH₃—(CH₂)₂— | | O | C₂H₅ | 205-208 | β |
| I-1-c-20 | 1 | 2—◁ | 4-Cl | 6-CH₃ | H | —(CH₂)₂—CHOCH₃—(CH₂)₂— | | O | C₂H₅ | 176-177 | β |
| I-1-c-21 | 2 | 2,4—◁ | 6-C₂H₅ | H | H | CH₃ | CH₃ | O | C₂H₅ | 167-168 | — |
| I-1-c-22 | 2 | 2,4—◁ | 6-C₂H₅ | H | H | —(CH₂)₂—CHOCH₃—(CH₂)₂— | | O | C₂H₅ | *4.05 ppm (q, 2 H, O—CH₂), 3.40 ppm (s, 3 H, O-CH₃), 0.81 (m, 4 H, CH₂ (cyclopropyl)), 0.67, 0.60 ppm (in each case m, 2 H, CH₂(cyclopropyl)) | β |
| I-1-c-23 | 2 | 2,4—◁ | 6-C₂H₅ | H | H | —(CH₂)₂—CHOCH₃—(CH₂)₂— | | O | CH₃ | *3.63 ppm (s, 2 H, COO—CH₃), 3.40 ppm (s, 3 H, O—CH₃), 0.92 (m, 2 H, CH₂ (cyclopropyl)), 0.82-0.55 ppm (broad heap of signals, 6 H, CH₂(cyclopropyl)) | β |
| I-1-c-24 | 1 | 2—◁ | 6-C₂H₅ | 4-CH₃ | H | —(CH₂)₃ | H | O | C₂H₅ | *4.75 ppm (m, 1 H, CH—N (bridge head)), 4.19 ppm (dq, 2 H, O—CH₂), 0.95-0.54 ppm (broad heap of signals, 4 H, CH₂(cyclopropyl)) | — |
| I-1-c-25 | 1 | 2—◁ | 6-C₂H₅ | 4-CH₃ | H | CH₃ | CH₃ | O | CH₃ | *3.63 ppm (s, 2 H, O—CH₃), 1.51 ppm (s, 6 H, (CH₃)₂), 0.78 (m, 2 H, CH₂(cyclopropyl)), 0.67, 0.59 ppm (in each case m, 1 H, CH₂(cyclopropyl)) | — |

*¹H-NMR (400 MHz, CDCl₃): shifts δ in ppm

Example I-1-d-1

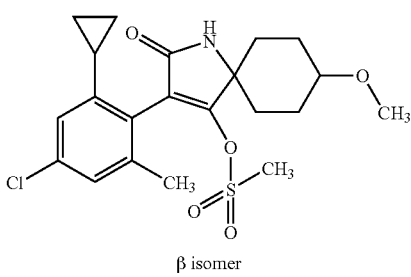

β isomer 0.15 g (0.415 mmol) of the compound of Example I-1-a-20, 0.07 ml of triethylamine and 1.5 mg of DMAP are initially charged in 10 ml of chloroform, the mixture is stirred at room temperature for 10 min and 0.04 ml of methanesulphonyl chloride is added. The mixture is stirred at room temperature for about 18 h. After the reaction has ended, the mixture is poured into 5 ml of 5% strength sodium bicarbonate solution and stirred at room temperature for 10 min. The organic phase is separated off and dried over $Na_2SO_4$, and the solvent is removed under reduced pressure using a rotary evaporator. The residue is purified by column chromatography (ethyl acetate/n-heptane 1:1).

Yield: 0.082 g (45% of theory)

$^1$H-NMR (400 MHz, $CDCl_3$): δ=0.67, 0.89 ppm (2 m, in each case 2H, $CH_2$-cyclopropyl), 2.57 ppm (s, 3H, $SO_2$—$CH_3$), 3.40 ppm (s, 3H, O—$CH_3$).

Analogously to Example (I-1-d-1), Example (I-1-d-2) is obtained:

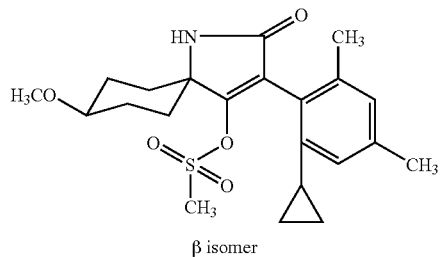

β isomer $^1$H-NMR (400 MHz, $CDCl_3$): δ=3.40 ppm (s, 3H, O—$CH_3$), 2.47 ppm (s, 3H, $SO_2$—$CH_3$), 0.87, 0.81, 0.67, 0.62 ppm (in each case m, 1H, $CH_2$ (cyclopropyl)).

Example II-1

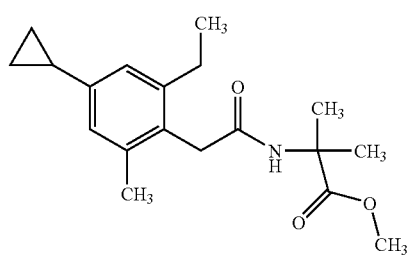

1 g of the compound of Example (XXX-2) is dissolved in 30 ml of dichloromethane, 2 drops of N,N-dimethylformamide and 0.76 g of oxalyl chloride are added and the mixture is heated at the boil under reflux for 2 h until the evolution of gas has ceased, concentrated, twice taken up in each case 20 ml of dichloromethane, reconcentrated and taken up in 20 ml of dichloromethane (solution 1).

0.7 g of methyl 1-aminoisobutylate hydrochloride is initially charged in 30 ml of dichloromethane, 0.97 g of triethylamine is added, the mixture is stirred at room temperature for 15 min, solution 1 is then added dropwise over a period of 30 min, the mixture is stirred at room temperature overnight, 30 ml of water are added, the mixture is stirred for 20 min and the org. phase is separated off, dried and purified chromatographical on silica gel (gradient ethyl acetate/heptane 5:95 to 100:0. This gives 1.05 g of a colourless solid (yield 72% of theory). m.p.: 127° C.

Analogously to Example (II-1) and in accordance with the general statements on the preparation, the following compounds of the formula (II) are obtained:

(II)

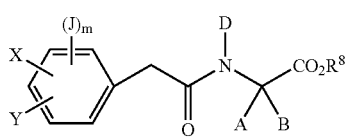

| Ex. No. | m | J | X | Y | D | A | B | $R^8$ | m. p. ° C. | Isomer |
|---|---|---|---|---|---|---|---|---|---|---|
| II-2 | 1 | 4-cyclopropyl | 2-$C_2H_5$ | 6-$CH_3$ | H | —($CH_2)_2$—CHOCH$_3$—($CH_2)_2$— | | $CH_3$ | 123 | β |
| II-3 | 1 | 4-cyclopropyl | 2-$C_2H_5$ | 6-$CH_3$ | H | —$CH_2$—CHO$C_4H_9$—($CH_2)_3$— | | $CH_3$ | *2.89 (m, 1 H, C$\underline{H}$O $CH_2$) 3.58 (s, 2 H, Ar—C$\underline{H}_2$—CO) | β |
| II-4 | 1 | 4-cyclopropyl | 2-$CH_3$ | 6-$CH_3$ | H | —($CH_2)_2$—CHOCH$_3$—($CH_2)_2$— | | $CH_3$ | *3.12 (m, 1 H, C$\underline{H}$O $CH_3$) 6.80 (s, 2 H, Ar—$\underline{H}$) | β |

-continued

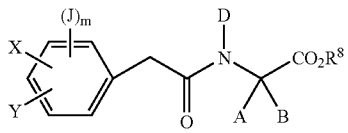

(II)

| Ex. No. | m | J | X | Y | D | A | B | R⁸ | m.p. °C. | Isomer |
|---|---|---|---|---|---|---|---|---|---|---|
| II-5 | 1 | 2- cyclopropyl | 6-C₂H₅ | 4-CH₃ | H | CH₃ | CH₃ | CH₃ | 114 | — |
| II-6 | 1 | 2- cyclopropyl | 6-C₂H₅ | 4-CH₃ | H | —(CH₂)₂—CHOCH₃—(CH₂)₂— | | CH₃ | 96-98 | β |
| II-7 | 1 | 2- cyclopropyl | 4-CH₃ | 6-CH₃ | H | —(CH₂)₂—CHOCH₃—(CH₂)₂— | | CH₃ | *3.12 (m, 1 H, C$\underline{H}$O CH₃) 3.80 (m, 2 H, Ar—C$\underline{H}$₂—CO) | β |
| II-8 | 1 | 2- cyclopropyl | 4-CH₃ | 6-CH₃ | H | CH₃ | CH₃ | CH₃ | *1.43 (s, 6 H, C(C$\underline{H}$₃)₂) 3.68 (s, 2 H, Ar—C$\underline{H}$₂—CO) | — |
| II-9 | 1 | 2- cyclopropyl | 4-CH₃ | 6-CH₃ | H | —CH₂—CHOC₂H₅—(CH₂)₃— | | CH₃ | *2.99 (m, 1 H, C$\underline{H}$OCH₂—) | β |
| II-10 | 1 | 4- cyclopropyl | 2-CH₃ | 6-CH₃ | | —CH₂—CHOC₂H₅—(CH₂)₃— | | CH₃ | 131 | β |
| II-11 | 1 | 4- cyclopropyl | 2-CH₃ | 6-CH₃ | H | —(CH₂)₂—O—(CH₂)₂— | | CH₃ | 189 | — |
| II-12 | 1 | 4- cyclopropyl | 2-CH₃ | 6-CH₃ | H | —(CH₂)₂—CH(CH₂OCH₃)—(CH₂)₂— | | CH₃ | 156 | β |
| II-13 | 2 | 2,6- cyclopropyl | 4-CH₃ | H | H | —(CH₂)₂—CHOCH₃—(CH₂)₂— | | CH₃ | 120 | β |
| II-14 | 2 | 2,6- cyclopropyl | 4-CH₃ | H | H | CH₃ | CH₃ | CH₃ | 118-119 | — |
| II-15 | 1 | 2- cyclopropyl | 4-CH₃ | 6-CH₃ | H | —CH₂—CHOC₄H₉—(CH₂)₃— | | CH₃ | directly reacted further | β |
| II-16 | 1 | 2- cyclopropyl | 6-C₂H₅ | 4-CH₃ | | —(CH₂)₃— | H | CH₃ | *4.52 ppm (m, 1 H, CH—N), 0.85 (m, 2 H, CH₂(cyclopropyl)), 0.62 ppm (m, 2 H, CH₂(cyclopropyl)) | — |
| II-17 | 1 | 4 cyclopropyl | 2-CH₃ | 6-CH₃ | H | —(CH₂)₂—C(OCH₂CH₂O)—(CH₂)₂— | | CH₃ | 174 | — |
| II-18 | 1 | 2- cyclopropyl | 4-Cl | 6-CH₃ | H | —(CH₂)₂—CHOCH₃—(CH₂)₂— | | CH₃ | 129-131 | β |
| II-19 | 1 | 2- cyclopropyl | 6-Cl | 4-CH₃ | H | CH₃ | CH₃ | CH₃ | 122-123 | — |
| II-20 | 1 | 2- cyclopropyl | 6-Cl | 4-CH₃ | H | —(CH₂)₂—CHOCH₃—(CH₂)₂— | | CH₃ | 129-131 | β |
| II-21 | 1 | 2- cyclopropyl | 6-Cl | 4-CH₃ | H | —CH₂—CHOC₄H₉—(CH₂)₃— | | CH₃ | 100-101 | β |
| II-22 | 1 | 2- cyclopropyl | 6-Cl | 4-CH₃ | H | —CH₂—CHOC₂H₅—(CH₂)₃— | | CH₃ | *3.68 ppm (s, 3 H, OCH₃), 3.41 ppm (m, 2 H, OCH₂), 0.99 and 0.66 (in each case m, 2 H, CH₂(cyclopropyl)) | β |

-continued

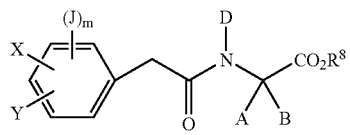
(II)

| Ex. No. | m | J | X | Y | D | A | B | R⁸ | m. p. °C. | Isomer |
|---|---|---|---|---|---|---|---|---|---|---|
| II-23 | 2 | 2,4-cyclopropyl | 6-C$_2$H$_5$ | H | H | CH$_3$ | CH$_3$ | CH$_3$ | 124-125 | — |
| II-24 | 2 | 2,4-cyclopropyl | 6-C$_2$H$_5$ | H | H | —(CH$_2$)$_2$—CHOCH$_3$—(CH$_2$)$_2$— | | CH$_3$ | — | β |
| II-25 | 2 | 2,6-cyclopropyl | 4-CH$_3$ | H | H | cyclopropyl | CH$_3$ | CH$_3$ | *3.70 ppm (s, 3 H, COO-CH$_3$), 1.37 ppm (s, 3 H, CH$_3$), 1.89 ppm (m, 2 H, Ar—CH (cyclopropyl)) | — |
| II-26 | 2 | 2,4-cyclopropyl | 6-CH$_3$ | H | H | CH$_3$ | CH$_3$ | CH$_3$ | *1.42 ppm (s, 6 H, (CH$_3$)$_2$C—NH), 3.80 ppm (s, 2 H, Ar—CH$_2$—CO) | — |
| II-27 | 1 | 4-cyclopropyl | 4-CH$_3$ | 6-CH$_3$ | | —(CH$_2$)$_3$— | H | CH$_3$ | *4.18 ppm (m, 2 H, O—CH$_2$), 3.95 and 3.81 ppm (in each case m, together 1 H, CH—O), 0.94 and 0.67 (in each case m, 2 H, CH$_2$(cyclopropyl)) | — |

*$^1$H-NMR (400 MHz, CDCl$_3$): shifts δ in ppm

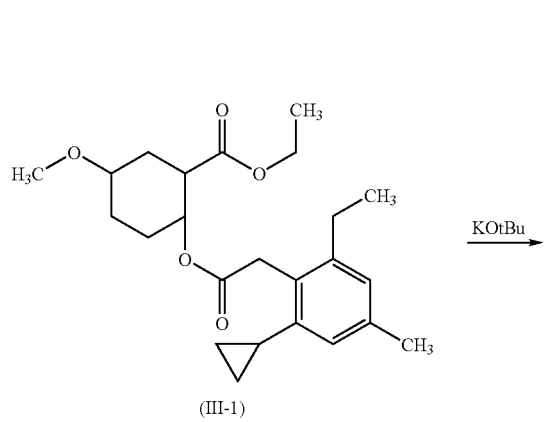
(III-1)

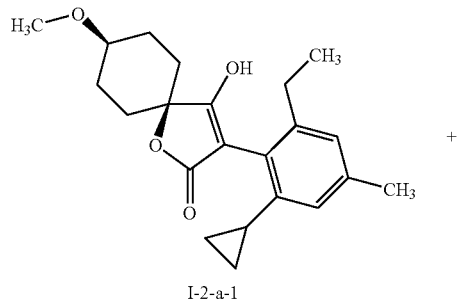
I-2-a-1

+

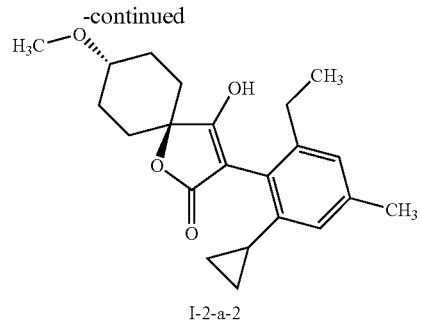
I-2-a-2

0.59 g (1.466 mmol) of the compound of Example (III-1) is initially charged in 10 ml of DMF, 0.247 g (2.199 mmol) of potassium tert-butoxide is added and the mixture is stirred at room temperature for 12 h. DMF is removed using a rotary evaporator, the residue is partitioned between water and methyl tert-butyl ether, the aqueous phase is acidified with hydrochloric acid, the product is extracted with dichloromethane and the org. phase is dried and concentrated using a rotary evaporator.

For further purification and separation of the isomers, the 0.37 g of crude product is chromatographed on silica gel RP18 (acetonitrile/water).

Yield:

89 mg I-2-a-1 (17% of theory), logP=2.81

132 mg I-2-a-2 (25% of theory), logP=3.07

Analogously to Examples (I-2-a-1) and (I-2-a-2) and in accordance with the general statements on the preparation, the following compounds of the formula (I-2-a) are obtained:

| Ex. No. | m | J | X | Y | A | B | logP | Isomer |
|---|---|---|---|---|---|---|---|---|
| I-2-a-3 | 1 | 4-cyclopropyl | 2-CH₃ | 6-CH₃ | —(CH₂)₂—CHOCH₃—(CH₂)₂— | | 2.64 | cis |
| I-2-a-4 | 1 | 4-cyclopropyl | 2-CH₃ | 6-CH₃ | —(CH₂)₂—CHOCH₃—(CH₂)₂— | | 2.88 | trans |
| I-2-a-5 | 1 | 4-cyclopropyl | 2-CH₃ | 6-CH₃ | —(CH₂)₂—O—(CH₂)₂— | | 2.36 | — |

Example I-2-b-1

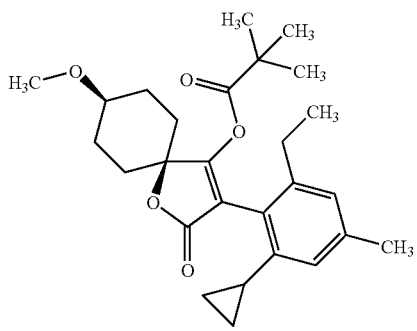

50 mg (0.14 mmol) of the compound of Example I-2-a-1 are initially charged in 5 ml of dichloromethane, 17 mg (0.168 mmol) of triethylamine and 20 mg (0.168 mmol) of pivaloyl chloride are added and the mixture is stirred at room temperature for 12 h. The mixture is concentrated and the crude product is purified by chromatography on silica gel RP18 (acetonitrile/water).

Yield: 60 mg (97% of theory), logP=5.03

Example (III-1)

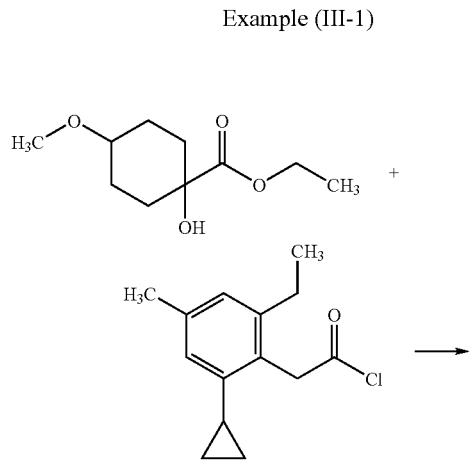

-continued

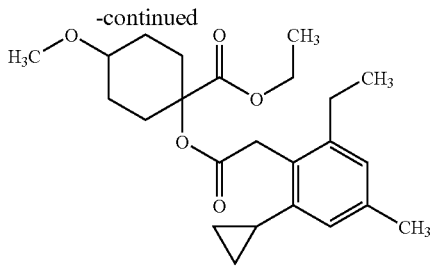

At a bath temperature of 120° C., 0.854 g (4.224 mmol) of ethyl 4-methoxy-1-hydroxy-cyclohexanecarboxylate and 1 g (4.224 mmol) of 2-cyclopropyl-6-ethyl-4-methyl-phenylacetyl chloride are stirred for 6 h and, after cooling, degassed on a rotary evaporator, the residue is dissolved in methyl tert-butyl ether and washed with 5% strength aqueous sodium hydroxide solution and the org. phase is dried and concentrated using a rotary evaporator.

Yield: 0.59 g (35% of theory), oil, logP=5.15

Example I-6-a-1

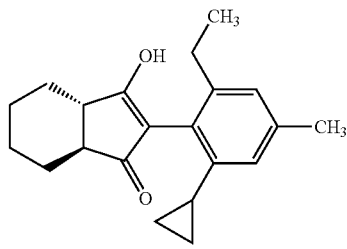

0.58 g (1.7 mmol) of the compound of Example VIII-1 and 0.38 g of potassium tert-butoxide (3.4 mmol) are initially charged in 10 ml of anhydrous DMF and heated at 50° C. for 3 h. After cooling, the mixture is added to ice-water, acidified to pH 2 using 2N hydrochloric acid and extracted with ethyl acetate. The organic phase is twice washed with water, dried (sodium sulphate) and concentrated using a rotary evaporator. Chromatography on silica gel using hexane/ethyl acetate (v/v=70:30) gives 286 mg (54%) of the compound of Example I-6-a-1 in the form of colourless crystals. m.p. 189-190° C.

$^{1}$H-NMR (d$_{6}$-DMSO, 400 MHz): δ=0.45 and 0.67 (in each case mc, in each case 1H), 1.38 and 1.62 (in each case mc, in each case 2H), 1.80 (mc, 1H), 2.22 (s, 3H)

Example VIII-1

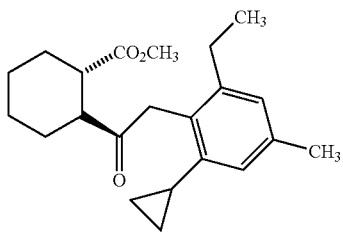

1.50 g (4.6 mmol) of the compound of Example XXXVII-1 in 30 ml of acetone, 1.30 g of potassium carbonate and 1.96 g (13.8 mmol) of iodomethane are together boiled at reflux for 4 h and then taken up in ethyl acetate, shaken with water and dried (magnesium sulphate), and the solvent is distilled off. Chromatography on silica gel using ethyl acetate/hexane (v/v=70:30) gives 1.23 g (78%) of the compound of the formula (VIII-1) as a colourless solid of m.p. 84-85° C.

Example XXXVII-1

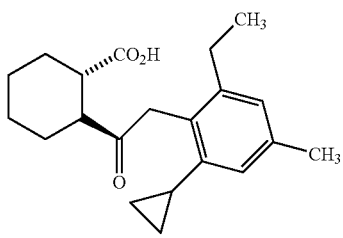

At −30° C., 3.38 g (13.9 mmol) of methyl 2-cyclopropyl-6-ethyl-4-methylphenyl acetate are slowly added dropwise to a solution of lithium diethylamide, prepared from 3.5 g of diethylamine in 25 ml of THF, and 14 ml of a 2.5 molar solution of n-butyllithium in hexane, and the mixture is stirred at room temperature for another 30 min. 2.15 g (13.9 mmol) of cyclohexane-1,2-dicarboxylic anhydride, dissolved in 10 ml of THF, are then added at −20° C., and the mixture is stirred at room temperature for 12 h. Addition of 30 ml of sat. ammonium chloride solution, covering with a layer of ethyl acetate, washing with water, drying (magnesium sulphate) and concentration using a rotary evaporator gives about 5.4 g of a solid to which, without further purification, 2.2 g of potassium hydroxide in 50 ml of water are added, and which is heated under reflux for 24 h. The mixture is then acidified to pH 2 using 2N hydrochloric acid, and the resulting precipitated solid is filtered off with suction.

This gives 1.68 g (37%) of the compound of the formula (XXXVII-1) in the form of yellowish crystals of m.p. 187-188° C.

Example I-8-a-1

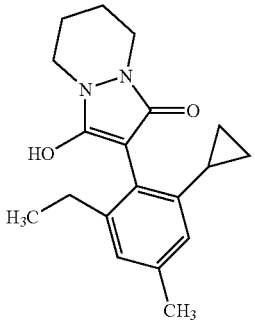

0.992 g (9 mmol) of potassium tert-butoxide are initially charged in 35 ml of anhydrous N,N-dimethylformamide. 1.1 g of the compound of Example XII-1 in N,N-dimethylformamide are then added dropwise, and the mixture is stirred at 80° C. for 2 h. Ice-water is added and the mixture is acidified to pH 1 using concentrated hydrochloric acid and extracted with methylene chloride, and the extract is dried and concentrated under reduced pressure using a rotary evaporator.
Yield: 0.75 g (≙86% of theory)
$^{1}$H-NMR data in CDCl$_{3}$, 400 MHz:
δ=3.75-3.60 (m, 4H); 2.30-2.20 (m, 2H); 1.85-1.75 (m, 4H); 1.55 (m, 1 $^{cy}$Pr—H); 0.90 (m, 1 $^{cy}$Pr—H); 0.85 (m, 1 $^{cy}$Pr—H); 0.75 (m, 1$^{cy}$Pr—H); 0.65 (m, 1 $^{cy}$Pr—H) ppm.

Example I-8-b-1

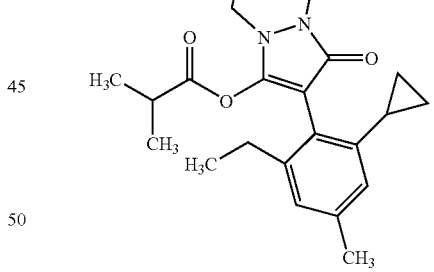

0.15 g (0.5 mmol) of the compound of Example I-8-a-1 and 0.113 g (1 mmol) of potassium carbonate are initially charged in tetrahydrofuran, and isobutyl chloride (0.04 ml) is added at room temperature. After a reaction time of 3 h, the solvent is evaporated under reduced pressure, water is added to the residue, the mixture is extracted with ethyl acetate and the extract is again concentrated under reduced pressure.
Yield: 0.12 g (≙70% of theory)
$^{1}$H-NMR data in CDCl$_{3}$, 400 MHz:
δ=6.85 (s, 1H); 6.55 (s, 1H); 3.90 (m, 1H); 3.80 (m, 1H); 3.35 (m, 2H); 2.65-2.55 (m, 2H); 2.50 (sept, 1H); 2.25 (s, 3H); 1.95 (m, 2H); 1.85 (m, 2H); 1.80 (m, 1 $^{cy}$Pr—H); 1.15 (tr, 3H); 1.05 (m, 6H); 0.75 (m, 2 $^{cy}$Pr—H); 0.60 (m, 1 $^{cy}$Pr—H); 0.55 (m, 1 $^{cy}$Pr—H) ppm.

Analogously to Example (I-8-b-1), Example (I-8-b-2) is obtained

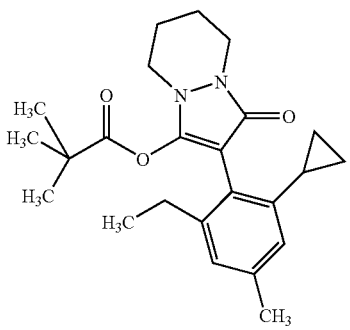

¹H-NMR-data in CDCl₃, 400 MHz:
δ=6.85 (s, 1H); 6.50 (s, 1H); 3.90 (m, 1H); 3.80 (m, 1H); 3.35 (m, 2H); 2.60-2.40 (m, 2H); 2.25 (s, 3H); 1.95 (m, 2H); 1.85 (m, 2H); 1.80 (m, 1 $^{cy}$Pr—H); 1.15 (tr, 3H); 1.05 (s, 9H); 0.80 (m, 2 $^{cy}$Pr—H); 0.60 (m, 1 $^{cy}$Pr—H); 0.55 (m, 1 $^{cy}$Pr—H) ppm.

Analogously to Example I-8-b-1, Example I-8-c-1 is obtained

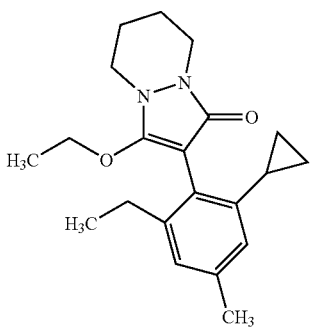

¹H-NMR data in CDCl₃, 400 MHz:
δ=6.90 (s, 1H); 6.60 (s, 1H); 4.15 (q, 2H); 3.90-3.80 (m, 2H), 3.40 (tr, 2H); 2.65-2.45 (m, 2H); 2.25 (s, 3H); 1.95 (m, 2H); 1.85 (m, 2H); 1.80 (m, 1 $^{cy}$Pr—H); 1.20 (tr, 3H); 1.15 (tr, 3H); 0.75 (m, 2 $^{cy}$Pr—H); 0.65 (m, 1 $^{cy}$Pr—H); 0.55 (m, 1 $^{cy}$Pr—H) ppm.

Example XII-1

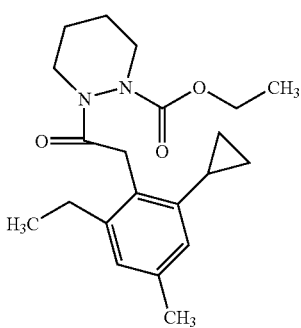

In anhydrous tetrahydrofuran, 2.28 ml (16 mmol) of triethylamine are added to 1.7 g (8 mmol) of the compound from Example XXX-3, 2.46 g (11 mmol) of ethyl hexahydropyridazinecarbazate are added, after 10 min a further 2.28 ml (16 mmol) of triethylamine are added dropwise, immediately afterwards followed by the dropwise addition of 0.73 ml (8 mmol) of phosphorus oxychloride. The solution is heated under reflux for 30 min, the solvent is removed, the residue is taken up in methyl acetate and the mixture is washed twice with water, dried and concentrated. The residue is taken up in n-heptane and filtered through a little silica gel. The filtrate is concentrated.

Yield: 2.3 g (≙74% of theory)
¹H-NMR data in CDCl₃, 400 MHz:
δ=6.85 (s, 1H); 6.75 (s, 1H); 4.55 (dbr, 1H); 4.30-4.20 (mbr, 3H); 4.00 (d, 1H); 3.80 (d, 1H), 2.95 (mbr, 1H); 2.75 (trbr, 1H); 2.55 (q, 2H); 2.25 (s, 3H); 1.80 (m, 1 $^{cy}$Pr—H); 1.75-1.60 (mbr, 4H); 1.15 m (tr, 3H); 0.90-0.75 (m, 2 $^{cy}$Pr—H); 0.70-0.55 (m, 2 $^{cy}$Pr—H) ppm.

Example XXX-1

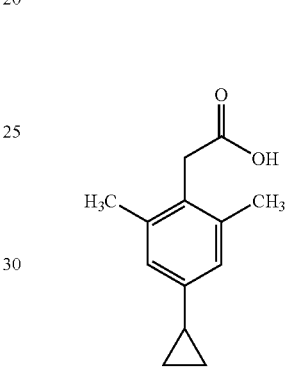

4.8 g of the compound of Example (XXXIV-2) are initially charged in 200 ml of tetrahydrofuran, 0.5 of lithium hydroxide, dissolved in 80 ml of water, is added and the mixture is stirred at room temperature for about 70 h. The tetrahydrofuran is removed using a rotary evaporator, using 1N HCl, the aqueous phase is adjusted to pH1, the aqueous phase is then stirred at room temperature for 10 min and the precipitate is filtered off with suction through a frit. The residue is dissolved in ethyl acetate, the mixture is dried over sodium sulphate and concentrated using a rotary evaporator, the residue is taken up in 30 ml of n-heptane, the mixture is treated with ultrasound for 10 min and filtered off with suction through a frit, and the product is dried. This gives 4.0 g of a colourless solid (yield 89% of theory). m.p.: 138° C.

Analogously to Example (XXX-1) and in accordance with the general statements on the preparation, the following compounds of the formula (XXX) are obtained:

(XXX)

| Ex. No. | m | J | X | Y | m. p. °C. |
|---------|---|---|---|---|-----------|
| XXX-2 | 1 | 4-cyclopropyl | 2-C₂H₅ | 6-CH₃ | 100 |

-continued (XXX)

| Ex. No. | m | J | X | Y | m. p. ° C. |
|---|---|---|---|---|---|
| XXX-3 | 1 | 2- ◁ | 6-C$_2$H$_5$ | 4-CH$_3$ | 139 |
| XXX-4 | 1 | 2- ◁ | 4-CH$_3$ | 6-CH$_3$ | 144 |
| XXX-5 | 1 | 6- ◁ | 2-Cl | 4-CH$_3$ | 158 |
| XXX-6 | 1 | 2- ◁ | 6-CH$_3$ | 4-Cl | 224-226 |
| XXX-7 | 2 | 2,4- ◁ | 6-C$_2$H$_5$ | H | *3.91 (s, 2 H, CH$_2$CO$_2$) 0.93, 0.62 (2 m, 4 H, CH$_2$ (cyclopropyl)) |
| XXX-8 | 2 | 2,4- ◁ | 6-CH$_3$ | H | 112 |
| XXX-9 | 2 | 2,6- ◁ | 4-CH$_3$ | H | *4.18 (s, 2 H, CH$_2$CO$_2$) 0.91, 0.64 (2 m, 4 H, CH$_2$ (cyclopropyl)) |

*1H-NMR (400 MHz, CDCl$_3$): shifts δ in ppm

Example XXXIV-1

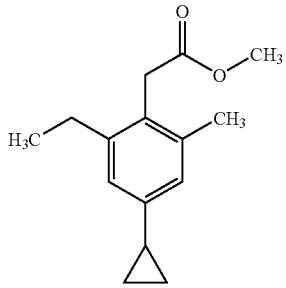

3 g of methyl 4-bromo-2-ethyl-6-methylphenyl acetate are initially charged in 115 ml of toluene and 5.7 ml of water, and the apparatus is flushed 3× with vacuum/argon. 1.24 g of cyclopropaneboronic acid, 5.27 g of potassium dihydrogen phosphate, 0.31 g of tricyclohexylphosphine and 0.12 g of palladium acetate are then added, and the mixture is heated at reflux in a pre-heated oil bath. The mixture is stirred under reflux for 8 h. The mixture is poured into 500 ml of 0.5N HCl and extracted 3× with 150 ml of toluene, the org. phases are combined and washed with 100 ml of sodium chloride solution, poor phase separation, the org. phases are dried over Na$_2$SO$_4$ and concentrated using a rotary evaporator. The residue is separated on a Biotage chromatography station using ethyl acetate/n-heptane (5:95 to 100:0). This gives 2.5 g of an oily residue (98% of theory).

*$^1$H-NMR (400 MHz, CDCl$_3$): δ: 1.81 (m, 1H, C$\underline{H}$-cycPr), 3.66 (s, 2+3H, CH$_2$—COOCH$_3$) ppm.

Analogously to Example (XXXIV-1) and in accordance with the general statements on the preparation, the following compounds of the formula (XXXIV) are obtained:

(XXXIV)

| Ex. No. | m | J | X | Y | R$^8$ | m. p. ° C. |
|---|---|---|---|---|---|---|
| XXXIV-2 | 1 | 4- ◁ | 2-CH$_3$ | 6-CH$_3$ | CH$_3$ | *1.81 (m, 1 H, C$\underline{H}$-cyc-Pr) 3.64 (s, 2 H, C$\underline{H}_2$CO$_2$CH$_3$) 3.67 (s, 3 H, CH$_2$—CO$_2$C$\underline{H}_3$) |
| XXXIV-3 | 1 | 2- ◁ | 6-C$_2$H$_5$ | 4-CH$_3$ | CH$_3$ | *1.89 (m, 1 H, C$\underline{H}$-cyc-Pr) 3.89 (s, 2 H, C$\underline{H}_2$CO$_2$CH$_2$CH$_3$) 4.13 (s, 3 H, CO$_2$C$\underline{H}_2$CH$_3$) |
| XXXIV-4 | 1 | 2- ◁ | 4-CH$_3$ | 6-CH$_3$ | CH$_3$ | was converted without further characterization into Example (XXX-4) |
| XXXIV-5 | 1 | 6- ◁ | 2-Cl | 4-CH$_3$ | CH$_3$ | *1.86 (m, 1 H, C$\underline{H}$-cyc-Pr) 3.69 (s, 3 H, CO$_2$C$\underline{H}_3$) |
| XXXIV-6 | 1 | 2- ◁ | 4-Cl | 6-CH$_3$ | CH$_3$ | *3.88 ppm (s, 2 H, CH$_2$—COO), 3.68 ppm (s, 3 H, OCH$_3$), 0.93 and 0.62 ppm (in each case m, 2 H, CH$_2$(cyclopropyl)) |

-continued

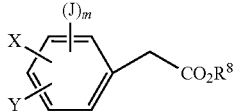

(XXXIV)

| Ex. No. | m | J | X | Y | R⁸ | m. p. ° C. |
|---|---|---|---|---|---|---|
| XXXIV-7 | 2 | 2,4- ──◁ | 6-CH₃ | H | CH₃ | *3.89 ppm (s, 2 H, CH₂—COO), 3.68 ppm (s, 3 H, OCH₃), 0.90 ppm (m, 4 H, CH₂(cyclopropyl)), 0.66 and 0.60 ppm (in each case m, 2 H, CH₂(cyclopropyl)) |
| XXXIV-8 | 2 | 2,6- ──◁ | 4-CH₃ | H | CH₃ | *4.12 ppm (s, 2 H, CH₂—COO), 3.68 ppm (s, 3 H, OCH₃), 0.89 and 0.62 ppm (in each case m, 4 H, CH₂(cyclopropyl)) |
| XXXIV-9 | 2 | 2,4- ──◁ | 6-C₂H₅ | H | CH₃ | *3.90 ppm (s, 2 H, CH₂—COO), 3.68 ppm (s, 3 H, OCH₃), 0.89 ppm (m, 4 H, CH₂(cyclopropyl)), 0.66 and 0.60 ppm (in each case m, 2 H, CH₂(cyclopropyl)) |

*¹H-NMR (400 MHz, CDCl₃): shifts δ in ppm

The logP values given in the table were determined in accordance with EEC Directive 79/831 Annex V.A8 by HPLC (High Performance Liquid Chromatography) on a reverse-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by retention times using linear interpolation between two successive alkanones).

The lambda max values were determined in the maxima of the chromatographic signals using the UV spectra from 200 nm to 400 nm.

Example A

Herbicidal Pre-Emergence Action

Seeds of monocotylos and dicotylos weed and crop plants are placed in sandy lawn in wood fibre pots and covered with soil. The test compounds, formulated in the form of wettable powders (WP) or as emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with the untreated controls (herbicidal effect in percent (%): 100% effect=the plants have died, 0% effect=like control plants).

Here, the following compounds, for example, controlled *Lolium multiflorum* and *Setaria viridis* at an application rate of 320 g/ha with ≧80% efficacy: Example: I-1-a-5, I-1-a-6, I-1-a-7, I-1-a-8, I-1-a-10, I-1-a-11, I-1-a-12, I-1-a-14, I-1-a-15, I-1-a-17, I-1-a-18, I-1-a-19, I-1-b-1, I-1-b-2, I-1-b-6, I-1-b-9, I-1-b-10, I-1-c-1, I-1-c2, I-1-c-7, I-1-c-8, I-1-c-10, I-1-c-12, I-1-c-13, I-1-c-14, I-1-c-15, I-1-c-16, I-1-c-17

Example B

Herbicidal Post-Emergence Action

Seeds of monocotylos and dicotylos weed and crop plants are placed in sandy lawn in wood fibre pots, covered with soil and cultivated in a greenhouse under good growth conditions. Two to three weeks after sowing, the test plants are treated at the one-leaf stage. The test compounds, formulated as wettable powders (WP) or as emulsion concentrates (EC), are then, as an aqueous suspension with a water application rate of 800 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=the plants have died, 0% effect=like control plants).

Here, the following compounds, for example, controlled *Lolium multiflorum* and *Setaria viridis* at an application rate of 320 g/ha with ≧90% efficacy: Ex. I-1-c-1.

Here, the following compounds, for example, controlled *Lolium multiforum* and *Setaria viridis* at an application rate of 80 g/ha with ≧80% efficacy: Example: I-1-a-2, I-1-a-5, I-1-a-6, I-1-a-7, I-1-a-8, I-1-a-10, I-1-a-11, I-1-a-12, I-1-a-14, I-1-a-15, I-1-a-17, I-1-a-18, I-1-a-19, I-1-b-1, I-1-b-6, I-1-b-9, I-1-b-10, I-1-c-3, I-1-c7, I-1-c-8, I-1-c-10, I-1-c-13, I-1-c-14, I-1-c-15, Example C Herbicidal Post-Emergence Action Seeds of monocotylos and dicotylos weed and crop plants are placed into sandy lawn in wood fibre pots or in plastic pots, covered with soil and cultivated in a greenhouse, during the vegetation period also outdoors outside of the greenhouse, under good growth conditions. Two to three weeks after sowing, the test plants are treated at the one- to three-leaf stage. The test compounds, formulated as wettable powders (WP) or liquid (EC), are, in the various dosages at a water application rate of 300 l/ha (converted), with wetting agent (0.2 to 0.3%) added, sprayed onto the plants and the surface of the soil. Three to four weeks after the treatment of the test plants, the effect of the preparations is rated visually in comparison to untreated controls (herbicidal effect in percent (%): 100% effect=the plants have died, 0% effect=like control plants).

Use of Safeners

If it is additionally to be tested as to whether safeners can improve the plant compatibility of test substances in the case of crop plants, the following options are used for applying the safener:

- seeds of the crop plants are, before sowing, dressed with safener substance (the amount of safener stated in percent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of test substances on crop plants without or with safener treatment, it is possible to assess the effect of the safener substance.

Container trials in the greenhouse, treatment with safener 1 day prior to herbicide application

TABLE 1

| | Application rate g of a.i./ha | 10 days after application Summer barley observed (%) | 28 days after application Summer barley observed (%) |
|---|---|---|---|
| I-1-a-5 | 50 | 80 | 40 |
| | 25 | 70 | 25 |
| | 12.5 | 50 | 15 |
| I-1-a-5 + mefenpyr | 50 + 100 | 60 | 15 |
| | 25 + 100 | 40 | 10 |
| | 12.5 + 100 | 20 | 0 |

TABLE 2

| | Application rate g of a.i./ha | 10 days after application Summer wheat observed (%) | 28 days after application Summer wheat observed (%) |
|---|---|---|---|
| I-1-a-5 | 50 | 70 | 75 |
| | 25 | 70 | 60 |
| | 12.5 | 60 | 40 |
| | 6.25 | 50 | 10 |
| I-1-a-5 + mefenpyr | 50 + 100 | 40 | 25 |
| | 25 + 100 | 20 | 20 |
| | 12.5 + 100 | 10 | 5 |
| | 6.25 + 100 | 3 | 0 |

TABLE 3

| | Application rate g of a.i./ha | 10 days after application Summer wheat observed (%) |
|---|---|---|
| I-1-a-12 | 25 | 50 |
| | 12.5 | 40 |
| | 6.25 | 10 |
| I-1-a-12 + mefenpyr | 25 + 100 | 20 |
| | 12.5 + 100 | 15 |
| | 6.25 + 100 | 0 |

TABLE 4

| | Application rate g of a.i./ha | 10 days after application Summer wheat observed (%) | 28 days after application Summer wheat observed (%) |
|---|---|---|---|
| I-1-a-12 | 50 | 60 | 65 |
| | 25 | 60 | 65 |
| | 12.5 | 50 | 25 |
| | 6.25 | 30 | 5 |
| I-1-a-12 + mefenpyr | 50 + 100 | 5 | 10 |
| | 25 + 100 | 5 | 5 |
| | 12.5 + 100 | 3 | 0 |
| | 6.25 + 100 | 2 | 0 |

TABLE 5

| | | 28 days after application | |
|---|---|---|---|
| | Application rate g of a.i./ha | Summer barley observed (%) | Summer wheat observed (%) |
| I-1-a-14 | 100 | | 85 |
| | 50 | 70 | 75 |
| | 25 | 60 | 50 |
| | 12.5 | 20 | 20 |
| I-1-a-14 + mefenpyr | 100 + 100 | | 40 |
| | 50 + 100 | 30 | 30 |
| | 25 + 100 | 25 | 20 |
| | 12.5 + 100 | 5 | 5 |

TABLE 6

| | Application rate g of a.i./ha | 10 days after application Summer barley observed (%) | 28 days after application Summer barley observed (%) |
|---|---|---|---|
| I-1-a-18 | 100 | 35 | 20 |
| | 50 | 25 | 10 |
| | 25 | 15 | |
| | 12.5 | 10 | |
| I-1-a-18 + mefenpyr | 100 + 50 | 20 | 5 |
| | 50 + 50 | 15 | 5 |
| | 25 + 50 | 10 | |
| | 12.5 + 50 | 5 | |

TABLE 7

| | Application rate g of a.i./ha | 10 days after application Summer wheat observed (%) |
|---|---|---|
| I-1-a-18 | 100 | 40 |
| | 50 | 25 |
| | 25 | 15 |
| | 12.5 | 10 |
| I-1-a-18 + mefenpyr | 100 + 50 | 10 |
| | 50 + 50 | 5 |
| | 25 + 50 | 5 |
| | 12.5 + 50 | 0 |

TABLE 8

|  | Application rate g of a.i./ha | 10 days after application Summer barley observed (%) |
|---|---|---|
| I-1-a-7 | 50 | 60 |
|  | 25 | 50 |
|  | 12.5 | 10 |
| I-1-a-7 + mefenpyr | 50 + 100 | 40 |
|  | 25 + 100 | 10 |
|  | 12.5 + 100 | 7 |

TABLE 9

|  | Application rate g of a.i./ha | 28 days after application Summer wheat observed (%) |
|---|---|---|
| I-1-a-7 | 100 | 80 |
|  | 50 | 70 |
|  | 25 | 60 |
|  | 12.5 | 30 |
| I-1-a-7 + mefenpyr | 100 + 100 | 50 |
|  | 50 + 100 | 40 |
|  | 25 + 100 | 20 |
|  | 12.5 + 100 | 10 |

TABLE 10

|  | Application rate g of a.i./ha | 10 days after application Summer wheat observed (%) |
|---|---|---|
| I-1-a-8 | 100 | 30 |
|  | 50 | 30 |
|  | 25 | 25 |
| I-1-a-8 + mefenpyr | 100 + 100 | 5 |
|  | 50 + 100 | 0 |
|  | 25 + 100 | 0 |

TABLE 11

|  | Application rate g of a.i./ha | 10 days after application Summer wheat observed (%) | 28 days after application Summer wheat observed (%) |
|---|---|---|---|
| I-1-a-9 | 25 | 65 | 50 |
|  | 12.5 | 60 |  |
| I-1-a-9 + mefenpyr | 25 + 100 | 50 | 25 |
|  | 12.5 + 100 | 15 |  |

TABLE 12

|  | Application rate g of a.i./ha | 10 days after application Summer barley observed (%) | 28 days after application Summer barley observed (%) |
|---|---|---|---|
| I-1-b-1 | 50 |  | 80 |
|  | 25 | 65 | 30 |
|  | 12.5 | 30 | 10 |
| I-1-b-1 + mefenpyr | 50 + 100 |  | 30 |
|  | 25 + 100 | 30 | 15 |
|  | 12.5 + 100 | 5 | 0 |

TABLE 13

|  | Application rate g of a.i./ha | 10 days after application Summer wheat observed (%) | 28 days after application Summer wheat observed (%) |
|---|---|---|---|
| I-1-b-1 | 100 |  | 95 |
|  | 50 |  | 90 |
|  | 25 | 60 | 40 |
|  | 12.5 | 50 |  |
| I-1-b-1 + mefenpyr | 100 + 100 |  | 40 |
|  | 50 + 100 |  | 20 |
|  | 25 + 100 | 25 | 0 |
|  | 12.5 + 100 | 15 |  |

TABLE 14

|  | Application rate g of a.i./ha | 10 days after application Summer barley observed (%) | 10 days after application Summer wheat observed (%) |
|---|---|---|---|
| I-1-c-13 | 50 | 30 | 40 |
|  | 25 | 20 | 30 |
|  | 12.5 | 5 | 20 |
| I-1-c-13 + mefenpyr | 50 + 50 | 10 | 30 |
|  | 25 + 50 | 5 | 20 |
|  | 12.5 + 50 | 0 | 5 |

TABLE 15

|  | Application rate g of a.i./ha | 10 days after application Summer barley observed (%) | 28 days after application Summer barley observed (%) |
|---|---|---|---|
| I-1-c-7 | 100 | 90 | 95 |
|  | 50 | 60 | 50 |
|  | 25 | 40 |  |
|  | 12.5 | 10 |  |
| I-1-c-7 + mefenpyr | 100 + 100 | 50 | 25 |
|  | 50 + 100 | 10 | 5 |
|  | 25 + 100 | 3 |  |
|  | 12.5 + 100 | 0 |  |

TABLE 16

|  | Application rate g of a.i./ha | 10 days after application Summer wheat observed (%) | 28 days after application Summer wheat observed (%) |
|---|---|---|---|
| I-1-c-7 | 50 |  | 80 |
|  | 25 | 60 | 20 |
|  | 12.5 | 20 | 10 |
| I-1-c-7 + mefenpyr | 50 + 100 |  | 20 |
|  | 25 + 100 | 30 | 10 |
|  | 12.5 + 100 | 10 | 5 |

Example D

Phaedon Test (Spray Treatment)

Solvents: 78 parts by weight of acetone
1.5 parts by weight of dimethylformamide
Emulsifier: 0.5 part by weight of alkylaryl polyglycol ether
To produce a suitable proportion of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larva of the mustard beetle (*Phaedon cochleariae*).

After the desired period of time, the effect in percent is determined. 100% means that all beetle larva have been killed, 0% means that none of the beetle larva have been killed.

In this test, for example, the following compounds of the Preparation Examples show, at an application rate of 500 g/ha, an efficacy of ≧80%: Example: I-1-a-2, I-1-a-4, I-1-a-6, I-1-a-7, I-1-a-10, I-1-a-11, I-1-a-12, I-1-a-14, I-1-a-24, I-1-a-25, I-1-b-5, I-1-b-11, I-1-b-13, I-1-c-7, I-1-c-12, I-1-c-20, I-1-c-22, I-1-c-23, I-1-d-1, Example No. E Myzus Test (YZUPE Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≧90%: Example: I-1-a-2, I-1-a-4, I-1-a-6, I-1-a-7, I-1-a-9, I-1-a-11, I-1-a-12, I-1-a-14, I-1-a-15, I-1-a-17, I-1-a-20, I-1-a-22, I-1-b-3, I-1-b-4, I-1-b-6, I-1-b-10, I-1-b-13, I-1-c-1, I-1-c-8, I-1-c-9, I-1-c-14, I-1-c-15, I-1-c-19, Example No. F

*Tetranychus* Test, OP-Resistant (TETRUR Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in percent is determined. 100% means that all spider mites have been killed; 0% means that none of the spider mites have been killed.

In this test, for example, the following compounds of the Preparation Examples show, at an application rate of 100 g/ha or 20 g/ha*, an efficacy of ≧80%: Example: I-1-a-4, I-1-a-5, I-1-a-6, I-1-a-7, I-1-a-8, I-1-a-9, I-1-a-10, I-1-a-11, I-1-a-14, I-1-a-17, I-1-a-19, I-1-a-20, I-1-a-25*, I-1-b-4, I-1-b-8, I-1-b-11, I-1-b-15, I-1-c-9, I-1-c-12, I-1-c-13, I-1-c-14, I-1-c-15, I-1-c-16, I-1-c-20, I-1-c-25, I-1-d-1, I-8-b-2.

Example No. G

*Myzus Persicae* Test, Hydroponic Treatment (MYZUPE sys.)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration refers to the amount of active compound per volume unit of water (mg/l=ppm). The treated water is filled into vessels containing a pea plant (*Pisum sativum*) which is then infested with the green peach aphid (*Myzus persicae*).

After the desired period of time, the kill in percent is determined. 100% means that all aphids have been killed; 0% means that none of the aphids have been killed.

In this test, for example, the following compound of the Preparation Examples shows, at a concentration of 20 ppm, an efficacy of ≧90%: Ex. I-1-a-4.

Example No. H

*Meloidogyne* Test (MELGIN Spray Treatment)

Solvent: 80 parts by weight of acetone

To produce a suitable preparation of active compound, 1 part by weight of active compound is mixed with the stated amount of solvent and the concentrate is diluted with water to the desired concentration.

Vessels are filled with sand, solution of active compound, *Meloidogyne incognita* egg-larva suspension and lettuce seeds. The lettuce seeds germinate and the plants develop. On the roots, galls are formed.

After the desired period of time, the nematicidal action is determined in % by the gall formation. 100% means that no galls were found; 0% means that the number of galls on the treated plants corresponds to that of the untreated control.

In this test, for example, the following compounds of the Preparation Examples show, at an application rate of 20 ppm, an efficacy of ≧80%: Example: I-1-a-7, I-1-a-12.

Example No. I

*Lucilia Cuprina* Test (LUCICU)

Solvent: Dimethyl sulphoxide

To produce a suitable preparation of active compound, 1 part by weight of active compound is mixed with the stated amount of solvent and the concentrate is diluted with water to the desired concentration.

Vessels containing horsemeat which had been treated with the preparation of active compound of the desired concentration are populated with *Lucilia* cuprina larva.

After the desired period of time, the kill in % is determined. 100% means that all larva have been killed; 0% means that none of the larva have been killed.

In this test, for example, the following compounds of the Preparation Examples show, at an application rate of 100 ppm, an efficacy of ≧80%: Example: I-1-a-4, I-1-b-4, I-1-c-3.

Example No. J

Boophilus Microplus Test (BOOPMI Injection)

Solvent: Dimethyl sulphoxide

To produce a suitable preparation of active compound, 1 part by weight of active compound is mixed with the stated amount of solvent and the concentrate is diluted with solvent to the desired concentration.

The solution of active compound is injected into the abdomen (*Boophilus microplus*), the animals are transferred into dishes and stored in a climatized room.

After the desired period of time, the effect in percentage is determined. 100% means that none of the ticks has laid any fertile eggs.

In this test, for example, the following compounds of the Preparation Examples show, at an application rate of 20 µg/animal, an effect of ≧80%: Example: I-1-a-1, I-1-a-2, I-1-a-4, I-1-a-6, I-1-b-4, I-1-c-3.

Example K

Critical Concentration Test/Soil Insects—Treatment of Transgenic Plants

Test insect: *Diabrotica balteata*—larva in the soil
Solvent: 7 parts by weight of acetone
Emulsifier: 1 part by weight of alkylaryl polyglycol ether To produce a suitable preparation of active compound, 1 part by weight of active compound is mixed with the stated amounts of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pergermaninated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example L

Heliothis Virescens Test—Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

Example M

Activity Increase by Ammonia/Phosphonium Salts in Combination with Penetrants

Myzus Persicae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with emulsifier-containing water to the desired concentration. For the application with penetrants (rapeseed oil methyl ester 500 EW), ammonium or phosphonium salts or ammonium salts and penetrants (rapeseed oil methyl ester 500 EW), these are in each case added in a concentration of 1000 ppm to the spray liquor.

Paprika plants (*Capsicum annuum*) which are heavily infested by the green peach aphid (*Myzus persicae*) are treated by being sprayed to run off point with the preparation of active compound at the desired concentration.

After the desired period of time, the kill in % is determined. 100% means that all animals have been killed; 0% means that none of the animals have been killed.

In this test, for example, the following compounds of the Preparation Examples show good efficacy: see table

TABLE

| Active compound | Concentration (ppm) | Kill (%) after 6 d | +AS 1000 ppm | +RME 1000 ppm | +AS +RME in each case 1000 ppm |
|---|---|---|---|---|---|
| I-1-a-15 | 20 | 95 | 95 | 95 | 98 |
|  | 4 | 5 | 15 | 55 | 95 |

AS = Ammonium sulphate

Example N

Aphis Gossypii Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with emulsifier-containing water to the desired concentration. For the application with penetrants (rapeseed oil methyl ester 500 EW), ammonium or phosphonium salts or ammonium salts and penetrants (rapeseed oil methyl ester 500 EW), these are in each case added in a concentration of 1000 ppm to the spray liquor.

Cotton plants (*Gossypium hirsutum*) which are heavily infested by the cotton aphid (*Aphis gossypii*) are treated by being sprayed to run off point with the preparation of active compound at the desired concentration.

After the desired period of time, the kill in % is determined. 100% means that all aphids have been killed; 0% means that none of the aphids have been killed.

In this test, for example, the following compounds of the Preparation Examples show good efficacy: see table

TABLE

| Active compound | Concentration (ppm) | Kill (%) after 6 d | +AS 1000 ppm | +RME 1000 ppm | +AS +RME in each case 1000 ppm |
|---|---|---|---|---|---|
| I-1-a-7 | 20 | 55 | 65 | 75 | 99 |

AS = Ammonium sulphate

Example O

Increase of penetration into the plant by ammonium or phosphonium salts and synergistic increase of penetration into the plant by ammonium/phosphonium salts in combination with penetrants.

In this test, the penetration of active compounds through enyzmatically isolated cuticles of apple tree leaves was measured.

Use was made of leaves which, fully developed, were cut from apple trees of the cultivar golden delicious. The cuticles were isolated by initially filling leaf discs punched out and stained with dye on the underside by vacuum infiltration with a pectinase solution (0.2 to 2% strength) buffered to a pH between 3 and 4, then sodium azide was added and allowing the leaf discs treated in this manner to stand until the original leaf structure has dissolved and the non-cellular cuticles have detached.

Only the cuticles, free from hairs and stoma, of the upper sides of the leaves were then used. They were washed repeatedly alternating with water and a buffer solution of pH 7. The clean cuticles obtained were then mounted on Teflon plates and smoothed and dried with a gentle stream of air.

In the next step, the cuticle membranes obtained in this manner were placed into stainless steel diffusion cells (=transport chambers) for membrane transport studies. To this end, the cuticles were placed with a pincette into the centre of the edges, coated with silicone fat, of the diffusion cells and closed with a ring, which had also been treated with fat. The arrangement was chosen such that the morphological outside of the cuticles was facing outwards, i.e. exposed to air, whereas the original inside was facing the interior of the diffusion cells.

The diffusion cells were filled with a 30% strength ethylene glycol/water solution. To determine the penetration, in each case 10 μl of the spray liquor of the composition below were applied to the outside of the cuticles. The spray liquor was prepared using local tap water of medium hardness.

After the spray liquors had been applied, the water was allowed to evaporate and the chambers were inverted and placed into thermostated taps in which temperature and atmospheric humidity could be adjusted using a gentle stream of air onto the cuticles with the spray coating (20° C., 60% rh). At regular intervals, an autosampler took aliquots and the active compound content was determined by HPLC.

The test results are shown in the table below. The stated numbers are average values of 8 to 10 measurements. It is clearly evident that, together with RME, there is a superadditive (synergistic) effect.

TABLE 1

| | | Penetration after 24 h/% | | |
|---|---|---|---|---|
| Active compound | a.i. | a.i. + AS (1 g/l) | a.i. + RME (1 g/l) | a.i. + RME (1 g/l) + AS (1 g/l) |
| Example I-1-a-21 200 ppm in acetone/water 4:6 | 2 | 1.1 | 35.6 | 56.9 |

RME = rapeseed oil methyl ester (formulated as 500 EW, concentration stated in g of active compound(s))
AS = Ammonium sulphate

The invention claimed is:
1. A compound of formula (I)

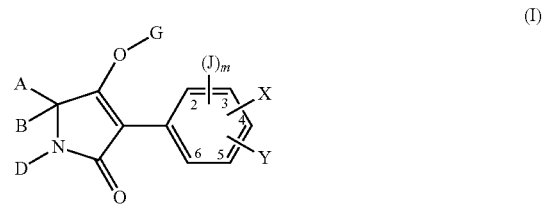

wherein:
J represents $C_3$-$C_8$-cycloalkyl and at least one J is present at the 2-, 3-, 5-, or 6-position,
X represents hydrogen, halogen, $C_1$-$C_6$-alkyl, $C_1$-$C_4$-haloalkyl, $C_1$-$C_6$-alkoxy or $C_1$-$C_4$-haloalkoxy,
Y represents hydrogen, $C_1$-$C_6$-alkyl, $C_1$-$C_4$-haloalkyl, halogen, $C_1$-$C_6$-alkoxy or $C_1$-$C_4$-haloalkoxy,
m represents a number 1, 2 or 3,
with the proviso that at least one of the radicals J, X or Y is located in the 2-position of the phenyl radical and is not hydrogen,
A represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 or 6 ring atoms, phenyl-$C_1$-$C_6$-alkyl or naphthyl-$C_1$-$C_6$-alkyl,
B represents hydrogen, $C_1$-$C_{12}$-alkyl or $C_1$-$C_8$-alkoxy-$C_1$-$C_6$-alkyl or
A, B and the carbon atom to which they are attached represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_4$-alkoxy-$C_1$-$C_4$-alkoxy, $C_1$-$C_8$-alkylthio, halogen or phenyl, or
A, B and the carbon atom to which they are attached represent $C_3$-$C_6$-cycloalkyl which is substituted by an alkylenediyl group or by an alkylenedioxyl group or by an alkylenedithioyl group which optionally contains one or two not directly adjacent oxygen and/or sulphur atoms and which is optionally substituted by $C_1$-$C_4$-alkyl, which group, together with the carbon atom to which it is attached, forms a further five- to eight-membered ring, or A, B and the carbon atom to which they are attached represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur, D represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted, $C_3$-$C_8$-cycloalkyl, in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms, phenyl-$C_1$-$C_6$-alkyl or hetaryl-$C_1$-$C_6$-alkyl having 5 or 6 ring atoms or A and D together represent in each case optionally substituted $C_3$-$C_6$-alkanediyl or $C_3$-$C_6$-alkenediyl in which optionally one methylene group is replaced by a carbonyl group, oxygen or sulphur, wherein possible substituents being in each case:
halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms that may contain oxygen or sulphur or which optionally contain one of the following groups

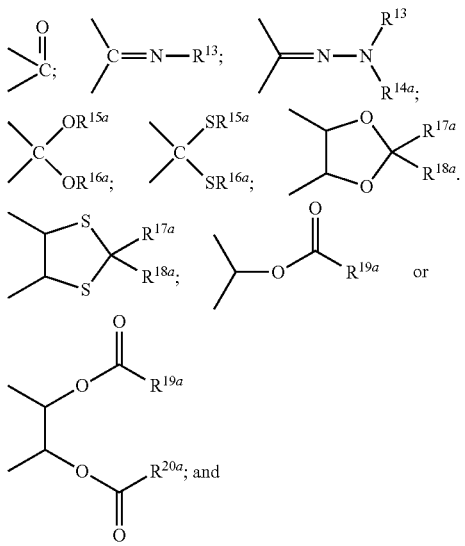

G represents hydrogen (a) or represents one of the groups (b)

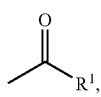

(c)

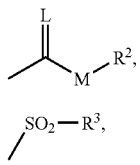

(d)

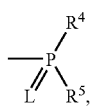

(e)

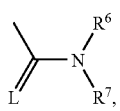

E or (f)

(g)

in which
E represents a metal ion equivalent or an ammonium ion,
L represents oxygen or sulphur and
M represents oxygen or sulphur, $R^1$ represents in each case
optionally halogen-substituted $C_1$-$C_{20}$-alkyl, $C_2$-$C_{20}$-alkenyl, $C_1$-$C_8$-alk-oxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more not directly adjacent ring members are replaced by oxygen and/or sulphur, optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl -substituted phenyl, optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, optionally halogen- or $C_1$-$C_6$-alkyl-substituted 5- or 6-membered hetaryl, optionally halogen- or $C_1$-$C_6$-alkyl-substituted phenoxy-$C_1$-$C_6$-alkyl or optionally halogen-, amino- or $C_1$-$C_6$-alkyl-substituted 5- or 6-membered hetaryloxy-$C_1$-$C_6$-alkyl, $R^2$ represents in each case
optionally halogen-substituted $C_1$-$C_{20}$-alkyl, $C_2$-$C_{20}$-alkenyl, $C_1$-$C_8$-alk-oxy-$C_2$-$C_8$-alkyl, poly-$C_1$-$C_8$-alkoxy-$C_2$-$C_8$-alkyl, optionally halogen-, $C_1$-$C_6$-alkyl- or $C_1$-$C_6$-alkoxy-substituted $C_3$-$C_8$-cycloalkyl or optionally halogen-, cyano-, nitro-, $C_6$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur, $R^{13}$ represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14a}$ represents hydrogen or $C_1$-$C_8$-alkyl or $R^{13}$ and $R^{14a}$ together represent $C_4$-$C_6$-alkanediyl, $R^{15a}$ and $R^{16a}$ are identical or different and represent $C_1$-$C_6$-alkyl or $R^{15a}$ and $R^{16a}$ together represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ independently of one another represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl) amino or di-($C_3$-$C_{10}$-alkenyl)amino.

2. A compound of formula (I) according to claim 1 in which

J represents $C_3$-$C_6$-cycloalkyl,

X represents hydrogen, fluorine, chlorine, bromine, iodine, $C_1$-$C_4$-alkyl, trifluoromethyl, $C_1$-$C_4$-alkoxy, difluoromethoxy or trifluoromethoxy, Y represents hydrogen, fluorine, chlorine, bromine, iodine, $C_1$-$C_4$-alkyl, trifluoromethyl, $C_1$-$C_4$-alkoxy, difluoromethoxy or trifluoromethoxy, m represents a number 1 or 2, A represents
 hydrogen,
 $C_1$-$C_6$-alkyl, $C_1$-$C_4$-alkoxy-$C_1$-$C_2$-alkyl, each of which is optionally mono- to trisubstituted by fluorine or chlorine, or
 $C_3$-$C_6$-cycloalkyl which is optionally mono- or disubstituted by $C_1$-$C_2$-al-kyl or $C_1$-$C_2$-alkoxy or,
 phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B represents hydrogen, $C_1$-$C_4$-alkyl or $C_1$-$C_2$-alkoxy-$C_1$-$C_2$-alkyl or A, B and the carbon atom to which they are attached represent saturated or unsaturated $C_5$-$C_7$-cycloalkyl in which optionally one ring member is replaced by oxygen or sulphur and which is optionally mono- or disubstituted by $C_1$-$C_6$-alkyl, trifluoromethyl, $C_1$-$C_6$-alkoxy or $C_1$-$C_3$-alkoxy-$C_1$-$C_3$-alkoxy, or A, B and the carbon atom to which they are attached represent $C_5$-$C_6$-cycloalkyl which is substituted by an alkylenediyl group or by an alkylenedioxyl group or by an alkylenedithiol group which optionally contains one or two not directly adjacent oxygen or sulphur atoms and which is optionally substituted by methyl or ethyl, which group together with the carbon atom to which it is attached forms a further five- or six-membered ring, or A, B and the carbon atom to which they are attached represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, D represents
 hydrogen,
 $C_1$-$C_6$-alkyl, $C_3$-$C_6$-alkenyl, $C_1$-$C_4$-alkoxy-$C_2$-$C_3$-alkyl, each of which is optionally mono- to trisubstituted by fluorine, or
 $C_3$-$C_6$-cycloalkyl which is optionally mono- or disubstituted by $C_1$-$C_4$-alkyl, $C_1$-$C_4$-alkoxy or $C_1$-$C_2$-haloalkyl in which optionally one methylene group is replaced by oxygen, or A and D together represent optionally mono- or disubstituted $C_3$-$C_5$-alkanediyl in which one methylene group may be replaced by a carbonyl group, or A and D together with the atoms to which they are attached represent one of the groups AD-1 to AD-10:

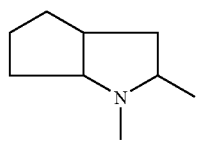

AD-1

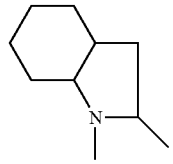

AD-2

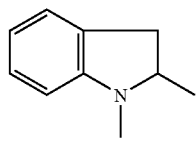

AD-3

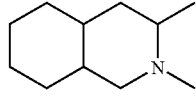

AD-4

-continued

AD-5

AD-6

AD-7

AD-8

AD-9

AD-10

G represents hydrogen (a) or represents one of the groups (b) $\overset{O}{\underset{}{\|}}\!\!-\!\!R^1$, (c) $\underset{M}{\overset{L}{\|}}\!\!-\!\!R^2$, (d) $-SO_2-R^3$, (e) $\underset{L}{\overset{R^4}{\underset{\|}{P}}}\!\!-\!\!R^5$, (f) E or (g) $\underset{L}{\overset{\|}{\underset{}{}}}\!\!-\!\!N\!\!<\!\!\overset{R^6}{\underset{R^7}{}}$ in which
E represents a metal ion equivalent or an ammonium ion,
L represents oxygen or sulphur
M represents oxygen or sulphur, $R^1$ represents
$C_1$-$C_8$-alkyl, $C_2$-$C_{18}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, or
phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ represents
$C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
$C_3$-$C_6$-cycloalkyl which is optionally monosubstituted by $C_1$-$C_2$-alkyl or $C_1$-$C_2$-alkoxy or
phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ represents
$C_1$-$C_6$-alkyl which is optionally mono- to trisubstituted by fluorine or
phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ represents
$C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or
phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or tri-fluoromethyl, $R^5$ represents $C_1$-$C_6$-alkoxy or $C_1$-$C_6$-alkylthio, $R^6$ represents
hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl,
phenyl which is optionally monosubstituted by fluorine, chlorine, bromine, trifluoromethyl, $C_1$-$C_4$-alkyl or $C_1$-$C_4$-alkoxy, or
benzyl which is optionally monosubstituted by fluorine, chlorine, bromine, $C_1$-$C_4$-alkyl, trifluoromethyl or $C_1$-$C_4$-alkoxy, $R^7$ represents $C_1$-$C_6$-alkyl, $C_3$-$C_6$-alkenyl or $C_1$-$C_6$-alkoxy-$C_1$-$C_4$-alkyl, $R^6$ and $R^7$ together represent a $C_4$-$C_5$-alkylene radical which is optionally substituted by methyl or ethyl and in which optionally one methylene group is replaced by oxygen or sulphur.

3. A compound of formula (I) according to claim 1 in which
J represents cyclopropyl, dicyclopropyl, cyclobutyl, cyclopentyl, cyclohexyl,
X represents hydrogen, fluorine, chlorine, bromine, methyl, ethyl, propyl, methoxy or ethoxy,
Y represents hydrogen, chlorine, bromine, methyl, ethyl, propyl, trifluoromethyl, methoxy, ethoxy or trifluoromethoxy,
m represents the number 1 or 2,
where the radicals J, X and Y are arranged in the following phenyl substitution patterns

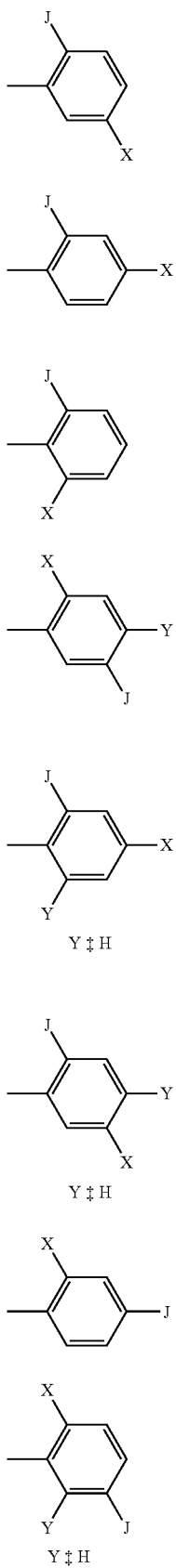

(A)

(B)

(C)

(D)

(E)

Y ‡ H (F)

Y ‡ H (G)

(J)

Y ‡ H

-continued

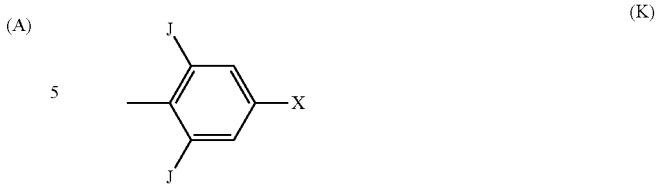

(K)

Y = H

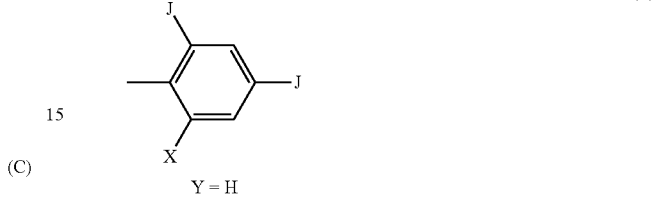

(L)

Y = H where only in the phenyl substitution patterns (B), (K) and (L), X may also represent hydrogen, A represents hydrogen, or $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, B represents hydrogen, methyl or ethyl, or A, B and the carbon atom to which they are attached represents saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy, methoxyethoxy, butoxy, methoxymethyl or ethoxyethoxy, or A, B and the carbon atom to which they are attached represent $C_6$-cycloalkyl which is optionally substituted by an alkylenedioxyl group which contains two not directly adjacent oxygen atoms, or A, B and the carbon atom to which they are attached represents $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, D represents hydrogen, represents $C_1$-$C_4$-alkyl, $C_3$-$C_4$-alkenyl, $C_1$-$C_4$-alkoxy-$C_2$-$C_3$-alkyl, each of which is optionally mono- to trisubstituted by fluorine, represents cyclopropyl, cyclopentyl or cyclohexyl, or A and D together represent $C_3$-$C_5$-alkanediyl which is optionally monosubstituted by methyl or methoxy and in which optionally one carbon atom is replaced by oxygen or sulphur or represents group AD-1

AD-1

, and

G represents hydrogen (a) or represents one of the groups

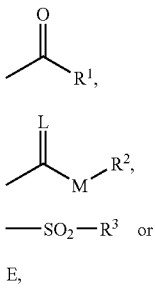

(b)

(c)

—SO₂—R³ or (d)

E, (f)

in which
L represents oxygen or sulphur,
represents oxygen or sulphur and
E represents an ammonium ion
R¹ represents
$C_1$-$C_6$-alkyl, $C_2$-$C_{17}$-alkenyl, $C_1$-$C_2$-alkoxy-$C_1$-alkyl, $C_1$-$C_2$-alkylthio -$C_1$-alkyl, each of which is optionally monosubstituted by chlorine, or
cyclopropyl or cyclohexyl, each of which is optionally monosubstituted by fluorine, chlorine, methyl or methoxy, or
phenyl which is optionally monosubstituted by fluorine, chlorine, bromine, cyano, nitro, methyl, methoxy, trifluoromethyl or trifluoromethoxy,
R² represents
$C_1$-$C_8$-alkyl, $C_2$-$C_6$-alkenyl or $C_1$-$C_4$-alkoxy-$C_2$-$C_3$-alkyl, each of which is optionally monosubstituted by fluorine, or
phenyl or benzyl,
R³ represents $C_1$-$C_8$-alkyl.

4. A compound of formula (I) according to claim 1 in which
J represents cyclopropyl,
X represents chlorine, methyl or ethyl,
Y represents chlorine, methyl, ethyl or hydrogen,
m represents the number 1 or 2,
where the radicals J, X and Y are arranged in the following phenyl substitution patterns

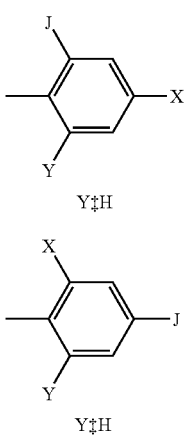

(E)

Y‡H (H)

Y‡H

-continued

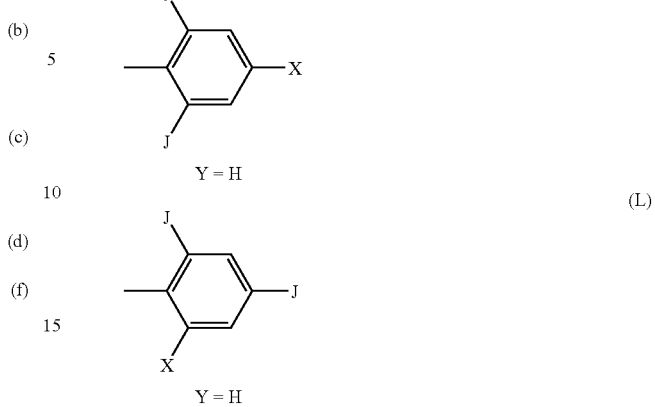

(K)

Y = H (L)

Y = H

A represents $C_1$-$C_4$-alkyl or cyclopropyl,
B represents hydrogen or methyl or
A, B and the carbon atom to which they are attached represent saturated $C_5$-$C_6$-cycloalkyl in which optionally one ring member is replaced by oxygen and which is optionally monosubstituted by methoxy, ethoxy, butoxy or methoxymethyl,
A, B and the carbon atom to which they are attached represent $C_6$-cycloalkyl which is optionally substituted by a $C_2$-$C_3$-alkylenedioxyl group having two not directly adjacent oxygen atoms,
D represents hydrogen or
A and D together represent $C_3$-$C_5$-alkanediyl,
G represents hydrogen (a) or represents one of the groups

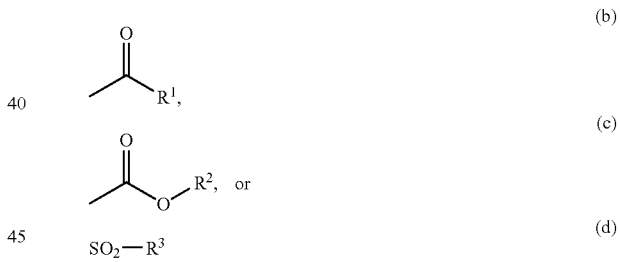

(b)

(c)

(d)

R¹ represents $C_1$-$C_6$-alkyl or represents phenyl which is monosubstituted by chlorine,
R² represents $C_1$-$C_8$-alkyl,
R³ represents $C_1$-$C_8$-alkyl.

5. A composition comprising an effective amount of an active compound combination comprising, as components
(a') at least one substituted cyclic ketoenol of the formula (I) according to claim 1 and
(b') at least one crop plant compatibility-improving compound selected from the following group consisting of:
4-dichloroacetyl-1-oxa-4-azaspiro[4.5]decane, 1-dichloroacetylhexahydro-3,3,8a -trimethylpyrrolo[1,2-a]pyrimidin-6(2H)-one, 4-dichloroacetyl-3,4-dihydro-3-methyl-2H-1,4-benzoxazine, 1-methylhexyl 5-chloroquinoline-8-oxyacetate 3-(2-chlorobenzyl)-1-(1-methyl-1-phenylethyl)urea, α-(cyanomethoximino) phenylacetonitrile, 2,4-dichlorophenoxyacetic acid, 4-(2,4-dichlorophenoxy)butyric acid, 1-(1-methyl-1-phenylethyl)-3-(4-methylphenyl)urea, 3,6-dichloro-2-methoxybenzoic, S-1-methyl-1-phenylethyl piperidine- 1-thiocarboxylate, 2,2-dichloro-N-(2-oxo-2-(2-propenylamino)ethyl)-N-(2-propenyl)acetamide, 2,2-dichloro-N,N-di-2-propenylacetamide, 4,6-dichloro-2-phenylpyrimidine, ethyl 1-(2,4-dichlorophenyl)-5-trichloromethyl-1H-1,2,4-triazole-3-carboxylate, phenylmethyl 2-chloro-4-trifluoromethylthiazole-5-carboxylate, 4-chloro-N-(1,3-dioxolan-2-ylmethoxy)-α-trifluoroacetophenone oxime, 3-dichloroacetyl-5-(2-furanyl)-2,2-dimethyloxazolidine, ethyl 4,5-dihydro-5,5-diphenyl-3-isoxazolecarboxylate, 1-(ethoxycarbonyl)ethyl 3,6-dichloro-2-methoxybenzoate, (4-chloro-o-tolyloxy)acetic acid, 2-(4-chloro-o-tolyloxy)propionic acid, diethyl 1-(2,4-dichorophenyl)-4,5-dihydro-5-methyl-1H -pyrazole-3,5-dicarboxylate, 2-dichloromethyl-2-methyl-1,3-dioxolane, 2-propenyl-1-oxa -4-azaspiro[4.5]decane-4-carbodithioate, 1,8-naphthalic anhydride, α-(1,3-dioxolan-2-ylmethoximino)phenylacetonitrile, 2,2-dichloro-N-(1,3-dioxolan-2-ylmethyl)-N-(2-propeny)acetamide, 3-dichloroacetyl-2,2-dimethyloxazolidine, 3-dichloroacetyl-2,2,5-trimethyloxazolidine, 4-(4-chloro-o-tolyl) butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichloro-phenyl)-5-(1,1-dimethylethyl)-1H-pyrazole-3-carboxylate, ethyl 1-(2, 4-dichlorophenyl) -5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid, 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea, N-(2-methoxybenzoyl)-4-[(methylaminocarbonyl)amino]benzenesulphonamide [()]], 1-[4-(N-2-methoxybenzoylsulphamoyl)phenyl]-3,3-dimethylurea, 1-[4-(N-4,5-dimethylbenzoyl -sulphamoyl)phenyl]-3-methylurea, 1-[4-(N-naphthylsulphamoyl)phenyl]-3,3-dimethylurea, and N-(2-methoxy-5-methylbenzoyl)-4-(cyclopropylaminocarbonyl) -benzenesulphonamide, and/or one, at least one of a compound of:
formula (IIa)

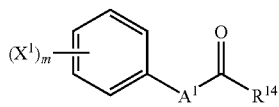

(IIa)

or formula (IIb)

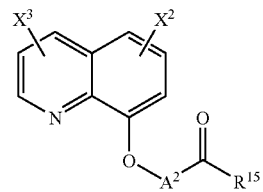

(IIb)

and/or the formula (IIc)

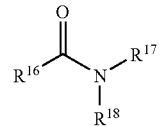

(IIc)

where
m represents a number 0, 1, 2, 3, 4 or 5,
$A^1$ represents one of the divalent heterocyclic groupings shown below

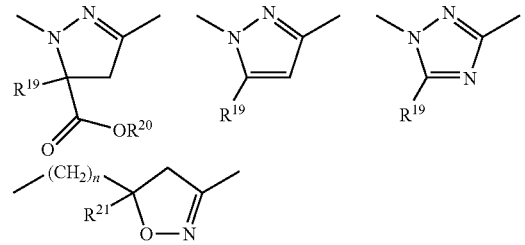

n represents a number 0, 1, 2, 3, 4 or 5,
$A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl) amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl) -amino,
$R^{16}$ represents in each case optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or one of the following compounds, formula (IId)

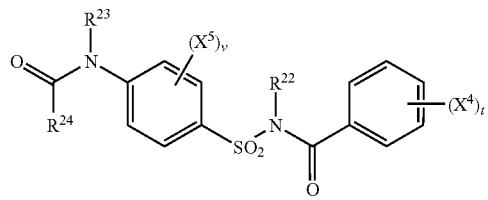

or formula (IIe)

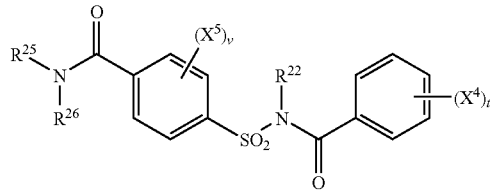

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

6. A composition according to claim 5, in which the crop plant compatibility-improving compound is selected from the group consisting of:

cloquintocet-mexyl, fenchlorazole-ethyl, isoxadifen-ethyl, mefenpyr-diethyl, furilazole, fenclorim, cumyluron, dymron or the compounds

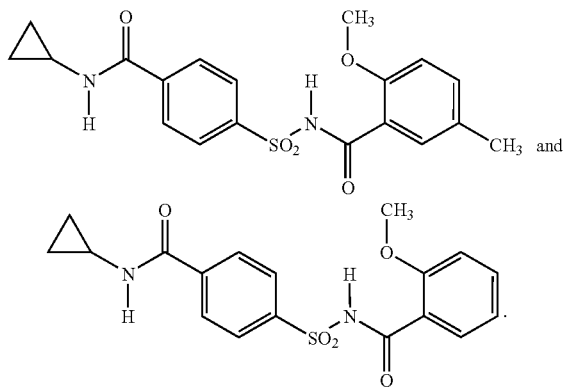

7. A composition according to claim 5, in which the crop plant compatibility-improving compound is cloquintocet-mexyl.

8. A composition according to claim 5, in which the crop plant compatibility-improving compound is mefenpyr-diethyl.

9. A composition for controlling pests and/or unwanted vegetation, comprising at least one compound of the formula (I) according to claim 1.

10. A compound of the formula (I) according to claim 1 capable of controlling animal pests and/or unwanted vegetation.

11. A composition according to claim 5 capable of controlling unwanted vegetation.

12. A composition, comprising at least one compound of formula (I) according to claim 1 and at least one salt of the formula (III')

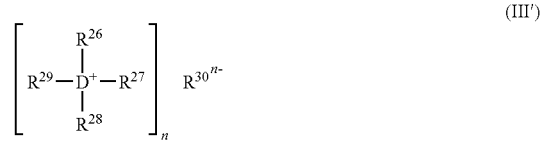

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated optionally substituted $C_1$-$C_8$-alkylene, where the substituents may be selected from the group consisting of halogen, nitro and cyano, n represents 1, 2, 3 or 4, $R^{30}$ represents an inorganic or organic anion.

13. A composition according to claim 12, further comprising at least one penetrant.

14. A method for improving the activity of a pesticide and/or a herbicide comprising an active compound of the formula (I) according to claim 1 comprising preparing ready-to-use composition of said active compound and a salt.

15. A method according to claim 14, wherein the ready to use composition is prepared using a penetrant.

16. A compound of formula (I) according to claim 1, wherein at least one J is present at the 2- or 6-position.

* * * * *